United States Patent
Hirota et al.

(10) Patent No.: US 11,130,981 B2
(45) Date of Patent: Sep. 28, 2021

(54) TRANSFORMANT, METHOD FOR PRODUCING TRANSFORMANT, AND METHOD FOR DETECTING PRESENCE OR ABSENCE OF REDUCED PHOSPHORUS COMPOUND USING TRANSFORMANT

(71) Applicant: HIROSHIMA UNIVERSITY, Hiroshima (JP)

(72) Inventors: Ryuichi Hirota, Hiroshima (JP); Akio Kuroda, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 336 days.

(21) Appl. No.: 16/328,560

(22) PCT Filed: Jul. 31, 2017

(86) PCT No.: PCT/JP2017/027588
§ 371 (c)(1),
(2) Date: Feb. 26, 2019

(87) PCT Pub. No.: WO2018/042987
PCT Pub. Date: Mar. 8, 2018

(65) Prior Publication Data
US 2021/0147896 A1  May 20, 2021

(30) Foreign Application Priority Data

Aug. 31, 2016  (JP) .............................. JP2016-170317

(51) Int. Cl.
*A01N 63/00* (2020.01)
*C12Q 1/02* (2006.01)
*C12N 1/20* (2006.01)
*C12N 15/70* (2006.01)

(52) U.S. Cl.
CPC ................. *C12Q 1/02* (2013.01); *C12N 1/20* (2013.01); *C12N 15/70* (2013.01)

(58) Field of Classification Search
CPC ...................................................... C12Q 1/12
See application file for complete search history.

(56) References Cited

U.S. PATENT DOCUMENTS

| | | |
|---|---|---|
| 2014/0051134 A1 | 2/2014 | Kuroda et al. |
| 2015/0125934 A1 | 5/2015 | Kuroda et al. |

FOREIGN PATENT DOCUMENTS

| | | |
|---|---|---|
| EP | 2860242 | 4/2015 |
| JP | 2013-31429 | 2/2013 |
| JP | 2015-128397 | 7/2015 |
| WO | 2013/003597 | 1/2013 |
| WO | 2014/024998 | 2/2014 |
| WO | 2016/073079 | 5/2016 |

OTHER PUBLICATIONS

Motomura, K. et al. "Overproduction of YjbB reduces the level of . . . " FEMS Microbiology Letters, 2011, vol. 320, pp. 25-32.
Metcalf, W. and Wolfe, R. "Molecular Genetic Analysis of Phosphite . . . " Journal of Bacteriology, 1998, vol. 180, No. 21, pp. 5547-5558.
Lecture Abstracts of Annual Meeting of The Society for Biotechnology, Japan, 2015, vol. 67, p. 319, P-194.
Office Action for JP Patent Application No. 2016-170317, dated Jul. 28, 2020, 14 total pages.
Ryuichi Hirota, Microorganism's metabolism of reduced phosphorus compound . . . , Proceedings of the 11th Annual Meeting of the Society of Genome Microbiology, Japan, 2017, vol. 11, p. 52.
Ryuichi Hirota and Akio Kuroda, Kagaku Kogyo, Selective and Biologically Contained Cultivation System for Microorganism Using Phosphite, vol. 68, Jun. 1, 2017 (Jun. 1, 2017), pp. 429-435, Section 3.
Zen-ichiro Katsuura et al, Characterization of a biologically contained *Escherichia* . . . , Proceedings of the Annual Meeting of the Japan Society for Bioscience, Biotechnology, and Agrochemistry, 2017, 4J30a05.
Ryuichi Hirota et al, A Novel biocontainment strategy makes bacterial growth dependent on phosphite, Proceedings of the Annual Meeting of the Japan Society for Bioscience, Biotechnology, and Agrochemistry, 2017, 6 pages.
Hirota R et al., A Novel Biocontainment Strategy Makes Bacterial Growth and Survival Dependent on Phosphite, Mar. 20, 2017, vol. 7, p. 44748, Abstract.
Atsushi Sakuda et al, Development of a feasible phosphite detection system . . . , Proceedings of the Annual Meeting of the Japan Society for Bioscience, Biotechnology, and Agrochemistry, 2014.
Ryuichi Hirota et al, O-04 Biotechnology using bacterial function . . . , Proceedings of the Annual Meeting of the Japan Society for Environmental Biotechnology, 2016.
Ryuichi Hirota and Akio Kuroda, Biotechnology using reduced phosphorous compound, Enzyme Engineering News, vol. 74, Oct. 2015, pp. 26-31.
Mandell DJ et al., Biocontainment of genetically modified organisms by synthetic protein design, 2015, vol. 518, pp. 55-60, Abstract.
Rovner AJ et al., Recoded organisms engineered to depend on synthetic amino acids, 2015, vol. 518, pp. 89-93, Abstract.
Lauwers AM et al., Alterations of Alkaline Phosphatase Activity during Adaptation of *Escherichia coli* to Phosphite and Hypophosphite, 1977, vol. 112, pp. 103-107, Abstract.

(Continued)

*Primary Examiner* — Albert M Navarro
(74) *Attorney, Agent, or Firm* — Casimir Jones, S.C.; Robert A. Goetz

(57) ABSTRACT

In order to provide a transformant by which a high containment effect is obtained and which can be prepared by a simple procedure, a method for producing the transformant, and a method for detecting the presence of a reduced phosphorous compound with use of the transformant, a transformant in accordance with an embodiment of the present invention is a transformant which is defective in functions of a gene encoding a phosphate transporter protein and a gene encoding a phosphate ester transporter protein and into which a gene encoding a hypophosphite transporter protein is introduced.

12 Claims, 5 Drawing Sheets

Specification includes a Sequence Listing.

(56) References Cited

OTHER PUBLICATIONS

Kanda K et al., Application of a phosphite dehydrogenase gene as a novel . . . , 2014, vol. 182-183, pp. 68-73, Abstract.
Loera-Quezada MM et al., A novel genetic engineering platform for the effective management of biological . . . , Mar. 28, 2016, vol. 14, pp. 2066-2076, Summary.
White AK et al., The htx and ptx Operons and Pseudomonas stutzeri WM88 . . . , 2004, vol. 186, pp. 5876-5882, Abstract.
Metcalf WW et al., Molecular Genetic Analysis of Phosphite and Hypophosphite . . . , 1998, vol. 180, pp. 5547-5558, Abstract.
Wilson MM et al.., Genetic Diversity and Horizontal Transfer of Genes Involved in Oxidation . . . , 2005, vol. 71, pp. 290-296. Abstract.
Ryuichi Hirota et al, Characterization of a bacterial transport system, Proceedings of the Annual Meeting of the Japan Society for Bioscience, Biotechnology, and Agrochemistry, 2016.
English translation of International preliminary report on patentability of PCT/JP2017/027588, dated Mar. 14, 2019, 8 pages.
International Search Report for PCT/JP2017/027588, dated Oct. 24, 2017, 3 pages.
EP Search Report, EP Patent Application No. 17845996.2, dated Jul. 22, 2019, 12 pages.
Wright, O. et al: "Building-in biosafety for synthetic biology", Microbiology, vol. 159, No. Pt, 7, Mar. 21, 2013 (Mar. 21. 2013), pp. 1221-1235, XP05515545.
Motomura, Kei "Synthetic Phosphorus Metabolic Pathway for Biosafety . . . " ACS Synthetic Biology, vol. 7 No. 9, Sep. 11, 2018 pp. 2189-2198 XP055604047.

TRANSFORMANT, METHOD FOR PRODUCING TRANSFORMANT, AND METHOD FOR DETECTING PRESENCE OR ABSENCE OF REDUCED PHOSPHORUS COMPOUND USING TRANSFORMANT

TECHNICAL FIELD

The present invention relates to a transformant, a method for producing the transformant, and a method for detecting the presence of a reduced phosphorous compound with use of the transformant.

BACKGROUND ART

Recently, genetically modified organisms applicable to various uses have been prepared. The genetically modified organisms thus prepared are expected to be used for the purpose of, for example, oral vaccines or improvement of natural environment.

Meanwhile, there are several demands which should be satisfied when genetically modified organisms are actually used. As one of the demands, it is necessary to prepare a genetically modified organism which can proliferate only in a limited place but cannot proliferate outside the limited place (in other words, a genetically modified organism by which a high containment effect is obtained). In the case of such a genetically modified organism, the genetically modified organism cannot proliferate in nature even if the genetically modified organism leaks into nature. Therefore, it is possible to prevent contamination of nature by the genetically modified organism.

Various methods have been developed for preparation of such genetically modified organisms. Examples of the methods encompass: (i) a method in which a gene having toxicity is introduced into an organism and the organism is killed by the toxicity of the gene when a desired time has elapsed (kill switch); and (ii) a method in which a biosynthesis ability for a compound essential for growth of an organism is deleted from the organism, and the organism is allowed to live on only an externally supplied nutrient(s) (auxotrophy).

However, a containment effect obtained by each of the methods (i) and (ii) above is not sufficient. Accordingly, there has been a demand for development of a method by which a higher containment effect can be obtained.

Under such circumstances, a new method has been developed. The new method is (iii) a method in which an organism is made to be auxotrophic for a compound that does not naturally occur (synthetic auxotrophy). Non-Patent Literature 1 is a specific example which discloses the method (iii). Non-Patent Literature 1 discloses a method of preparing *Escherichia coli* (*E. coli*) that can proliferate in an environment where an artificially-synthesized amino acid, which does not naturally occur, is present. In this method, a target *E. coli* is prepared by introducing mutations in many genes of *E. coli*. Then, with the method (iii), for example, even if $10^{11}$ genetically modified organisms leak into nature, the number of the genetically modified organisms which can live in nature will be zero.

CITATION LIST

Non-patent Literature

[Non-Patent Literature 1] Alexis J. Rovner et al., Recoded organisms engineered to depend on synthetic amino acids, Nature, vol. 518, p89-93, 5 February 2015

SUMMARY OF INVENTION

Technical Problem

Though the method (iii) described above can realize a high containment effect, the method has a problem in that preparation of a genetically modified organism is complicated.

Specifically, in the method (iii), it is necessary to introduce defects into all TGA codons in 200 to 300 genes in *E. coli*. Further, in the method (iii), it is necessary to introduce, into the *E. coli*, tRNA, aaRS, and a codon that are associated with artificially-synthesized amino acids which do not naturally occur.

The present invention is attained in view of the above problems, and an object of the present invention is to provide a transformant by which a high containment effect is obtained and which can be prepared by a simple procedure, a method for producing the transformant, and a method for detecting the presence of a reduced phosphorous compound with use of the transformant.

Solution to Problem

In order to solve the above problems, a transformant in accordance with an embodiment of the present invention is a transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation.

In order to solve the above problems, a method for producing a transformant in accordance with an embodiment of the present invention includes the step of: introducing a gene encoding a hypophosphite transporter protein or HtxABCDE protein into a host that is defective in functions of a gene encoding a phosphate transporter protein and a gene encoding a phosphate ester transporter protein.

In order to solve the above problems, a method for detecting the presence of a reduced phosphorous compound in accordance with an embodiment of the present invention includes the steps of: culturing the transformant in accordance with an embodiment of the present invention, with use of a culture medium as a detection target; and detecting whether or not the transformant proliferated in the step of culturing.

Advantageous Effects of Invention

A transformant in accordance with an embodiment of the present invention can be easily prepared by manipulation of a small number of genes. Further, a transformant in accordance with an embodiment of the present invention can be easily prepared by using an existing strain.

A transformant in accordance with an embodiment of the present invention has an ability to take and utilize, in cells, not a naturally-occurring phosphate but a reduced phosphorous compound which does not naturally occur. Accordingly, even in a case where the transformant leaks into nature, the transformant dies in nature where the reduced phosphorous compound is absent. In other words, an embodiment of the present invention can yield a high containment effect.

A transformant in accordance with an embodiment of the present invention causes no emergence of a strain which is capable of growing in a non-permissive culture medium as a result of mutation. Therefore, a high containment effect is obtained by the transformant.

A transformant in accordance with an embodiment of the present invention makes it possible to reduce cost for proliferation of the transformant, since the transformant is cultured by use of an inexpensive reduced phosphorous compound.

A transformant in accordance with an embodiment of the present invention makes it possible to reduce cost for proliferation of the transformant, since the transformant is cultured without use of an expensive antibiotic substance.

Most organisms present in nature do not have an ability to take and utilize a reduced phosphorous compound in cells. Accordingly, culture of a transformant in accordance with an embodiment of the present invention together with organisms present in nature with use of a reduced phosphorous compound makes it possible to prepare a large amount of only transformants in accordance with an embodiment of the present invention while proliferation of organisms present in nature is inhibited.

DESCRIPTION OF EMBODIMENTS

An embodiment of the present invention will be discussed below. Note, however, that the present invention is not limited to such an embodiment. The present invention is not limited to arrangements described below, but can be altered within the scope of the claims. An embodiment or example derived from a combination of technical means disclosed in different embodiments or examples is also encompassed in the technical scope of the present invention. All academic and patent literatures listed herein are incorporated herein by reference. Note that a numerical range "A to B" herein means "not less than A and not more than B" unless otherwise specified in this specification.

1. Basic Principle of Aspect of the Present Invention

In nature, whereas a large amount of phosphate (or phosphate compound) exists, a reduced phosphorous compound (e.g., phosphite and hypophosphite) is absent or if any, only a very small amount of reduced phosphorous compound is present. In this condition, in a case where a transformant, whose proliferation does not depend on phosphate but depends on a reduced phosphorous compound, is prepared, the transformant cannot proliferate in nature even if the transformant leaks into nature. The inventors of the present application arrived at an idea that a high containment effect might be obtained by such a transformant, and drove for preparation of the transformant.

Figure 1:
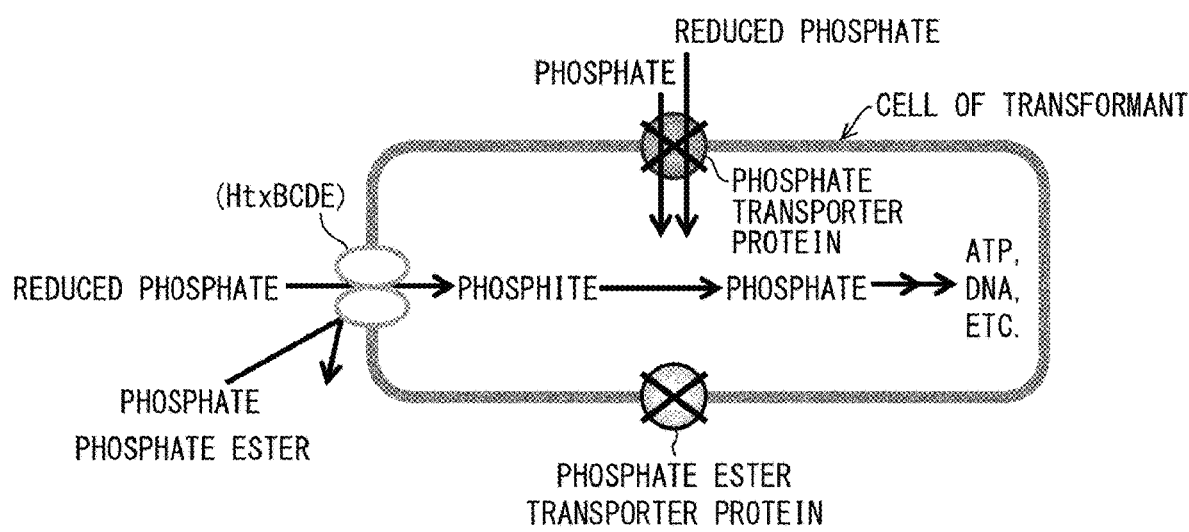
FIG. 1 is a diagram illustrating a basic principle of an aspect of the present invention.

As illustrated in FIG. 1, a phosphate transporter protein and a phosphate ester transporter protein are basically present in organisms.

The phosphate transporter protein is a protein for uptake of phosphate and a reduced phosphorous compound into cells. On the other hand, the phosphate ester transporter protein is a protein for uptake of phosphate ester into cells. Note that when phosphate ester is taken into cells, the phosphate ester is indirectly utilized as a phosphorus source (P source) in a metabolic system of the cells.

If both of the phosphate transporter protein and the phosphate ester transporter protein are present in an organism, phosphate is supplied from nature to cells of the organism. Then, a transformant proliferates in nature dependently on the phosphate. In light of this, the inventors of the present application considered that in a transformant in accordance with an embodiment of the present invention, it is necessary to first make functions of both the phosphate transporter protein and the phosphate ester transporter protein defective in the transformant.

When the functions of both the phosphate transporter protein and the phosphate ester transporter protein are caused to be defective, no phosphate is supplied any longer from nature to cells. Meanwhile, no reduced phosphorous compound is supplied any longer from nature to the cells. In this case, the transformant cannot proliferate dependently on the reduced phosphorous compound.

In light of the above, in order to prepare a transformant dependent on a reduced phosphorous compound as described above, the inventors of the present application first tried to obtain a target transformant by (i) causing a defect in a phosphate transport system and (ii) introducing PtxABC gene which encodes a phosphite transporter protein. However, as a result of studies made by the inventors of the present application, it was revealed that the PtxABC transports phosphate as well as phosphite into cells. This meant that a containment effect is not obtained by the transformant which is defective in a phosphate transport system and into which a phosphite transport system is incorporated. As a result, it became necessary to discover a protein which is defective in an ability to take phosphate and phosphate ester into cells and which has an ability to take only a reduced phosphorous compound into cells. Thereafter, the inventors of the present application newly found that HtxBCDE gene encoding a hypophosphite transporter protein has a function to transport a reduced phosphorous compound (e.g., hypophosphite and phosphite) but no phosphate. Then, the inventors of the present application successfully prepared a transformant incapable of utilizing phosphate but capable of utilizing a reduced phosphorous compound, by causing a defect in a phosphate transport system and introducing HtxBCDE. If the transformant expresses HtxBCDE protein, the transformant can take only a reduced phosphorous compound into cells and the reduced phosphorous compound is converted to phosphate in a metabolic system of cells. Then, the transformant can proliferate by utilizing the phosphate. Further, in a case where HtxA gene encoding a hypophosphite dioxygenase is expressed concurrently with the HtxBCDE gene, hypophosphite taken into cells by the HtxBCDE protein is oxidized by HtxA protein to produce phosphite in the cells. Further, the phosphite is oxidized by PtxD protein to produce phosphate in the cells. The transformant can then proliferate by utilizing the phosphate.

According to the above-described basic principle of an aspect of the present invention, the transformant in accordance with an embodiment of the present invention cannot utilize phosphate for proliferation but can utilize a reduced phosphorous compound (e.g., phosphite and/or hypophosphite) for proliferation, since functions of a gene encoding a phosphate transporter protein and a gene encoding a phosphate ester transporter protein are defective in the transformant and a gene encoding the HtxBCDE protein or the HtxABCDE protein is/are introduced into the transformant. The HtxABCDE gene here is a gene encoding a hypophosphite dioxygenase (HtxA) gene and a hypophosphite transporter (HtxBCDE) gene. The following will discuss an embodiment of the present invention in more details.

2. Transformant in Accordance with Embodiment of the Present Invention

The transformant in accordance with an embodiment of the present invention is a transformant which is defective in the functions of the gene encoding a phosphate transporter protein and the gene encoding a phosphate ester transporter protein, and into which the gene encoding a hypophosphite transporter protein (e.g., HtxBCDE protein) or encoding the HtxABCDE protein is introduced. Accordingly, the transformant in accordance with an embodiment of the present invention cannot utilize phosphate for proliferation but can utilize a reduced phosphorous compound (e.g., phosphite and/or hypophosphite) for proliferation.

More specifically, in a case where the transformant in accordance with the present embodiment cannot utilize phosphate for proliferation but can utilize phosphite for proliferation, the gene encoding a hypophosphite transporter protein (e.g., HtxBCDE protein) may be introduced in the transformant. In contrast, in a case where the transformant in accordance with an embodiment of the present invention cannot utilize phosphate for proliferation but can utilize hypophosphite for proliferation, the gene encoding the HtxABCDE protein may be introduced in the transformant. Of course, in a case where the transformant in accordance with the present embodiment cannot utilize phosphate for proliferation but can utilize phosphite for proliferation, the gene encoding the HtxABCDE protein can be introduced in the transformant.

Examples of a host of the transformant in accordance with the present embodiment encompass *E. coli*, lactic acid bacteria, photosynthetic bacteria, and plants. The host is of course not limited to these examples. A transformant in accordance with an embodiment of the present invention can be prepared by manipulation of a small number of genes. Therefore, any organism (e.g., microorganism) can be the host.

In the transformant in accordance with the present embodiment, the gene encoding a hypophosphite transporter protein (e.g., HtxBCDE protein) or the gene encoding the HtxABCDE protein is introduced. Note that the gene encoding the HtxBCDE protein and the gene encoding the HtxABCDE protein may be each a gene derived from Pseudomonas stutzeri WM88.

More specifically, the HtxABCDE protein can be a protein consisting of a protein encoded by a gene consisting of any one of the following polynucleotides (1) to (3) or a protein including, as at least part thereof, the protein encoded by the gene consisting of any one of the following polynucleotides (1) to (3):

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity; and (3) a polynucleotide (i) consisting of a polynucleotide having a sequence identity of not less than 90% relative to the polynucleotide consisting of the base sequence of SEQ ID NO: 24 and (ii) encoding a protein which does not have phosphate transport activity but which has reduced phosphorous compound transport activity.

Meanwhile, the HtxBCDE protein can be (i) a protein consisting of a protein which is encoded by a gene consisting of any one of the following polynucleotides (1) to (3) and from which HtxA protein is excluded, or (ii) a protein including, as at least part thereof, the protein which is encoded by the gene consisting of any one of the following polynucleotides (1) to (3) and from which HtxA protein is excluded:

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity; and (3) a polynucleotide (i) consisting of a polynucleotide having a sequence identity of not less than 90% relative to the polynucleotide consisting of the base sequence of SEQ ID NO: 24 and (ii) encoding a protein which does not have phosphate transport activity but which has reduced phosphorous compound transport activity.

Whether a protein is defective in phosphate transport activity and has reduced phosphorous compound transport activity can be checked by (i) introducing a gene encoding a chosen protein in an expressible manner into an organism that is defective in the functions of the gene encoding a phosphate transporter protein and the gene encoding a phosphate ester transporter protein and (ii) causing the organism to proliferate in culture media containing various phosphorus sources. If the organism proliferates in a culture medium containing a reduced phosphorous compound but does not proliferate in a culture medium containing phosphate, it can be determined that the above protein is defective in phosphate transport activity and has reduced phosphorous compound transport activity.

The polynucleotide (3) above preferably has a higher sequence identity. The sequence identity of the polynucleotide can be, for example, not less than 91%, not less than 92%, not less than 93%, not less than 94%, not less than 95%, not less than 96%, not less than 97%, not less than 98% or not less than 99%. Note that the sequence identity of polynucleotides can be calculated by using GENETYX-WIN (product name, manufactured by Genetyx Corporation) according to a manual of the product.

The transformant in accordance with an embodiment of the present invention is defective in the functions of the gene encoding a phosphate transporter protein and the gene encoding a phosphate ester transporter protein. The term "phosphate transporter protein" herein means a protein which has activity to take both phosphate and a reduced phosphorous compound into cells. On the other hand, the term "phosphate ester transporter protein" herein means a protein which has activity to take phosphate ester into cells.

In this case, the transformant, which is defective in the functions of the gene encoding a phosphate transporter protein and the gene encoding a phosphate ester transporter protein, can be prepared by artificially mutating a host. Alternatively, the transformant may be prepared by using a host which originally has neither of the functions of the gene encoding a phosphate transporter protein and the gene encoding a phosphate ester transporter protein (e.g., a host having a genome in which both the gene encoding a phosphate transporter protein and the gene encoding a phosphate ester transporter protein are absent, or a host which expresses neither a phosphate transporter protein nor a phosphate ester transporter protein).

Different types of phosphate transporter protein and different types of phosphate ester transporter protein exist in cells of different species of organism. Therefore, there is no limitation to particular types of phosphate transporter protein and phosphate ester transporter protein which have functions defective in the transformant in accordance with the present embodiment. It is possible to determine as appropriate, depending on a host, the gene encoding a phosphate transporter protein and the gene encoding a phosphate ester transporter protein, which genes have functions that are caused to be defective in the host.

For example, in a case where the host of the transformant is *E. coli*, the phosphate transporter protein can be at least one selected from the group consisting of PitA protein, PitB protein, PstSCAB protein, and PhnCDE protein.

More specifically, the PitA protein can be a protein consisting of the following protein (4) or (5), a protein including, as at least part thereof, the following protein (4) or (5), a protein consisting of a protein encoded by a gene consisting of the following polynucleotide (6) or (7), or a protein including, as at least part thereof, the protein encoded by the gene consisting of the following polynucleotide (6) or (7):
(4) a protein consisting of the amino acid sequence of SEQ ID NO: 2;
(5) a protein (i) consisting of an amino acid sequence obtained by deletion, substitution, or addition of one or several amino acids in the amino acid sequence of SEQ ID NO: 2 and (ii) having phosphate transport activity;
(6) a polynucleotide consisting of the base sequence of SEQ ID NO: 1; or
(7) a polynucleotide (i) being hybridizable, under a stringent condition, with DNA consisting of a base sequence complementary to the base sequence of SEQ ID NO: 1, and (ii) encoding a protein which has phosphate transport activity.

The PitB protein can be a protein consisting of the following protein (8) or (9), a protein including, as at least part thereof, the following protein (8) or (9), a protein consisting of a protein encoded by a gene consisting of the following polynucleotide (10) or (11), or a protein including, as at least part thereof, the protein encoded by the gene consisting of the following polynucleotide (10) or (11):
(8) a protein consisting of the amino acid sequence of SEQ ID NO: 4;
(9) a protein (i) consisting of an amino acid sequence obtained by deletion, substitution, or addition of one or several amino acids in the amino acid sequence of SEQ ID NO: 4 and (ii) having phosphate transport activity;
(10) a polynucleotide consisting of the base sequence of SEQ ID NO: 3; or
(11) a polynucleotide (i) being hybridizable, under a stringent condition, with DNA consisting of a base sequence complementary to the base sequence of SEQ ID NO: 3, and (ii) encoding a protein which has phosphate transport activity.

The PstSCAB protein can be a protein consisting of a protein encoded by a gene consisting of the following polynucleotide (12) or (13), or a protein including, as at least part thereof, the protein encoded by the gene consisting of the following polynucleotide (12) or (13):
(12) a polynucleotide consisting of the base sequence of SEQ ID NO: 23; or
(13) a polynucleotide (i) being hybridizable, under a stringent condition, with DNA consisting of a base sequence complementary to the base sequence of SEQ ID NO: 23, and (ii) encoding a protein which has phosphate transport activity.

The PhnCDE protein can be a protein consisting of a protein encoded by a gene consisting of the following polynucleotide (14) or (15) or a protein including, as at least part thereof, the protein encoded by the gene consisting of the following polynucleotide (14) or (15):
(14) a polynucleotide consisting of the base sequence of SEQ ID NO: 11; or
(15) a polynucleotide (i) being hybridizable, under a stringent condition, with DNA consisting of a base sequence complementary to the base sequence of SEQ ID NO: 11, and (ii) encoding a protein which has phosphate transport activity.

Whether a protein has phosphate transport activity can be checked by (i) introducing a gene encoding a chosen protein in an expressible manner into an organism that is defective in the functions of the gene encoding a phosphate transporter protein and the gene encoding a phosphate ester transporter protein and (ii) causing the organism to proliferate in culture media containing various phosphorus sources. If the organism proliferates in a culture medium containing phosphate, it can be determined that the above protein has phosphate transport activity.

In a case where the host of the transformant is *E. coli*, the phosphate ester transporter protein can be at least one selected from the group consisting of UhpT protein, UgpB protein, and GlpT protein.

More specifically, the UhpT protein can be a protein consisting of the following protein (16) or (17), a protein including, as at least part thereof, the following protein (16) or (17), a protein consisting of a protein encoded by a gene consisting of the following polynucleotide (18) or (19), or a protein including, as at least part thereof, the protein encoded by the gene consisting of the following polynucleotide (18) or (19):
(16) a protein consisting of the amino acid sequence of SEQ ID NO: 38;
(17) a protein (i) consisting of an amino acid sequence obtained by deletion, substitution, or addition of one or several amino acids in the amino acid sequence of SEQ ID NO: 38 and (ii) having phosphate ester transport activity;
(18) a polynucleotide consisting of the base sequence of SEQ ID NO: 37; or
(19) a polynucleotide (i) being hybridizable, under a stringent condition, with DNA consisting of a base sequence complementary to the base sequence of SEQ ID NO: 37, and (ii) encoding a protein which has phosphate ester transport activity.

The UgpB protein can be a protein consisting of the following protein (20) or (21), a protein including, as at least part thereof, the following protein (20) or (21), a protein consisting of a protein encoded by a gene consisting of the following polynucleotide (22) or (23), or a protein including, as at least part thereof, the protein encoded by the gene consisting of the following polynucleotide (22) or (23):

(20) a protein consisting of the amino acid sequence of SEQ ID NO: 40;

(21) a protein (i) consisting of an amino acid sequence obtained by deletion, substitution, or addition of one or several amino acids in the amino acid sequence of SEQ ID NO: 40 and (ii) having phosphate ester transport activity;

(22) a polynucleotide consisting of the base sequence of SEQ ID NO: 39; or

(23) a polynucleotide (i) being hybridizable, under a stringent condition, with DNA consisting of a base sequence complementary to the base sequence of SEQ ID NO: 39, and (ii) encoding a protein which has phosphate ester transport activity.

The GlpT protein can be a protein consisting of the following protein (24) or (25), a protein including, as at least part thereof, the following protein (24) or (25), a protein consisting of a protein encoded by a gene consisting of the following polynucleotide (26) or (27), or a protein including, as at least part thereof, the protein encoded by the gene consisting of the following polynucleotide (26) or (27):

(24) a protein consisting of the amino acid sequence of SEQ ID NO: 42;

(25) a protein (i) consisting of an amino acid sequence obtained by deletion, substitution, or addition of one or several amino acids in the amino acid sequence of SEQ ID NO: 42 and (ii) having phosphate ester transport activity;

(26) a polynucleotide consisting of the base sequence of SEQ ID NO: 41; or

(27) a polynucleotide (i) being hybridizable, under a stringent condition, with DNA consisting of a base sequence complementary to the base sequence of SEQ ID NO: 41, and (ii) encoding a protein which has phosphate ester transport activity.

Whether a protein has phosphate ester transport activity can be checked by (i) introducing a gene encoding a chosen protein in an expressible manner into an organism that is defective in the functions of the gene encoding a phosphate transporter protein and the gene encoding a phosphate ester transporter protein and (ii) causing the organism to proliferate in culture media containing various phosphorus sources. If the organism proliferates in a culture medium containing phosphate ester, it can be determined that the above protein has phosphate ester transport activity.

In the transformant in accordance with an embodiment of the present invention, a gene encoding a phosphite dehydrogenase protein can be further introduced. In this configuration, the reduced phosphorous compound taken into cells can be efficiently converted to phosphate. This allows the transformant in accordance with an embodiment of the present invention to proliferate better dependently on the reduced phosphorous compound.

The gene encoding a phosphite dehydrogenase protein can be a gene derived from Pseudomonas stutzeri WM88 (e.g., PtxD gene).

More specifically, the phosphite dehydrogenase protein can be a protein consisting of the following protein (28) or (29), a protein including, as at least part thereof, the following protein (28) or (29), a protein consisting of a protein encoded by a gene consisting of the following polynucleotide (30) or (31), or a protein including, as at least part thereof, the protein encoded by the gene consisting of the following polynucleotide (30) or (31):

(28) a protein consisting of the amino acid sequence of SEQ ID NO: 15;

(29) a protein (i) consisting of an amino acid sequence obtained by deletion, substitution, or addition of one or several amino acids in the amino acid sequence of SEQ ID NO: 15 and (ii) having phosphite dehydrogenase activity;

(30) a polynucleotide consisting of the base sequence of SEQ ID NO: 14; or

(31) a polynucleotide (i) being hybridizable, under a stringent condition, with DNA consisting of a base sequence complementary to the base sequence of SEQ ID NO: 14, and (ii) encoding a protein which has phosphite dehydrogenase activity.

Whether a protein has phosphite dehydrogenase activity can be checked on the basis of whether or not the protein produces $HPO_4^{2-}$ by $NADP^+$ dependently or $NADP^+$ dependently oxidizing phosphite. More specifically, it can be determined that a chosen protein has phosphite dehydrogenase activity, if $HPO_4^{2-}$ is produced after the chosen protein, $HPO_3^{2-}$, and $NAD^+$ or $NADP^+$ are mixed together.

The transformant in accordance with an embodiment of the present invention can further be defective in a function of a gene encoding an alkaline phosphatase protein (e.g., PhoA gene). The alkaline phosphatase protein acts to convert, to phosphate, phosphite which is present outside the cells, and to thereby decrease a phosphite concentration outside the cells. The transformant defective in the function of the gene encoding an alkaline phosphatase protein can keep the phosphite concentration outside the cells high. Accordingly, with this configuration, an amount of the reduced phosphorous compound taken into cells can be increased. This consequently allows the transformant in accordance with an embodiment of the present invention to grow better dependently on the reduced phosphorous compound.

Different types of alkaline phosphatase protein exist in cells of different species of organism. Therefore, there is no limitation to a particular type of alkaline phosphatase protein which has a function defective in the transformant in accordance with the present embodiment. It is possible to determine as appropriate, depending on a host, the gene encoding an alkaline phosphatase protein, which gene has a function that is caused to be defective in the host.

For example, in a case where the host of the transformant is E. coli, the alkaline phosphatase protein can be a protein consisting of the following protein (32) or (33), a protein including, as at least part thereof, the following protein (32) or (33), a protein consisting of a protein encoded by a gene consisting of the following polynucleotide (34) or (35), or a protein including, as at least part thereof, the protein encoded by the gene consisting of the following polynucleotide (34) or (35):

(32) a protein consisting of the amino acid sequence of SEQ ID NO: 13;

(33) a protein (i) consisting of an amino acid sequence obtained by deletion, substitution, or addition of one or several amino acids in the amino acid sequence of SEQ ID NO: 13 and (ii) having an alkaline phosphatase activity;

(34) a polynucleotide consisting of the base sequence of SEQ ID NO: 12; or

(35) a polynucleotide (i) being hybridizable, under a stringent condition, with DNA consisting of a base sequence complementary to the base sequence of SEQ ID NO: 12, and (ii) encoding a protein which has an alkaline phosphatase activity.

Whether a protein has an alkaline phosphatase activity can be checked on the basis of whether the protein converts phosphite to phosphate. More specifically, it can be determined that a chosen protein has an alkaline phosphatase activity, if phosphate is produced after the chosen protein and phosphite are mixed together.

With regard the wording "an amino acid sequence obtained by deletion, substitution, or addition of one or several amino acids", a position where one or several amino acids are deleted, substituted or added is not particularly limited.

Further, the number of amino acids intended by the wording "one or several amino acids" is not particularly limited, and can be not more than 50, not more than 40, not more than 30, not more than 20, not more than 19, not more than 18, not more than 17, not more than 16, not more than 15, not more than 14, not more than 13, not more than 12, not more than 11, not more than 10, not more than 9, not more than 8, not more than 7, not more than 6, not more than 5, not more than 4, not more than 3, not more than 2, or not more than 1.

It is preferable that the substitution of an amino acid be a conservative substitution. Note that the term "conservative substitution" refers to a substitution of a particular amino acid by another amino acid having a chemical property and/or a structure that is/are similar to that/those of the particular amino acid. Examples of the chemical property include a degree of hydrophobicity (hydrophobicity and hydrophilicity) and electric charge (neutrality, acidity, and basicity). Examples of the structure include an aromatic ring, an aliphatic hydrocarbon group, and a carboxyl group, which are present as a side chain or as a functional group of a side chain.

Examples of the conservative substitution include a substitution between serine and threonine, a substitution between lysine and arginine, and a substitution between phenylalanine and triptophan. The substitution in an embodiment of the present invention is, of course, not limited to the above-described substitutions.

The term "stringent condition" as used herein refers to a condition under which a so-called base sequence specific double-stranded polynucleotide is formed whereas a base-sequence non-specific double-stranded polynucleotide is not formed. In other words, the "stringent condition" can be expressed as a condition under which hybridization is carried out at a temperature in a range from (i) a melting temperature (Tm) of nucleic acids having a high homology (e.g., a perfectly-matched hybrid) to (ii) 15° C. lower than the melting temperature (Tm), preferably 10° C. lower than the melting temperature (Tm), further preferably 5° C. lower than the melting temperature (Tm).

In one example of the stringent condition, hybridization can be carried out in a buffer solution (including 0.25M $Na_2HPO_4$, pH 7.2, 7% SDS, 1 mM EDTA, and 1×Denhardt's solution) for 16 hours to 24 hours at a temperature in a range from 60° C. to 68° C., preferably at 65° C., further preferably at 68° C., and then washing can be carried out twice in a buffer solution (including 20 mM $Na_2HPO_4$, pH 7.2, 1% SDS, and 1 mM EDTA) for 15 minutes at a temperature in a range from 60° C. to 68° C., preferably at 65° C., further preferably at 68° C.

In another example, prehybridization is carried out overnight at 42° C. in a hybridization solution (including 25% formamide or 50% formamide (for a severer condition), 4×SSC (sodium chloride/sodium citrate), 50 mM Hepes pH 7.0, 10×Denhardt's solution, and 20 µg/ml denatured salmon sperm DNA), and then hybridization is carried out by adding a labeled probe thereto and keeping a resulting solution at 42° C. overnight. In washing following the hybridization, conditions for a washing solution and a temperature are approximately "1×SSC, 0.1% SDS, 37° C.", approximately "0.5×SSC, 0.1% SDS, 42° C." for a severer condition, approximately "0.2×SSC, 0.1% SDS, 65° C." for a further severer condition. As such, as the conditions for the washing following the hybridization become severer, the specificity of hybridization becomes higher. However, the above-indicated combinations of conditions on SSC, SDS, and temperature are merely examples. A person skilled in the art can provide a stringency similar to the above by appropriately combining the above-described or other elements (e.g., a probe concentration, a probe length, and a time period for a hybridization reaction) that determine the stringency of hybridization. This is disclosed in, for example, Sambrook et al., Molecular Cloning, A Laboratory Manual, 3rd Ed., Cold Spring Harbor Laboratory (2001).

3. Method for Producing Transformant

A method for producing a transformant in accordance with the present embodiment includes the step of introducing a gene encoding a hypophosphite transporter protein (e.g., HtxBCDE protein) or a gene encoding HtxABCDE protein into a host which is defective in functions of a gene encoding a phosphate transporter protein and a gene encoding a phosphate ester transporter protein.

Note that in the method for producing the transformant in accordance with the present embodiment, a configuration described in [2. Transformant in accordance with embodiment of the present invention] above is applicable here. For example, the method for producing the transformant in accordance with the present embodiment can be configured as below. More details of a configuration described below were described in [2. Transformant in accordance with embodiment of the present invention] above, and description thereof is therefore omitted here.

In the method for producing the transformant in accordance with the present embodiment, the HtxABCDE protein can be a protein consisting of a protein encoded by a gene consisting of any one of the following polynucleotides (1) to (3) or a protein including, as at least part thereof, the protein encoded by the gene consisting of any one of the following polynucleotides (1) to (3):

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity; and (3) a polynucleotide (i) consisting of a polynucleotide having a sequence identity of not less than 90% relative to the polynucleotide consisting of the base sequence of SEQ ID NO: 24 and (ii) encoding a protein which does not have phosphate transport activity but which has reduced phosphorous compound transport activity.

Meanwhile, the HtxBCDE protein can be (i) a protein consisting of a protein which is encoded by a gene consisting of any one of the following polynucleotides (1) to (3) and from which HtxA protein is excluded, or (ii) a protein including, as at least part thereof, the protein which is encoded by the gene consisting of any one of the following polynucleotides (1) to (3) and from which HtxA protein is excluded:

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity; and (3) a polynucleotide (i) consisting of a polynucleotide having a sequence identity of not less than 90% relative to the polynucleotide consisting of the base sequence of SEQ ID NO: 24 and (ii) encoding a protein which does not have phosphate transport activity but which has reduced phosphorous compound transport activity.

The method for producing the transformant in accordance with the present embodiment can be configured to further include the step of introducing a gene encoding a phosphite dehydrogenase protein.

The method for producing the transformant in accordance with the present embodiment can be configured such that the host is defective in a function of a gene encoding an alkaline phosphatase protein.

The method for producing the transformant in accordance with the present embodiment can be configured such that the host is *E. coli*.

The method for producing the transformant in accordance with the present embodiment can be configured such that the phosphate transporter protein is at least one selected from the group consisting of PitA protein, PitB protein, PstSCAB protein, and PhnCDE protein.

The method for producing the transformant in accordance with the present embodiment can be configured such that the phosphate ester transporter protein is at least one selected from the group consisting of UhpT protein, UgpB protein, and GlpT protein.

4. Method for Detecting Presence of Reduced Phosphorus Compound

A method for detecting the presence of a reduced phosphorous compound in accordance with the present embodiment includes the steps of: culturing the transformant in accordance with an embodiment of the present invention, with use of a culture medium as a detection target; and detecting whether or not the transformant proliferated in the step of culturing.

In the method for detecting the presence of a reduced phosphorous compound in accordance with the present embodiment, it can be determined that a reduced phosphorous compound is contained in the culture medium as the detection target if the transformant proliferated in the step of culturing. In contrast, in the method, it can be determined that no reduced phosphorous compound is contained in the culture medium as the detection target if the transformant did not proliferate in the step of culturing.

Ingredients and form of the culture medium as a detection target is not particularly limited. For example, the form of the culture medium as a detection target can be a liquid form or a solid form.

In a case where the culture medium as a detection target is in the liquid form, whether or not the transformant proliferated in the step of culturing can be detected in the step of detecting, by measuring for example, turbidity (e.g., OD600) of the culture medium. In contrast, in a case where the culture medium as a detection target is in the solid form, whether or not the transformant proliferated in the step of culturing can be detected in the step of detecting, by confirming the presence of colonies of the transformant, which are formed on the culture medium in the solid form.

The reduced phosphorous compound to be detected by the method for detecting in accordance with the present embodiment is not particularly limited. Examples of the reduced phosphorous compound encompass phosphite, hypophosphite, and phosphonate.

The present invention can also be configured as follows.

In order to solve the above problems, a transformant in accordance with an embodiment of the present invention is a transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation.

It is preferable that the hypophosphite transporter protein be HtxBCDE protein and be (i) a protein consisting of a protein which is encoded by a gene consisting of any one of the following polynucleotides (1) to (3) and from which HtxA protein is excluded, or (ii) a protein including, as at least part thereof, the protein which is encoded by the gene consisting of any one of the following polynucleotides (1) to (3) and from which HtxA protein is excluded:

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity; and (3) a polynucleotide (i) consisting of a polynucleotide having a sequence identity of not less than 90% relative to the polynucleotide consisting of the base sequence of SEQ ID NO: 24 and (ii) encoding a protein which does not have phosphate transport activity but which has reduced phosphorous compound transport activity.

It is preferable that in the transformant in accordance with an embodiment of the present invention, a gene encoding a phosphite dehydrogenase protein be further introduced.

The transformant in accordance with an embodiment of the present invention is preferably configured to be defective in a function of a gene encoding an alkaline phosphatase protein.

The transformant in accordance with an embodiment of the present invention is preferably configured to be a transformant of *E. coli*.

The transformant in accordance with an embodiment of the present invention is preferably configured such that: the phosphate transporter protein is at least one selected from the group consisting of PitA protein, PitB protein, PstSCAB protein, and PhnCDE protein.

The transformant in accordance with an embodiment of the present invention is preferably configured such that the phosphate ester transporter protein is at least one selected from the group consisting of UhpT protein, UgpB protein, and GlpT protein.

In order to solve the above problems, a transformant in accordance with an embodiment of the present invention is a transformant which is defective in functions of a gene encoding a phosphate transporter protein and a gene encoding a phosphate ester transporter protein and into which a gene encoding HtxABCDE protein (i.e., gene encoding HtxA protein which is a hypophosphite dioxygenase and HtxABCDE protein which is a hypophosphite transporter protein) is introduced, the transformant being incapable of utilizing phosphate for proliferation but capable of utilizing hypophosphite for proliferation.

In order to solve the above problems, a method for producing a transformant in accordance with an embodiment of the present invention includes the step of: introducing a gene encoding a hypophosphite transporter protein or HtxABCDE protein into a host that is defective in functions of a gene encoding a phosphate transporter protein and a gene encoding a phosphate ester transporter protein.

In order to solve the above problems, a method for detecting the presence of a reduced phosphorous compound in accordance with an embodiment of the present invention includes the steps of: culturing the transformant in accordance with an embodiment of the present invention, with use of a culture medium as a detection target; and detecting whether or not the transformant proliferated in the step of culturing.

The method for detecting the presence of a reduced phosphorous compound in accordance with an embodiment of the present invention is preferably configured such that: the reduced phosphorous compound is phosphonate.

EXAMPLES

Amino Acid Sequences and Base Sequences of Proteins Used in Examples

Table 1 below shows how amino acid sequences and base sequences of proteins, which are used in Examples, correspond to SEQ ID NOs.

TABLE 1

| GENE (ORIGIN) | BASE SEQUENCE | AMINO ACID SEQUENCE |
|---|---|---|
| PitA (*E. coli*) | SEQ ID NO: 1 | SEQ ID NO: 2 |
| PitB (*E. coli*) | SEQ ID NO: 3 | SEQ ID NO: 4 |
| PhnC (*E. coli*) | SEQ ID NO: 5 | SEQ ID NO: 6 |
| PhnD (*E. coli*) | SEQ ID NO: 7 | SEQ ID NO: 8 |
| PhnE (*E. coli*) | SEQ ID NO: 9 | SEQ ID NO: 10 |
| PhnCDE operon (*E. coli*) | SEQ ID NO: 11 | — |
| PhoA (*E. coli*) | SEQ ID NO: 12 | SEQ ID NO: 13 |
| PtxD (*Ralstonia* sp. 4506) | SEQ ID NO: 14 | SEQ ID NO: 15 |
| PtxA (*Ralstonia* sp. 4506) | SEQ ID NO: 16 | SEQ ID NO: 17 |
| PtxB (*Ralstonia* sp. 4506) | SEQ ID NO: 18 | SEQ ID NO: 19 |
| PtxC (*Ralstonia* sp. 4506) | SEQ ID NO: 20 | SEQ ID NO: 21 |
| PtxABCD operon (*Ralstonia* sp. 4506) | SEQ ID NO: 22 | — |
| pstSCAB operon (*E. coli*) | SEQ ID NO: 23 | — |
| HtxABCDE operon (*Pseudomonas stutzeri* WM88) | SEQ ID NO: 24 | — |
| UhpT (*E. coli*) | SEQ ID NO: 37 | SEQ ID NO: 38 |
| UgpB (*E. coli*) | SEQ ID NO: 39 | SEQ ID NO: 40 |
| GlpT (*E. coli*) | SEQ ID NO: 41 | SEQ ID NO: 42 |

Example 1. Analysis of Phosphate Transporters of Bacteria

It is known that in *E. coli*, there are four phosphate transporter proteins including PitA, PitB, PstSCAB, and PhnCDE. As a strain in which genes encoding the above-described four phosphate transporter proteins and a gene encoding phoA protein are disrupted, MT2012 strain (ΔpitA, ΔpitB, ΔphnC, ΔpstSCABphoU, ΔphoA) has been previously prepared (Motomura, K. et al. Overproduction of YjbB reduces the level of polyphosphate in *Escherichia coli*: a hypothetical role of YjbB in phosphate export and polyphosphate accumulation. FEMS microbiology letters 320, 25-32, 2011).

MT2012 strain maintains an ability to transport a phosphate ester compound. Accordingly, MT2012 strain can proliferate in a synthetic culture medium by utilizing a phosphate ester compound as a phosphorus source but cannot proliferate by utilizing phosphate or a reduced phosphorous compound (e.g., phosphite) as a phosphorus source. The above nature was utilized for analysis of a transport ability of the phosphate transporter protein of bacteria.

In order that MT2012 strain could have an increased oxidative activity for phosphite, ptxD/pSTV was introduced into the MT2012 strain. The ptxD/pSTV is a plasmid obtained by cloning, in pSTV, PtxD gene derived from *Ralstonia* sp. 4506. As a result, MT2012-ptxD strain was prepared.

Into each MT2012-ptxD strain, a plasmid in which a gene encoding one of various phosphate transporter proteins or of various phosphite transporter proteins was cloned was introduced. A phosphate transporter protein ability to transport phosphates and a phosphite transporter protein ability to transport phosphites were each studied by examining proliferation of the above MT2012-ptxD strain in a MOPS-phosphate (Pi) liquid medium or a MOPS-phosphite (Pt) liquid medium (respective phosphorus concentrations of these liquid media were 1.0 mM).

Note that the ptxD/pSTV and the plasmid, in which the gene encoding the phosphate transporter protein were cloned, were prepared as described below.

From *E. coli* MG1655 strain, a gene encoding pitA protein, a gene encoding pitB protein, and a gene encoding phnCDE protein were obtained by PCR. Meanwhile, a gene encoding ptxABC protein and a gene encoding ptxD protein were obtained by PCR from *Ralstonia* sp. 4506 strain. DNA fragments thus obtained by the above PCRs were each cloned at an EcoRI/BamHI site of each of pMW118 and pSTV28. Further, the ptxD was also cloned in pTWV229DPlac-Ptac4071. Meanwhile, to SmaI site of this plasmid, a DNA fragment obtained by PCR was ligated by using an In-Fusion HD cloning kit.

A gene encoding HtxABCDE protein was obtained by PCR from Pseudomonas stutzeri WM88 strain. That DNA fragment thus obtained by the PCR was cloned at an EcoRI/BamHI site of each of pMW118 and pSTV28. For ligation of the DNA fragment to a plasmid, the In-Fusion HD cloning kit was used.

Primer sequences used in the above PCRs were as follows. Note that a DNA sequence in lower-case letters means a sequence for addition of a restriction enzyme digestion site. Note also that 15 bases at a 5' end of each of htxABCDE-fw and htxABCDE-rv (described below) indicate a 15 bp additional sequence necessary for reaction with use of the In-Fusion HD cloning kit.

pitA-fw:
(SEQ ID NO: 25)
5'-aagaattcATGCTACATTTGTTTGCTGGC-3';

pitA-rv:
(SEQ ID NO: 26)
5'-aaatctagaTTACAGGAACTGCAAGGAGAG-3';

pitB-fw:
(SEQ ID NO: 27)
5'-aagaattcATGCTAAATTTATTTGTTGGC-3';

pitB-rv:
(SEQ ID NO: 28)
5'-aaatctagaTTAAATCAACTGCAATGCTATC-3';

-continued phnCDE-fw:
(SEQ ID NO: 29)
5'-aagaattcATGCAAACGATTATCCGTGTCGAG-3';

phnCDE-rv:
(SEQ ID NO: 30)
5'-aaatctagaTCAGATAAAGTGCTTACGCAACC-3';

ptxABC-fw:
(SEQ ID NO: 31)
5'-aagaattcTAGCAGGCGTCTATATTTGGCATAG-3';

ptxABC-rv:
(SEQ ID NO: 32)
5'-gctctagaGCTTTGGGAGTTATTTGAACTTGCG-3';

ptxD-fw:
(SEQ ID NO: 33)
5'-aagaattcAATCGGGTTCGAGCTGATGGGCTC-3';

ptxD-rv:
(SEQ ID NO: 34)
5'-aaatctagaTCGCCACACGCTCCAGATCTATCAC-3';

htxABCDE-fw:
(SEQ ID NO: 35)
5'-cggtacccggggatcCTAGGAGCATCACCATGTTTGCAGAGC-3';

htxABCDE-rv:
(SEQ ID NO: 36)
5'-cggtacccggggatcTCAGATCAGCTTGGCGCGGATGCGCGCCTG-3';

ptxDpTWV-fw:
(SEQ ID NO: 43)
5'-cacaaggagactgccATGAAGCCCAAAGTCGTCCTC-3';
and ptxDpTWV-rv:
(SEQ ID NO: 44)
5'-cagtttatggcgggcTCACGCCGCCTTTACTCCCGG-3';

A plasmid in which a gene encoding pstSCAB protein was cloned was prepared by cloning, at an EcoRI/HindIII site of pMW118, a DNA fragment obtained from pEP02 (Kato J. et al., Genetic Improvement of *Escherichia coli* for Enhanced Biological Removal of Phosphate from Wastewater. Applied and Environmental Microbiology 59, 3744-3749, 1993) by EcoRI/HindIII digestion.

Respective plasmids prepared as above were designated as pitA/pMW, pitB/pMW, phnCDE/pMW, pstSCAB/pMW, ptxABC/pMW, htxABCDE/pMW, and htxABCDE/pSTV.

These plasmids were each used to transform MT2012-ptxD strain. Each transformant thus obtained was inoculated in each of the MOPS-phosphate (Pi) liquid medium and the MOPS-phosphite (Pt) liquid medium, and then, a turbidity (OD600) was measured over time. The proliferation of the bacteria was thus examined.

Figure 2:
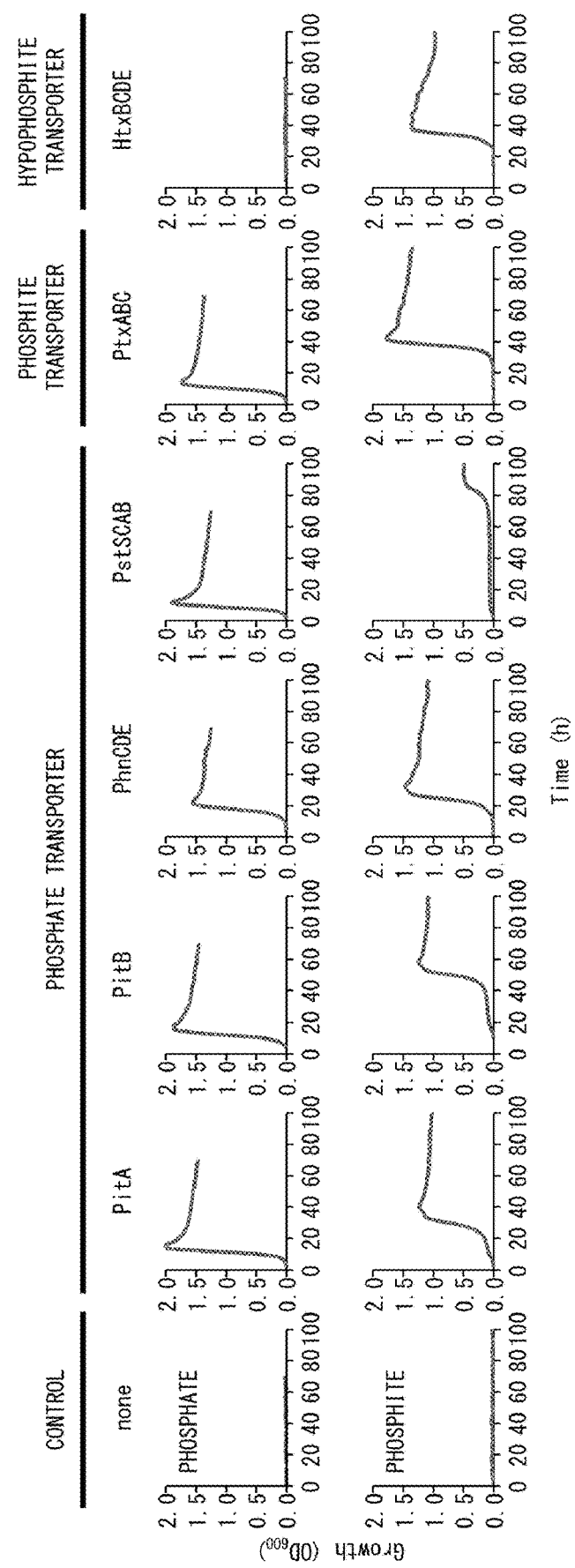
FIG. 2 shows graphs indicative of respective uptake abilities of a phosphate transporter protein, a phosphite transporter protein, and a hypophosphite transporter protein, for uptake of each of phosphate and a reduced phosphorous compound into cells, in an Example of the present invention.

FIG. 2 shows test results. Note that FIG. 2 shows changes over time in turbidity of the bacteria each containing the plasmid in which one of phosphate transporters (PitA, PitB, PhnCDE, and PstSCAB), a phosphite transporter (PtxABC), and a hypophosphite transporter (HtxBCDE) was cloned, in this order from the left of FIG. 2. It was clarified in FIG. 2 that only *E. coli* in which htxBCDE is introduced can grow dependently on a reduced phosphorous compound but cannot grow dependently on phosphate. This indicates that the HtxBCDE protein can specifically take a reduced phosphorous compound into cells.

Example 2. Preparation of Strain Auxotrophic for Phosphite

*E. coli* has phosphate ester transporter proteins (specifically, GlpT, UgpB, and UhpT) for transporting phosphate esters (such as glucose 6-phosphate or glycerol 3-phosphate) in addition to phosphate transporter proteins (specifically, PitA protein, PitB protein, PstSCAB protein, and PhnCDE protein) for transporting inorganic phosphates. Accordingly, *E. coli* can utilize a phosphate ester compound as a phosphorus source to grow.

Further, an alkaline phosphatase protein (specifically, PhoA protein), which is a periplasmic enzyme of *E. coli*, is known to have a weak oxidative activity for phosphites. Oxidation of phosphites outside cells may decrease an amount of phosphites taken into cells. On this account, it is desirable to also disrupt phoA gene.

In light of the above, in Example 2, a transformant in which 8 genes in total were disrupted was prepared. The 8 genes included respective genes encoding phosphate transporter proteins (specifically, pitA protein, pitB protein, phnCDE protein, and pstSCAB protein), respective genes encoding phosphate ester transporter proteins (glpT protein, UgpB protein, and UhpT protein) and a gene encoding an alkaline phosphatase protein (specifically, phoA protein).

Gene disruption was carried out basically by repeating P1 phage transduction and removal of a kanamycin resistance gene by cCP 20 which is a Flipparse (FLP) expression plasmid.

P1 phage for the gene disruption, except for disruption of the gene encoding pstSCAB protein, was prepared by using a library of *E. coli* gene disruption strains (KEIO Library, National BioResource Project: *E. coli*, NIG, Japan).

*E. coli* BW17355 strain was used for disruption of the gene encoding pstSCAB protein. There is no limitation to the order of gene disruption. Since an inorganic phosphate is more suitable than a phosphate ester for keeping a high proliferation rate of cells and making a culture operation easier, the gene encoding pstSCAB protein was disrupted at the end.

If both of the gene encoding a phosphate ester transporter protein and the gene encoding a phosphate transporter protein are totally disrupted, a resultant transformant cannot grow in a culture medium containing phosphate as a phosphorus source. On this account, htxABCDE/pSTV and ptxD/pTWV were introduced into a transformant prior to disruption of the gene encoding pstSCAB protein. The htxABCDE/pSTV and the ptxD/pTWV are plasmids necessary for phosphite-specific transportation and hypophosphite-specific transportation, and for oxidization of phosphite. Strains in which the genes had been disrupted were ultimately selected by using MOPS-Pt solid media each containing kanamycin, ampicillin and chloramphenicol.

The following method was used for a gene disruption operation.

(i) Preparation of P1 Phage Solution

A fluid in which a KEIO clone was cultured overnight was inoculated at 1.0% in a 2xYT medium containing 5 mM CaCl$_2$ and 0.2% glucose, and one hour culturing was carried out at 37° C.

Into a culture fluid thus obtained, 100 µl of wild-type P1 phage solution was added and culturing was carried out for 2 hours to 3 hours at 37° C.

After it was confirmed that the culture fluid was transparent and was in a lytic state, 1 ml of the culture fluid was transferred into a tube. Into the tube, 2 drops to 3 drops of chloroform was added and mixed.

The tube was subjected to centrifugation (15,000 rpm, 4° C., 5 min), and a supernatant thus separated was transferred to another tube (second tube).

Into the second tube, 2 drops to 3 drops of chloroform were further added. Then, the second tube was subjected to centrifugation under the similar conditions. Further, a supernatant thus separated was transferred to yet another tube (third tube). Into the third tube, 2 drops to 3 drops of chloroform were added. A resultant solution was used as P1 phage solution.

(ii) Gene Disruption by Transduction

The P1 phage solution thus prepared was used for carrying out gene disruption.

Into a tube, 500 µl of a culture fluid containing bacteria which disrupt genes was transferred. The tube was subjected to centrifugation (14,000 rpm, 4° C., 5 min) and the bacteria were collected.

The bacteria thus collected were suspended in 500 µl of a 2xYT medium containing 100 mM MgSO$_4$ and 5 mM CaCl$_2$.

Then, 100 µl of a suspension thus obtained was transferred to another tube. Into the another tube, 100 µl of the P1 phage solution 50-fold diluted was added. Thereafter, incubation was carried out for 30 minutes at 37° C.

Into the suspension, 200 µl of 1 M Na-citrate (pH 5.5) and 1 ml of 2xYT were added. Then, incubation was carried out for one hour at 37° C.

The suspension was subjected to centrifugation (6,000 rpm, 4° C., 5 min), so that sedimentation of the bacteria occurred. Meanwhile, a supernatant was discarded. The bacteria thus settled were suspended in 200 µl of 2xYT containing 100 mM Na-citrate (pH 5.5).

Then, 100 µl of the suspension was spread on a 2xYT plate containing kanamycin (50 µg/mL). Then, culturing was carried out at 37° C., so as to cause the bacteria to form colonies.

(iii) Removal of Kanamycin Resistance Gene by pCP20 which is FLP Expression Plasmid In a strain obtained by transduction with the P1 phage prepared from the KEIO clone, a kanamycin resistance gene is inserted in a target gene and on both sides of the kanamycin resistance gene, an FLP recognition target (FRT) sequence is present. This allows for removal of the kanamycin resistance gene by FLP expression.

Into the strain having been transduced, pCP20 was introduced by electroporation. Then, after this transduced strain was spread on a 2xYT plate to which ampicillin was added, the transduced strain was incubated at 28° C. As a result, the transduced strain formed colonies.

Bacteria which formed colonies were inoculated in a 2xYT liquid medium which did not contain any antibiotic substance, and were cultured overnight at 37° C. A culture fluid 10$^{-6}$-fold to 10$^{-8}$-fold diluted was spread on a 2xYT plate, so that the bacteria formed colonies. The colonies thus formed were inoculated on a 2xYT plate containing kanamycin and on a 2xYT plate containing no kanamycin. Then, a strain from which the kanamycin resistance gene was removed was obtained by selecting colonies lacking kanamycin resistance. This procedure was repeated so as to prepare a strain which was defective in 7 genes (pitA, pitB, phnC, phoA, glpT, ugpB, and uhpT). Into the strain thus prepared, the htxABCDE/pSTV and the ptxD/pTWV were introduced. The htxABCDE/pSTV and the ptxD/pTWV are plasmids necessary for phosphate-specific transportation and hypophosphite-specific transportation and for oxidization of phosphite. A resultant strain was used as an RN-01 strain.

The RN-01 was transduced by the P1 phage prepared from the W17355 strain, so that a strain defective in pstSCAB was obtained. The strain was designated as RN-02.

The RN-02 strain prepared as above, the above-described MT2012, and wild-type *E. coli* were each inoculated in liquid media each containing, as a phosphorus source, phosphorus (Pi), glycerol 3-phosphate (G3P), phosphite (Pt), or hypophosphite (HPt). Then, it was checked whether proliferation had occurred in the liquid medium.

Figure 3:
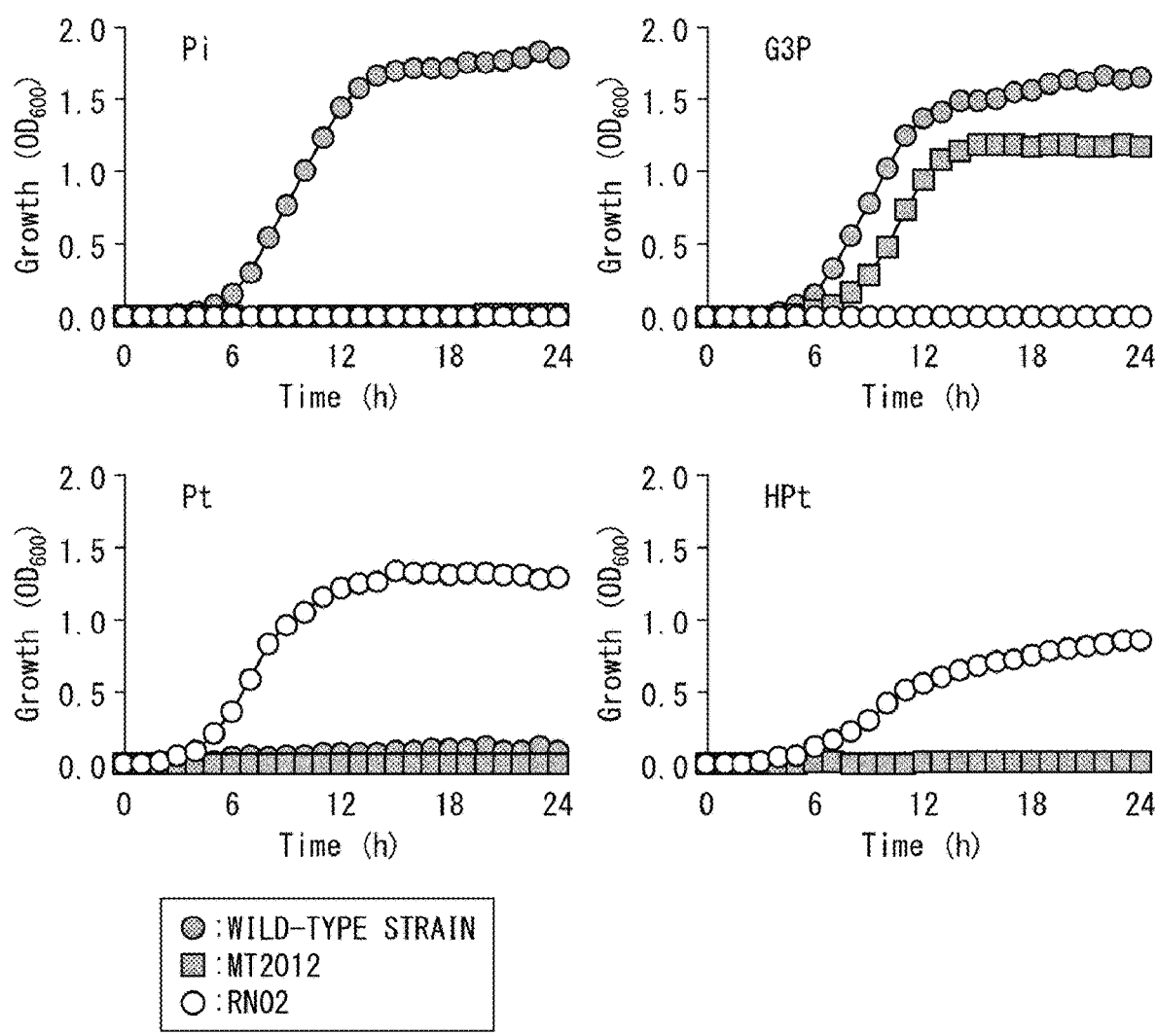
FIG. 3 shows graphs indicative of respective reduced phosphorous compound-dependent proliferation abilities of transformants in an Example of the present invention.

FIG. 3 shows results of checking the occurrence of proliferation. It was clarified in FIG. 3 that the RN-02 strain has no ability to proliferate dependently on phosphate or phosphate ester but has an ability to proliferate dependently on a reduced phosphorous compound.

Example 3. Measurement of Escape Probability of RN-02 Strain 3-1. Spot Assay

The RN-02 strain was cultured overnight in a MOPS-Pt liquid medium, and then, 1 mL of a culture fluid was collected in a tube. Thereafter, centrifugation was carried out so as to cause sedimentation of bacteria. A supernatant was discarded. The bacteria thus settled were suspended in 1 mL of sterile water, and bacteria were washed.

A resultant suspension containing the bacteria was diluted with sterile water, so that a 10-fold dilution series of the suspension was prepared. Specifically, $10^1$-fold to $10^7$-fold diluted solutions were prepared by diluting the suspension containing the bacteria. An assay plate was spotted with these $10^2$-fold to $10^7$-fold diluted solutions such that 10 µL of each of the $10^2$-fold to $10^7$-fold diluted solutions was at each spot.

The following assay plates were used: an LB plate, a 2xYT plate, a Terrific Broth plate (BD, Franklin Lakes, N.J.), a Sheep blood agar plate (Kohjin BIO, Saitama, Japan), a Chocolate agar plate (BD, Franklin Lakes, N.J.), a Soil A plate, a Soil B plate, a MOPS-phosphate (Pi) medium plate, a MOPS-phosphite (Pt) medium plate, and a MOPS-hypophosphite (HPt) medium plate.

Soil extract media (SoilA and SoilB) were prepared as follows. To 1 kg of each of two different kinds of leaf soil (A, B) available on the market, 1 L of tap water was added and autoclaving was performed for 30 minutes at 121° C. A supernatant thus obtained was filtrated by a filter paper, so that soil extract was prepared. A MOPS medium plate was prepared with use of the soil extract, and resultant media were designated as SoilA and SoilB.

Figure 4:
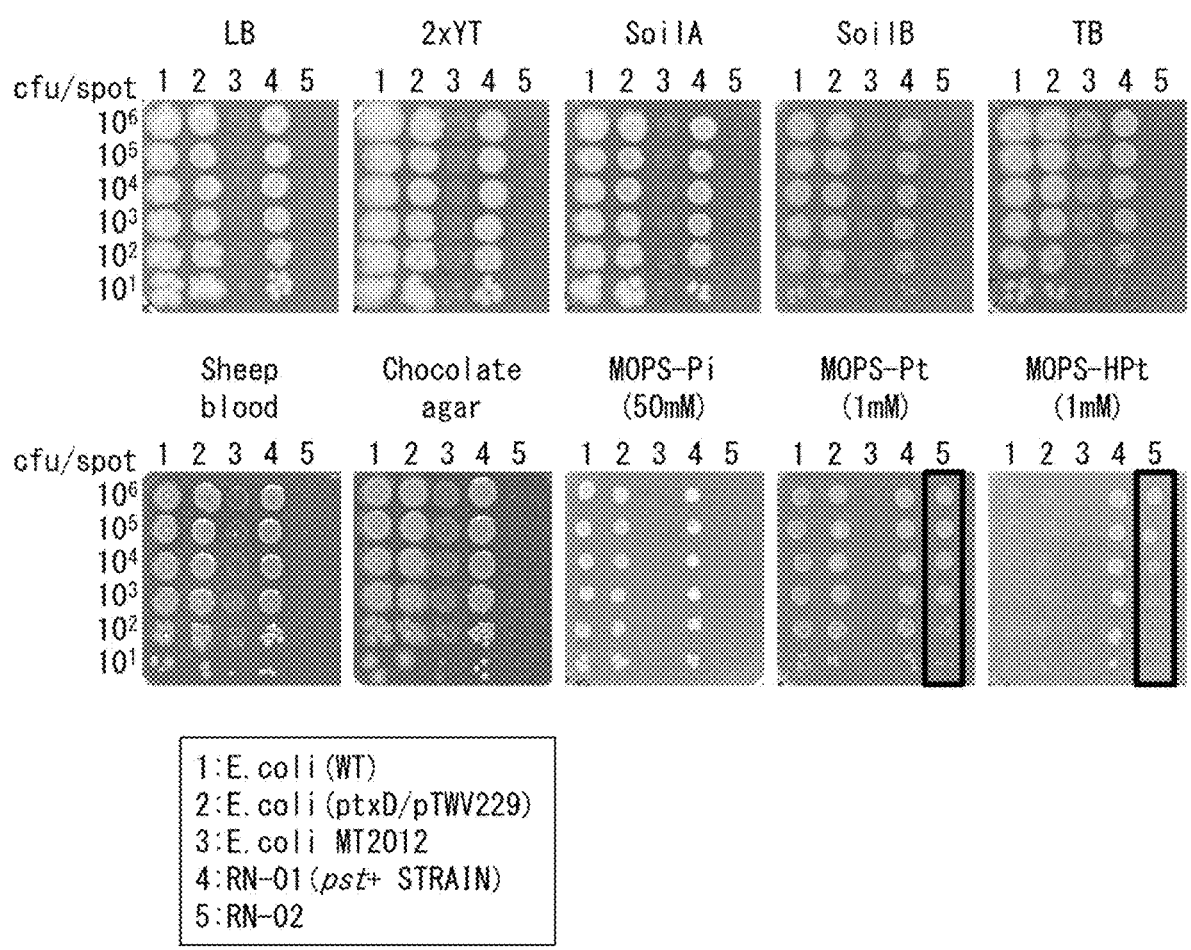
FIG. 4 shows images indicative of respective reduced phosphorous compound-dependent proliferation abilities of transformants in an Example of the present invention.

FIG. 4 shows test results. As shown in FIG. 4, it was clarified that the RN-02 strain proliferates in none of a complex medium, a soil extract medium, and a serum medium.

3-2. Evaluation of Escape Probability and Survivability in Long-Term Culture of Fluid The following describes how experiments to examine escape probability and survivability of the RN-02 strain in fluid culture were performed.

First, 1.0 ml of culture fluid in which the RN-02 strain was cultured overnight was subjected to centrifugation. Then, bacteria were suspended in 1.0 ml of a MOPS medium (MOPS0) which did not contain phosphate, so that the bacteria were washed.

After the bacteria were washed, the MOPS medium containing the bacteria was subjected to centrifugation and the bacteria were collected. The bacteria thus collected were re-suspended in a fresh MOPS medium such that the OD600 would be 1.0.

Then, 1.0 mL of a resultant suspension was inoculated in a 500 ml conical flask containing 100 mL of a proliferation permissive culture medium (MOPS-Pt) or a proliferation non-permissive culture medium (2xYT). Then, shaking culture was carried out at 37° C.

Immediately after the shaking culture started, sampling of that culture medium was started. The sampling of 0.5 mL of the culture medium was intermittently carried out for 14 days. The sampling here was performed every three hours until 12 hours from the start of the sampling on the first day, and every 24 hours after 12 hours had elapsed from the start of the sampling.

After the OD600 value of each sample harvested was measured, the sample was appropriately diluted with MOPS0. Then, 0.1 mL of a resultant diluted solution was spread on both of three permissive culture medium plates (for CFU measurement) and three non-permissive culture medium plates (for escape probability measurement).

The permissive culture medium plates were subjected to incubation for 48 hours at 37° C. while the non-permissive culture medium plates were subjected to incubation for 7 days at 37° C. Then, colony formation was observed. The number of colonies in the permissive culture medium was calculated by the following Expression, as the number of colonies formed per culture fluid (CFU/mL):

[Number of colonies formed per culture fluid (CFU/mL)]=[average of numbers of colonies (CFU)]×[dilution factor (–)]/[amount of spread culture fluid (mL)]

Figure 5:
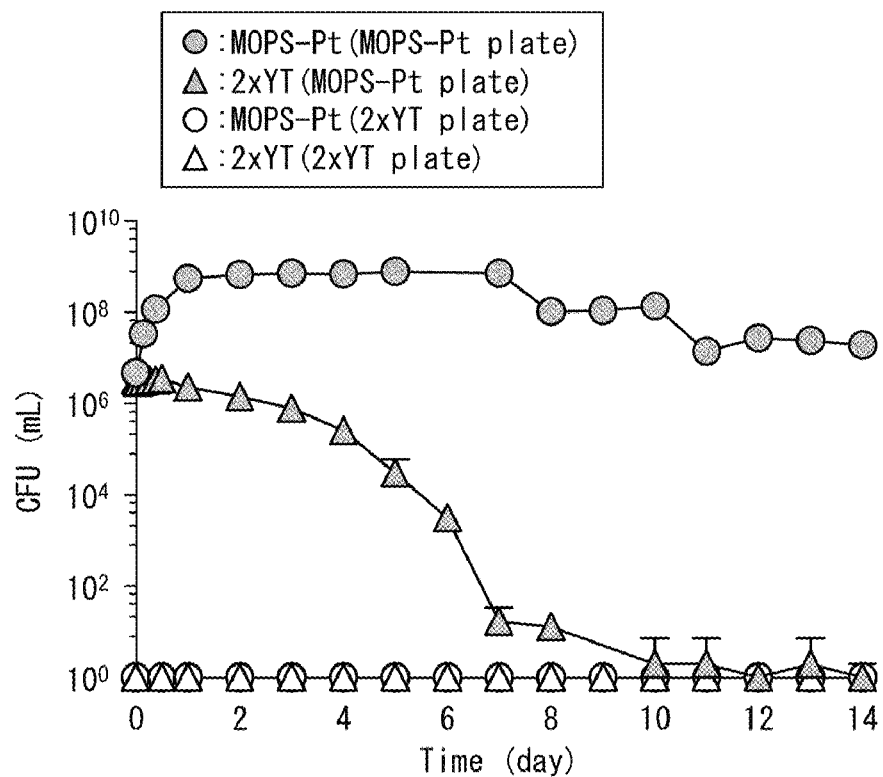
FIG. 5 shows graphs indicative of respective reduced phosphorous compound-dependent proliferation abilities of transformants in an Example of the present invention.
Figure 5:
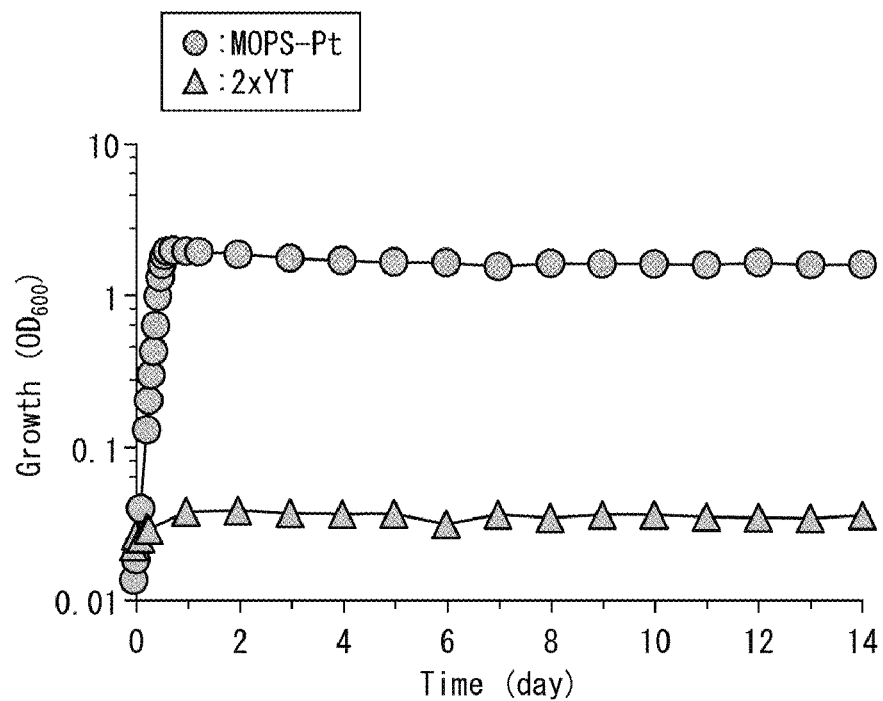

FIG. 5 shows test results. As shown in FIG. 5, it was clarified that the RN-02 strain proliferates dependently on a reduced phosphorous compound for a long term.

3-3. Escape Assay

The RN-02 strain cultured in 10 mL of a MOPS-Pt liquid medium was inoculated into 1 L of the MOPS-Pt medium, and was cultured for 24 hours at 37° C.

After culturing, 0.1 mL of a culture fluid was collected and $10^{-5}$-fold to $10^{-7}$-fold diluted. Then, 0.1 mL of a resultant diluted solution of the culture fluid was spread on a MOPS-Pt plate (permissive culture medium).

After all remaining culture fluid was subjected to centrifugation and bacteria were collected, the bacteria were washed with sterile water and re-suspended in approximately 10 mL of sterile water.

Then, 1.0 mL of a resultant suspension of the bacteria was spread on a 2xYT plate (non-permissive culture medium) which was prepared by using a 180 mm×180 mm square dish.

The 2xYT plate was cultured at 37° C. for 7 days. The plate was observed every day and appearance of colonies was checked. On the non-permissive culture medium, colony growth was not confirmed. A detection limit in the present experimental system was expressed by a numerical value obtained by the following calculation formula:

[Detection limit (escapee/CFU)]=1/([number of colonies formed (CFU)]×[dilution factor (–)]/[amount of spread culture fluid (mL)]×[amount of culture fluid used (mL)])

A detection limit in the present experiment was $1.94 \times 10^{-13}$.

INDUSTRIAL APPLICABILITY

An embodiment of the present invention can be widely used in fields which require transformants (e.g., the field of oral vaccine production, and fields aiming at improvement of natural environment).

The invention claimed is:

1. A transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation, wherein the hypophosphite transporter protein is HtxBCDE protein and is (i) a protein consisting of a protein which is encoded by a gene consisting of any one of the following polynucleotides (1) to (2) and from which HtxA protein is excluded, or (ii) a protein including, as at least part thereof, the protein which is encoded by the gene consisting of any one of the following polynucleotides (1) to (2) and from which HtxA protein is excluded:

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity, wherein the stringent condition comprises hybridization in a first buffer solution for 16 hours to 24 hours at a temperature in a range from 60° C. to 68° C., and then washing twice in a second buffer solution for 15 minutes at a temperature in a range from 60° C. to 68° C.;

wherein the first buffer solution comprises 0.25M $Na_2HPO_4$, pH 7.2, 7% SDS, 1 mM EDTA, and 1×Denhardt's solution, wherein the second buffer solution comprises 20 mM $Na_2HPO_4$, pH 7.2, 1% SDS, and 1 mM EDTA.

2. The transformant as set forth in claim 1, wherein:
a gene encoding a phosphite dehydrogenase protein is further introduced.

3. The transformant as set forth in claim 1, defective in a function of a gene encoding an alkaline phosphatase protein.

4. The transformant as set forth in claim 1, being a transformant of *E. coli*.

5. The transformant as set forth in claim 4, wherein:
the phosphate transporter protein is at least one selected from the group consisting of PitA protein, PitB protein, PstSCAB protein, and PhnCDE protein.

6. The transformant as set forth in claim 4, wherein:
the phosphate ester transporter protein is at least one selected from the group consisting of UhpT protein, UgpB protein, and GlpT protein.

7. A transformant which is defective in functions of a gene encoding a phosphate transporter protein and a gene encoding a phosphate ester transporter protein and into which a gene encoding HtxABCDE protein is introduced, the transformant being incapable of utilizing phosphate for proliferation but capable of utilizing hypophosphite for proliferation, wherein the HtxABCDE protein is (i) a protein consisting of a protein encoded by a gene consisting of any one of the following polynucleotides (1) to (2) or (ii) a protein including, as at least part thereof, the protein which is encoded by the gene consisting of any one of the following polynucleotides (1) to (2):

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity, wherein the stringent condition comprises hybridization in a first buffer solution for 16 hours to 24 hours at a temperature in a range from 60° C. to 68° C., and then washing twice in a second buffer solution for 15 minutes at a temperature in a range from 60° C. to 68° C.;

wherein the first buffer solution comprises 0.25M $Na_2HPO_4$, pH 7.2, 7% SDS, 1 mM EDTA, and 1×Denhardt's solution;

wherein the second buffer solution comprises 20 mM $Na_2HPO_4$, pH 7.2, 1% SDS, and 1 mM EDTA.

8. A method for producing a transformant, comprising the step of:

introducing a gene encoding HtxABCDE protein into a host that is defective in functions of a gene encoding a phosphate transporter protein and a gene encoding a phosphate ester transporter protein, wherein the HtxABCDE protein is (i) a protein consisting of a protein encoded by a gene consisting of any one of the following polynucleotides (1) to (2) or (ii) a protein including, as at least part thereof, the protein which is encoded by the gene consisting of any one of the following polynucleotides (1) to (2):

(1) a polynucleotide consisting of the base sequence of SEQ ID NO: 24;

(2) a polynucleotide (i) being hybridizable, under a stringent condition, with DNA consisting of a base sequence complementary to the base sequence of SEQ ID NO: 24, and (ii) encoding a protein which does not have phosphate transport activity but which has reduced phosphorous compound transport activity, wherein the stringent condition comprises hybridization in a first buffer solution for 16 hours to 24 hours at a temperature in a range from 60° C. to 68° C., and then washing twice in a second buffer solution for 15 minutes at a temperature in a range from 60° C. to 68° C.;

wherein the first buffer solution comprises 0.25M $Na_2HPO_4$, pH 7.2, 7% SDS, 1 mM EDTA, and 1×Denhardt's solution;

wherein the second buffer solution comprises 20 mM $Na_2HPO_4$, pH 7.2, 1% SDS, and 1 mM EDTA.

9. A method for detecting the presence of a reduced phosphorous compound, comprising the steps of:
culturing a transformant recited in claim 1, with use of a culture medium as a detection target; and
detecting whether or not the transformant proliferated in the step of culturing.

10. The method as set forth in claim 9, wherein:
the reduced phosphorous compound is phosphonate.

11. A method for detecting the presence of a reduced phosphorous compound, comprising the steps of:
culturing a transformant recited in claim 7, with use of a culture medium as a detection target; and
detecting whether or not the transformant proliferated in the step of culturing.

12. The method as set forth in claim 11, wherein:
the reduced phosphorous compound is phosphonate.

* * * * *

SEQUENCE LISTING

<160> NUMBER OF SEQ ID NOS: 44

<210> SEQ ID NO 1
<211> LENGTH: 1500
<212> TYPE: DNA
<213> ORGANISM: E.coli

<400> SEQUENCE: 1

```
atgctacatt tgtttgctgg cctggatttg cataccgggc tgttattatt gcttgcactg      60
gcttttgtgc tgttctacga agccatcaat ggtttccatg acacagccaa cgccgtggca     120
accgttatct atacccgcgc gatgcgttct cagctcgccg tggttatggc ggcggtattc     180
aactttttgg gtgttttgct gggtggtctg agtgttgcct atgccattgt gcatatgctg     240
ccgacggatc tgctgcttaa tatgggatcg tctcatggcc ttgccatggt gttctctatg     300
ttgctggcgg cgattatctg gaacctgggt acctggtact ttggtttacc tgcatccagc     360
tctcatacgc tgattggcgc gatcatcggg attggtttaa ccaatgcgtt gatgaccggg     420
acgtcagtgg tggatgcact caatatcccg aaagtattaa gtatttttcgg ttctctgatc     480 gtttccccta ttgtcggcct ggtgtttgct ggcggtctga ttttcttgct gcgtcgctac     540
tggagcggca ccaagaaacg cgcccgtatc cacctgaccc cagcggagcg tgaaaagaaa     600
gacggcaaga aaaagccgcc gttctggacg cgtattgcgc tgatcctttc cgctatcggc     660
gtggcgtttt cgcacggcgc gaacgatggt cagaaaggca ttggtctggt tatgttggta     720
```

```
ttgattggcg tcgcgccagc aggcttcgtg gtgaacatga atgccactgg ctacgaaatc    780
acccgtaccc gtgatgccat caacaacgtc gaagcttact ttgagcagca tcctgcgctg    840
ctcaaacagg ctaccggtgc tgatcagtta gtaccggctc cggaagctgg cgcaacgcaa    900
cctgcggagt tccactgcca tccgtcgaat accattaacg cgctcaaccg cctgaaaggt    960
atgttgacca ccgatgtgga aagctacgac aagctgtcgc ttgatcaacg tagccagatg   1020
cgccgcatta tgctgtgcgt ttctgacact atcgacaaag tggtgaagat gcctggcgtg   1080
agtgctgacg atcagcgcct gttgaagaaa ctgaagtccg acatgcttag caccatcgag   1140
tatgcaccgg tgtggatcat catggcggtc gcgctggcgt taggtatcgg tacgatgatt   1200
ggctggcgcc gtgtggcaac gactatcggt gagaaaatcg gtaagaaagg catgacctac   1260
gctcagggga tgtctgccca gatgacggcg gcagtgtcta tcggcctggc gagttatacc   1320
gggatgccgg tttccactac tcacgtactc tcctcttctg tcgcggggac gatggtggta   1380
gatggtggcg gcttacagcg taaaaccgtg accagcattc tgatggcctg ggtgtttacc   1440
cttccggctg cggtactgct ttccggcggg ctgtactggc tctccttgca gttcctgtaa   1500
```

<210> SEQ ID NO 2
<211> LENGTH: 499
<212> TYPE: PRT
<213> ORGANISM: E.coli

<400> SEQUENCE: 2

```
Met Leu His Leu Phe Ala Gly Leu Asp Leu His Thr Gly Leu Leu Leu
1               5                   10                  15

Leu Leu Ala Leu Ala Phe Val Leu Phe Tyr Glu Ala Ile Asn Gly Phe
            20                  25                  30

His Asp Thr Ala Asn Ala Val Ala Thr Val Ile Tyr Thr Arg Ala Met
        35                  40                  45

Arg Ser Gln Leu Ala Val Val Met Ala Ala Val Phe Asn Phe Leu Gly
    50                  55                  60

Val Leu Leu Gly Gly Leu Ser Val Ala Tyr Ala Ile His Met Leu
65                  70                  75                  80

Pro Thr Asp Leu Leu Leu Asn Met Gly Ser Ser His Gly Leu Ala Met
                85                  90                  95

Val Phe Ser Met Leu Leu Ala Ala Ile Ile Trp Asn Leu Gly Thr Trp
            100                 105                 110

Tyr Phe Gly Leu Pro Ala Ser Ser His Thr Leu Ile Gly Ala Ile
        115                 120                 125

Ile Gly Ile Gly Leu Thr Asn Ala Leu Met Thr Gly Thr Ser Val Val
    130                 135                 140

Asp Ala Leu Asn Ile Pro Lys Val Leu Ser Ile Phe Gly Ser Leu Ile
145                 150                 155                 160

Val Ser Pro Ile Val Gly Leu Val Phe Ala Gly Gly Leu Ile Phe Leu
                165                 170                 175

Leu Arg Arg Tyr Trp Ser Gly Thr Lys Lys Arg Ala Arg Ile His Leu
            180                 185                 190

Thr Pro Ala Glu Arg Glu Lys Lys Asp Gly Lys Lys Pro Pro Phe
        195                 200                 205

Trp Thr Arg Ile Ala Leu Ile Leu Ser Ala Ile Gly Val Ala Phe Ser
    210                 215                 220

His Gly Ala Asn Asp Gly Gln Lys Gly Ile Gly Leu Val Met Leu Val
225                 230                 235                 240
```

```
Leu Ile Gly Val Ala Pro Ala Gly Phe Val Val Asn Met Asn Ala Thr
                245                 250                 255

Gly Tyr Glu Ile Thr Arg Thr Arg Asp Ala Ile Asn Asn Val Glu Ala
            260                 265                 270

Tyr Phe Glu Gln His Pro Ala Leu Leu Lys Gln Ala Thr Gly Ala Asp
        275                 280                 285

Gln Leu Val Pro Ala Pro Glu Ala Gly Ala Thr Gln Pro Ala Glu Phe
    290                 295                 300

His Cys His Pro Ser Asn Thr Ile Asn Ala Leu Asn Arg Leu Lys Gly
305                 310                 315                 320

Met Leu Thr Thr Asp Val Glu Ser Tyr Asp Lys Leu Ser Leu Asp Gln
                325                 330                 335

Arg Ser Gln Met Arg Arg Ile Met Leu Cys Val Ser Asp Thr Ile Asp
            340                 345                 350

Lys Val Val Lys Met Pro Gly Val Ser Ala Asp Asp Gln Arg Leu Leu
        355                 360                 365

Lys Lys Leu Lys Ser Asp Met Leu Ser Thr Ile Glu Tyr Ala Pro Val
    370                 375                 380

Trp Ile Ile Met Ala Val Ala Leu Ala Leu Gly Ile Gly Thr Met Ile
385                 390                 395                 400

Gly Trp Arg Arg Val Ala Thr Thr Ile Gly Glu Lys Ile Gly Lys Lys
                405                 410                 415

Gly Met Thr Tyr Ala Gln Gly Met Ser Ala Gln Met Thr Ala Ala Val
            420                 425                 430

Ser Ile Gly Leu Ala Ser Tyr Thr Gly Met Pro Val Ser Thr Thr His
        435                 440                 445

Val Leu Ser Ser Val Ala Gly Thr Met Val Val Asp Gly Gly Gly Gly
    450                 455                 460

Leu Gln Arg Lys Thr Val Thr Ser Ile Leu Met Ala Trp Val Phe Thr
465                 470                 475                 480

Leu Pro Ala Ala Val Leu Leu Ser Gly Gly Leu Tyr Trp Leu Ser Leu
                485                 490                 495

Gln Phe Leu

<210> SEQ ID NO 3
<211> LENGTH: 1500
<212> TYPE: DNA
<213> ORGANISM: E.coli

<400> SEQUENCE: 3
atgctaaatt tatttgttgg ccttgatata tacacagggc ttttgttatt gcttgctctg     60
gcatttgtgt tgttctacga agcaatcaat ggttttcatg acacggcgaa tgcggtggca    120
gccgttattt atactcgtgc catgcaacca caacttgctg tggtgatggc ggcatttttt    180 aactttttg gcgtgttatt gggcggactt agcgttgcct atgccattgt ccatatgttg    240
ccaaccgatt gttgctgaa tatggggtca acccacggcc tggcgatggt cttttccatg    300
ctgctggcgg cgattatctg gaacctggga acgtggttct tcggtttacc ggcctccagt    360
tcgcacacct tgattggtgc gattatcggc atcggtttaa ccaacgcgct gttaaccggc    420
tcatcggtga tggatgcgtt aaacctgcgt gaagtgacca aaatttctc ctcgctgatt    480 gtttcccta tcgtcggcct ggtcattgcg ggaggcctga tattcctgct gcgacgctac    540
tggagcggga cgaaaaagcg tgaccgtatt caccgcattc cggaagatcg caaaaagaaa    600
```

-continued

```
aaaggcaaac gtaaaccgcc attctggacg cgtattgcgc tgattgtttc cgctgcgggc    660
gtggcgtttt cgcacggcgc gaacgacgga caaaaaggga tcggcctggt aatgctggta    720
ctggtgggga ttgcccctgc tggcttcgtc gtcaatatga atgcgtccgg ctatgaaatt    780
acccgtaccc gcgatgccgt taccaacttc gaacactacc tgcaacagca tcctgaactg    840
ccgcagaagt tgattgcgat ggaacctcca ttgcctgcag catcgactga tggcacgcaa    900
gtaacagagt ttcactgtca tccggcaaat acctttgatg ctattgcgcg cgttaaaacg    960
atgctgccag gcaatatgga agttacgag ccgttaagcg tgagtcagcg cagccagctg   1020
cgccgcatta tgctgtgcat ctctgatacc tccgcgaagc tagcgaaact gccaggcgtc   1080
agtaaagaag accagaacct gctgaaaaaa cttcgcagcg atatgttaag caccattgag   1140
tacgctccgg tgtggatcat catggcggta gcactggcgc tcggcattgg caccatgatt   1200
ggctggcgtc gtgtagcgat gaccatcggt gagaagattg gtaagcgcgg catgacgtat   1260
gcgcaaggca tggcggcaca aatgacggcg gcagtgtcta tcggtcttgc cagttatatt   1320
gggatgcccg tctccacaac acacgtcctc tcgtctgcag ttgcagggac gatggtggtg   1380
gacggcggtg ggttacagcg taaaacggta accagcatcc tgatggcgtg ggtatttact   1440
ttaccggcgc caattttctc ttctggtggg ctgtactgga tagcattgca gttgatttaa   1500
```

```
<210> SEQ ID NO 4
<211> LENGTH: 499
<212> TYPE: PRT
<213> ORGANISM: E.coli

<400> SEQUENCE: 4
```

Met Leu Asn Leu Phe Val Gly Leu Asp Ile Tyr Thr Gly Leu Leu Leu
1               5                   10                  15

Leu Leu Ala Leu Ala Phe Val Leu Phe Tyr Glu Ala Ile Asn Gly Phe
            20                  25                  30

His Asp Thr Ala Asn Ala Val Ala Ala Val Ile Tyr Thr Arg Ala Met
        35                  40                  45

Gln Pro Gln Leu Ala Val Val Met Ala Ala Phe Phe Asn Phe Phe Gly
    50                  55                  60

Val Leu Leu Gly Gly Leu Ser Val Ala Tyr Ala Ile Val His Met Leu
65                  70                  75                  80

Pro Thr Asp Leu Leu Asn Met Gly Ser Thr His Gly Leu Ala Met
                85                  90                  95

Val Phe Ser Met Leu Leu Ala Ala Ile Ile Trp Asn Leu Gly Thr Trp
            100                 105                 110

Phe Phe Gly Leu Pro Ala Ser Ser His Thr Leu Ile Gly Ala Ile
        115                 120                 125

Ile Gly Ile Gly Leu Thr Asn Ala Leu Leu Thr Gly Ser Ser Val Met
    130                 135                 140

Asp Ala Leu Asn Leu Arg Glu Val Thr Lys Ile Phe Ser Ser Leu Ile
145                 150                 155                 160

Val Ser Pro Ile Val Gly Leu Val Ile Ala Gly Leu Ile Phe Leu
                165                 170                 175

Leu Arg Arg Tyr Trp Ser Gly Thr Lys Lys Arg Asp Arg Ile His Arg
            180                 185                 190

Ile Pro Glu Asp Arg Lys Lys Lys Gly Lys Arg Lys Pro Pro Phe
        195                 200                 205

Trp Thr Arg Ile Ala Leu Ile Val Ser Ala Ala Gly Val Ala Phe Ser
    210                 215                 220

```
His Gly Ala Asn Asp Gly Gln Lys Gly Ile Gly Leu Val Met Leu Val
225                 230                 235                 240

Leu Val Gly Ile Ala Pro Ala Gly Phe Val Asn Met Asn Ala Ser
            245                 250                 255

Gly Tyr Glu Ile Thr Arg Thr Arg Asp Ala Val Thr Asn Phe Glu His
        260                 265                 270

Tyr Leu Gln Gln His Pro Glu Leu Pro Gln Lys Leu Ile Ala Met Glu
    275                 280                 285

Pro Pro Leu Pro Ala Ala Ser Thr Asp Gly Thr Gln Val Thr Glu Phe
290                 295                 300

His Cys His Pro Ala Asn Thr Phe Asp Ala Ile Ala Arg Val Lys Thr
305                 310                 315                 320

Met Leu Pro Gly Asn Met Glu Ser Tyr Glu Pro Leu Ser Val Ser Gln
            325                 330                 335

Arg Ser Gln Leu Arg Arg Ile Met Leu Cys Ile Ser Asp Thr Ser Ala
        340                 345                 350

Lys Leu Ala Lys Leu Pro Gly Val Ser Lys Glu Asp Gln Asn Leu Leu
    355                 360                 365

Lys Lys Leu Arg Ser Asp Met Leu Ser Thr Ile Glu Tyr Ala Pro Val
370                 375                 380

Trp Ile Ile Met Ala Val Ala Leu Ala Leu Gly Ile Gly Thr Met Ile
385                 390                 395                 400

Gly Trp Arg Arg Val Ala Met Thr Ile Gly Glu Lys Ile Gly Lys Arg
            405                 410                 415

Gly Met Thr Tyr Ala Gln Gly Met Ala Ala Gln Met Thr Ala Ala Val
        420                 425                 430

Ser Ile Gly Leu Ala Ser Tyr Ile Gly Met Pro Val Ser Thr Thr His
    435                 440                 445

Val Leu Ser Ser Ala Val Ala Gly Thr Met Val Val Asp Gly Gly Gly
450                 455                 460

Leu Gln Arg Lys Thr Val Thr Ser Ile Leu Met Ala Trp Val Phe Thr
465                 470                 475                 480

Leu Pro Ala Ala Ile Phe Leu Ser Gly Gly Leu Tyr Trp Ile Ala Leu
            485                 490                 495

Gln Leu Ile

<210> SEQ ID NO 5
<211> LENGTH: 789
<212> TYPE: DNA
<213> ORGANISM: E.coli

<400> SEQUENCE: 5
atgcaaacga ttatccgtgt cgagaagctc gccaaaacct tcaatcagca tcaggcgctg      60
catgcggttg atctgaacat tcatcacggt gaaatggtgg ctctgcttgg gccgtcgggt     120
tccggaaaat ccacccttt t acgtcactta agcggtttga ttaccggcga taaatctgtc     180
ggtagccata tcgagctgct gggccgcaca gtccagcgcg aaggccgcct ggcccgcgat     240
atccgcaaaa gccgcgccca taccggctac atattccaac aattcaacct ggtgaaccgc     300
ctgagcgtac tggagaacgt gctgattggc gcgctcggca gcacgccgtt ctggcgcacc     360
tgttttagct ggttcaccgg cgagcagaaa cagcgcgcgt tacaggcgct gacccgcgtt     420
ggcatggtgc attttgccca tcagcgcgtt ccaccctct c cggcggcca gcagcaacgt     480 gtggcgattg cccgtgcgct gatgcagcag gcgaaagtga ttctggccga tgaacccatc     540
```

```
gcctcgctgg acccagaatc agcgcgcatc gtgatggaca ccctgcgcga catcaaccag    600
aacgacggca tcaccgtggt cgtcacgctg catcaggtgg attacgccct gcgctactgc    660
gaacgcatcg tcgccctgcg ccaggggcac gtcttctacg acggcagcag ccaacagttt    720
gataacgaac gttttgacca tctctaccgc agcattaacc gcgtcgaaga gaacgcgaaa    780
gctgcctga                                                            789
```

```
<210> SEQ ID NO 6
<211> LENGTH: 262
<212> TYPE: PRT
<213> ORGANISM: E.coli

<400> SEQUENCE: 6
```

Met Gln Thr Ile Ile Arg Val Glu Lys Leu Ala Lys Thr Phe Asn Gln
 1               5                  10                  15

His Gln Ala Leu His Ala Val Asp Leu Asn Ile His His Gly Glu Met
            20                  25                  30

Val Ala Leu Leu Gly Pro Ser Gly Ser Gly Lys Ser Thr Leu Leu Arg
        35                  40                  45

His Leu Ser Gly Leu Ile Thr Gly Asp Lys Ser Val Gly Ser His Ile
    50                  55                  60

Glu Leu Leu Gly Arg Thr Val Gln Arg Glu Gly Arg Leu Ala Arg Asp
65                  70                  75                  80

Ile Arg Lys Ser Arg Ala His Thr Gly Tyr Ile Phe Gln Gln Phe Asn
                85                  90                  95

Leu Val Asn Arg Leu Ser Val Leu Glu Asn Val Leu Ile Gly Ala Leu
            100                 105                 110

Gly Ser Thr Pro Phe Trp Arg Thr Cys Phe Ser Trp Phe Thr Gly Glu
        115                 120                 125

Gln Lys Gln Arg Ala Leu Gln Ala Leu Thr Arg Val Gly Met Val His
    130                 135                 140

Phe Ala His Gln Arg Val Ser Thr Leu Ser Gly Gly Gln Gln Gln Arg
145                 150                 155                 160

Val Ala Ile Ala Arg Ala Leu Met Gln Gln Ala Lys Val Ile Leu Ala
                165                 170                 175

Asp Glu Pro Ile Ala Ser Leu Asp Pro Glu Ser Ala Arg Ile Val Met
            180                 185                 190

Asp Thr Leu Arg Asp Ile Asn Gln Asn Asp Gly Ile Thr Val Val Val
        195                 200                 205

Thr Leu His Gln Val Asp Tyr Ala Leu Arg Tyr Cys Glu Arg Ile Val
    210                 215                 220

Ala Leu Arg Gln Gly His Val Phe Tyr Asp Gly Ser Ser Gln Gln Phe
225                 230                 235                 240

Asp Asn Glu Arg Phe Asp His Leu Tyr Arg Ser Ile Asn Arg Val Glu
                245                 250                 255

Glu Asn Ala Lys Ala Ala
            260

```
<210> SEQ ID NO 7
<211> LENGTH: 1017
<212> TYPE: DNA
<213> ORGANISM: E.coli

<400> SEQUENCE: 7
```

```
atgaacgcta agataattgc ctcgctggcc ttcaccagca tgttcagcct cagcaccctg    60
```

```
ttaagcccgg cgcacgccga agagcaggaa aaggcgttga atttcggcat tatttcaacg      120
gaatcacagc aaaacctgaa accgcaatgg acgccgttct tgcaggatat ggagaagaag      180
ctgggcgtga aggtcaacgc cttctttgcc ccggactacg cgggcattat ccaggggatg      240
cgcttcaata aagtggatat cgcctggtac ggcaatctgt cggcgatgga agcggtggat      300
cgcgccaatg gccaggtctt cgcccagacg gtcgcggcgg atggatcgcc gggttactgg      360
agcgtgttga tcgtcaacaa agacagtccg atcaacaacc tgaacgatct gctggcgaag      420
cggaaagatc tcacctttgg caatggcgat cctaactcca cctctggctt cctcgtcccc      480
ggctactacg tcttcgccaa aaacaatatc tccgccagcg acttcaagcg caccgtcaac      540
gccgggcatg aaaccaacgc gctggccgtc gccaacaagc aggtggatgt tgccaccaac      600
aacaccgaaa acctcgacaa gctgaaaacc tccgcgccag agaagctgaa agaactgaag      660
gtgatctgga agtcgccgct gatcccaggc gatccgatcg tctggcgcaa gaatctttcc      720
gaaaccacca agacaagat ctacgacttc tttatgaact acggcaaaac gccggaagaa      780
aaagcggtgc tggaacgcct gggctgggcg ccattccgcg cttccagcga cctgcaactg      840
gtgccgattc gccagctcgc gctgtttaaa gagatgcagg gcgtgaaaag caataaagga      900
ctgaatgagc aggacaagct ggcaaaaacc accgagattc aggcgcagct ggatgacctg      960
gaccgcctga caacgcgct aagcgcgatg agttcggtga gtaaagcggt gcagtaa      1017

<210> SEQ ID NO 8
<211> LENGTH: 338
<212> TYPE: PRT
<213> ORGANISM: E.coli

<400> SEQUENCE: 8

Met Asn Ala Lys Ile Ile Ala Ser Leu Ala Phe Thr Ser Met Phe Ser
1               5                   10                  15

Leu Ser Thr Leu Leu Ser Pro Ala His Ala Glu Glu Gln Lys Ala
            20                  25                  30

Leu Asn Phe Gly Ile Ile Ser Thr Glu Ser Gln Gln Asn Leu Lys Pro
        35                  40                  45

Gln Trp Thr Pro Phe Leu Gln Asp Met Glu Lys Lys Leu Gly Val Lys
    50                  55                  60

Val Asn Ala Phe Phe Ala Pro Asp Tyr Ala Gly Ile Ile Gln Gly Met
65                  70                  75                  80

Arg Phe Asn Lys Val Asp Ile Ala Trp Tyr Gly Asn Leu Ser Ala Met
                85                  90                  95

Glu Ala Val Asp Arg Ala Asn Gly Gln Val Phe Ala Gln Thr Val Ala
            100                 105                 110

Ala Asp Gly Ser Pro Gly Tyr Trp Ser Val Leu Ile Val Asn Lys Asp
        115                 120                 125

Ser Pro Ile Asn Asn Leu Asn Asp Leu Leu Ala Lys Arg Lys Asp Leu
    130                 135                 140

Thr Phe Gly Asn Gly Asp Pro Asn Ser Thr Ser Gly Phe Leu Val Pro
145                 150                 155                 160

Gly Tyr Tyr Val Phe Ala Lys Asn Asn Ile Ser Ala Ser Asp Phe Lys
                165                 170                 175

Arg Thr Val Asn Ala Gly His Glu Thr Asn Ala Leu Ala Val Ala Asn
            180                 185                 190

Lys Gln Val Asp Val Ala Thr Asn Asn Thr Glu Asn Leu Asp Lys Leu
        195                 200                 205
```

Lys Thr Ser Ala Pro Glu Lys Leu Lys Glu Leu Lys Val Ile Trp Lys
                210                 215                 220

Ser Pro Leu Ile Pro Gly Asp Pro Ile Val Trp Arg Lys Asn Leu Ser
225                 230                 235                 240

Glu Thr Thr Lys Asp Lys Ile Tyr Asp Phe Phe Met Asn Tyr Gly Lys
                245                 250                 255

Thr Pro Glu Glu Lys Ala Val Leu Glu Arg Leu Gly Trp Ala Pro Phe
                260                 265                 270

Arg Ala Ser Ser Asp Leu Gln Leu Val Pro Ile Arg Gln Leu Ala Leu
                275                 280                 285

Phe Lys Glu Met Gln Gly Val Lys Ser Asn Lys Gly Leu Asn Glu Gln
                290                 295                 300

Asp Lys Leu Ala Lys Thr Thr Glu Ile Gln Ala Gln Leu Asp Asp Leu
305                 310                 315                 320

Asp Arg Leu Asn Asn Ala Leu Ser Ala Met Ser Ser Val Ser Lys Ala
                325                 330                 335

Val Gln

<210> SEQ ID NO 9
<211> LENGTH: 780
<212> TYPE: DNA
<213> ORGANISM: E.coli

<400> SEQUENCE: 9
atgcaaacca tcaccatcgc cccacccaag cgcagctggt tctcgcttct gagctgggcc     60
gttgtactcg ccgtgttggt cgtctcgtgg cagggcgcgg aaatggcccc gcttacgctg    120
atcaaagacg gcggcaacat ggcgacgttc gccgccgact tcttcccgcc cgatttcagc    180
cagtggcagg attacctcac cgaaatggcc gtcacgctgc aaatcgccgt ctggggcacc    240
gcgctggcgg tggttctctc catccccttt ggcctgatga cgccgaaaaa cctggtgccg    300
tggtgggttt accagcccgt cgccgcctg atggacgcct ccgcgccat taacgaaatg    360 gtcttcgcca tgctgttcgt ggtcgccgtc ggcctcggcc cgttcgctgg cgtgctggcg    420
ctgtttatcc acaccaccgg cgtgctctcc aagctgcttt ccgaagcggt ggaagcgatt    480
gagcccggcc cggtggaagg cattcgcgcc accggtgcca acaagctcga agagatcctc    540
tacggcgtgc tgccacaggt gatgccactg ctgatctcct actccctcta tcgcttcgaa    600
tccaacgtcc gctcggcgac cgtcgtcggc atggtcggcg caggcgggat cggcgtcacc    660
ctgtgggaag cgattcgcgg tttccagttc caacaaacct gcgccctgat ggtgcttatc    720
atcgtcacgg tcagcctgct ggatttcctc tctcaacggt tgcgtaagca ctttatctga    780

<210> SEQ ID NO 10
<211> LENGTH: 259
<212> TYPE: PRT
<213> ORGANISM: E.coli

<400> SEQUENCE: 10

Met Gln Thr Ile Thr Ile Ala Pro Pro Lys Arg Ser Trp Phe Ser Leu
1               5                   10                  15

Leu Ser Trp Ala Val Val Leu Ala Val Leu Val Val Ser Trp Gln Gly
                20                  25                  30

Ala Glu Met Ala Pro Leu Thr Leu Ile Lys Asp Gly Gly Asn Met Ala
                35                  40                  45

Thr Phe Ala Ala Asp Phe Phe Pro Pro Asp Phe Ser Gln Trp Gln Asp

```
            50                  55                  60
Tyr Leu Thr Glu Met Ala Val Thr Leu Gln Ile Ala Val Trp Gly Thr
 65                  70                  75                  80

Ala Leu Ala Val Val Leu Ser Ile Pro Phe Gly Leu Met Ser Ala Glu
                 85                  90                  95

Asn Leu Val Pro Trp Val Tyr Gln Pro Val Arg Arg Leu Met Asp
            100                 105                 110

Ala Cys Arg Ala Ile Asn Glu Met Val Phe Ala Met Leu Phe Val Val
            115                 120                 125

Ala Val Gly Leu Gly Pro Phe Ala Gly Val Leu Ala Leu Phe Ile His
            130                 135                 140

Thr Thr Gly Val Leu Ser Lys Leu Leu Ser Glu Ala Val Glu Ala Ile
145                 150                 155                 160

Glu Pro Gly Pro Val Glu Gly Ile Arg Ala Thr Gly Ala Asn Lys Leu
                165                 170                 175

Glu Glu Ile Leu Tyr Gly Val Leu Pro Gln Val Met Pro Leu Leu Ile
                180                 185                 190

Ser Tyr Ser Leu Tyr Arg Phe Glu Ser Asn Val Arg Ser Ala Thr Val
                195                 200                 205

Val Gly Met Val Gly Ala Gly Gly Ile Gly Val Thr Leu Trp Glu Ala
            210                 215                 220

Ile Arg Gly Phe Gln Phe Gln Gln Thr Cys Ala Leu Met Val Leu Ile
225                 230                 235                 240

Ile Val Thr Val Ser Leu Leu Asp Phe Leu Ser Gln Arg Leu Arg Lys
                245                 250                 255

His Phe Ile

<210> SEQ ID NO 11
<211> LENGTH: 2715
<212> TYPE: DNA
<213> ORGANISM: E.coli

<400> SEQUENCE: 11
atgcaaacga ttatccgtgt cgagaagctc gccaaaacct tcaatcagca tcaggcgctg      60
catgcggttg atctgaacat tcatcacggt gaaatggtgg ctctgcttgg gccgtcgggt     120
tccggaaaat ccaccctttt acgtcactta agcggtttga ttaccggcga taaatctgtc     180
ggtagccata tcgagctgct gggccgcaca gtccagcgcg aaggccgcct ggcccgcgat     240
atccgcaaaa gccgcgccca taccggctac atattccaac aattcaacct ggtgaaccgc     300
ctgagcgtac tggagaacgt gctgattggc gcgctcggca gcacgccgtt ctggcgcacc     360
tgttttagct ggttcaccgg cgagcagaaa cagcgcgcgt acaggcgct gacccgcgtt     420 ggcatggtgc attttgccca tcagcgcgtt tccaccctct ccggcggcca gcagcaacgt     480
gtggcgattg cccgtgcgct gatgcagcag gcgaaagtga ttctggccga tgaacccatc     540
gcctcgctgg acccagaatc agcgcgcatc gtgatggaca cctgcgcga catcaaccag     600 aacgacggca tcaccgtggg cgtcacgctg catcaggtgg attacgccct gctactgc      660 gaacgcatcg tcgccctgcg ccaggggcac gtcttctacg acggcagcag ccaacagttt     720
gataacgaac gttttgacca tctctaccgc agcattaacc gcgtcgaaga gaacgcgaaa     780
gctgcctgac atccccatca ttgaggaaaa cgaatgaacg ctaagataat tgcctcgctg     840
gccttcacca gcatgttcag cctcagcacc ctgttaagcc cggcgcacgc cgaagagcag     900
gaaaaggcgt tgaatttcgg cattatttca acggaatcac agcaaaacct gaaaccgcaa     960
```

```
tggacgccgt tcttgcagga tatggagaag aagctgggcg tgaaggtcaa cgccttcttt      1020
gccccggact acgcgggcat tatccagggg atgcgcttca ataaagtgga tatcgcctgg      1080
tacggcaatc tgtcggcgat ggaagcggtg gatcgcgcca atggccaggt cttcgcccag      1140
acggtcgcgg cggatggatc gccgggttac tggagcgtgt tgatcgtcaa caaagacagt      1200
ccgatcaaca acctgaacga tctgctggcg aagcggaaag atctcacctt tggcaatggc      1260
gatcctaact ccacctctgg cttcctcgtc cccggctact acgtcttcgc caaaaacaat      1320
atctccgcca gcgacttcaa gcgcaccgtc aacgccgggc atgaaaccaa cgcgctggcc      1380
gtcgccaaca gcaggtgga tgttgccacc aacaacaccg aaaacctcga caagctgaaa       1440
acctccgcgc cagagaagct gaaagaactg aaggtgatct ggaagtcgcc gctgatccca      1500
ggcgatccga tcgtctggcg caagaatctt tccgaaacca ccaaagacaa gatctacgac      1560
ttctttatga actacggcaa aacgccggaa gaaaagcgg tgctggaacg cctgggctgg       1620
gcgccattcc gcgcttccag cgacctgcaa ctggtgccga ttcgccagct cgcgctgttt      1680
aaagagatgc agggcgtgaa aagcaataaa ggactgaatg agcaggacaa gctggcaaaa      1740
accaccgaga ttcaggcgca gctggatgac ctggaccgcc tgaacaacgc gctaagcgcg      1800
atgagttcgg tgagtaaagc ggtgcagtaa atcgtaggtc ggataagacg ccccggcgtc      1860
gcatccgaca atgtgcaggc gttgatgccg gatgcggtgc aagcaccta tccgccgtac       1920 agaccggagc caaacatgca aaccatcacc atcgccccac ccaagcgcag ctggttctcg      1980
cttctgagct gggccgttgt actcgccgtg ttggtcgtct cgtggcaggg cgcggaaatg      2040
gccccgctta cgctgatcaa agacggcggc aacatggcga cgttcgccgc cgacttcttc      2100
ccgcccgatt tcagccagtg gcaggattac ctcaccgaaa tggccgtcac gctgcaaatc      2160
gccgtctggg gcaccgcgct ggcggtggtt ctctccatcc cctttggcct gatgagcgcc      2220
gaaaacctgg tgccgtggtg ggtttaccag cccgttcgcc gcctgatgga cgcctgccgc      2280
gccattaacg aaatggtctt cgccatgctg ttcgtggtcg ccgtcggcct cggcccgttc      2340
gctggcgtgc tggcgctgtt tatccacacc accggcgtgc tctccaagct gctttccgaa      2400
gcggtggaag cgattgagcc cggcccggtg gaaggcattc gcgccaccgg tgccaacaag      2460
ctcgaagaga tcctctacgg cgtgctgcca caggtgatgc cactgctgat ctcctactcc      2520
ctctatcgct tcgaatccaa cgtccgctcg gcgaccgtcg tcggcatggt cggcgcaggc      2580
gggatcggcg tcaccctgtg ggaagcgatt cgcggtttcc agttccaaca aacctgcgcc      2640
ctgatggtgc ttatcatcgt cacggtcagc ctgctggatt tcctctctca acggttgcgt      2700
aagcacttta tctga                                                      2715
```

<210> SEQ ID NO 12
<211> LENGTH: 1416
<212> TYPE: DNA
<213> ORGANISM: E.coli

<400> SEQUENCE: 12

```
gtgaaacaaa gcactattgc actggcactc ttaccgttac tgtttacccc tgtgacaaaa        60 gccccggacac cagaaatgcc tgttctggaa accgggctct cagggcga tattactgca        120 cccggcggtg ctcgccgttt aacgggtgat cagactgccg ctctgcgtga ttctcttagc       180
gataaacctg caaaaatat tattttgctg attggcgatg ggatggggga ctcggaaatt        240
actgccgcac gtaattatgc cgaaggtgcg ggcggctttt ttaaaggtat agatgcctta      300
```

```
ccgcttaccg ggcaatacac tcactatgcg ctgaataaaa aaaccggcaa accggactac    360
gtcaccgact cggctgcatc agcaaccgcc tggtcaaccg tgtcaaaac ctataacggc     420
gcgctgggcg tcgatattca cgaaaaagat cacccaacga ttctggaaat ggcaaaagcc    480
gcaggtctgg cgaccggtaa cgtttctacc gcagagttgc aggatgccac gcccgctgcg    540
ctggtggcac atgtgacctc gcgcaaatgc tacggtccga gcgcgaccag tgaaaaatgt    600
ccgggtaacg ctctggaaaa aggcggaaaa ggatcgatta ccgaacagct gcttaacgct    660
cgtgccgacg ttacgcttgg cggcggcgca aaaacctttg ctgaaacggc aaccgctggt    720
gaatggcagg gaaaaacgct gcgtgaacag gcacaggcgc gtggttatca gttggtgagc    780
gatgctgcct cactgaattc ggtgacggaa gcgaatcagc aaaaaccccct gcttggcctg    840
tttgctgacg gcaatatgcc agtgcgctgg ctaggaccga agcaacgta ccatggcaat     900
atcgataagc ccgcagtcac ctgtacgcca atccgcaac gtaatgacag tgtaccaacc     960
ctggcgcaga tgaccgacaa agccattgaa ttgttgagta aaatgagaa aggcttttc    1020
ctgcaagttg aaggtgcgtc aatcgataaa caggatcatg ctgcgaatcc ttgtgggcaa   1080
attggcgaga cggtcgatct cgatgaagcc gtacaacggg cgctggaatt cgctaaaaag   1140
gagggtaaca cgctggtcat agtcaccgct gatcacgccc acgccagcca gattgttgcg   1200
ccggatacca agctccgggg cctcacccag gcgctaaata ccaaagatgg cgcagtgatg   1260
gtgatgagtt acgggaactc cgaagaggat tcacaagaac ataccggcag tcagttgcgt   1320
attgcggcgt atggcccgca tgccgccaat gttgttggac tgaccgacca gaccgatctc   1380
ttctacacca tgaaagccgc tctggggctg aaataa                             1416
```

<210> SEQ ID NO 13
<211> LENGTH: 471
<212> TYPE: PRT
<213> ORGANISM: E.coli

<400> SEQUENCE: 13

```
Val Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Leu Glu Asn Arg
                20                  25                  30

Ala Ala Gln Gly Asp Ile Thr Ala Pro Gly Gly Ala Arg Arg Leu Thr
            35                  40                  45

Gly Asp Gln Thr Ala Ala Leu Arg Asp Ser Leu Ser Asp Lys Pro Ala
        50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
                100                 105                 110

Lys Lys Thr Gly Lys Pro Asp Tyr Val Thr Asp Ser Ala Ala Ser Ala
            115                 120                 125

Thr Ala Trp Ser Thr Gly Val Lys Thr Tyr Asn Gly Ala Leu Gly Val
        130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175
```

```
Thr Pro Ala Ala Leu Val Ala His Val Thr Ser Arg Lys Cys Tyr Gly
            180                 185                 190
Pro Ser Ala Thr Ser Glu Lys Cys Pro Gly Asn Ala Leu Glu Lys Gly
        195                 200                 205
Gly Lys Gly Ser Ile Thr Glu Gln Leu Leu Asn Ala Arg Ala Asp Val
    210                 215                 220
Thr Leu Gly Gly Gly Ala Lys Thr Phe Ala Glu Thr Ala Thr Ala Gly
225                 230                 235                 240
Glu Trp Gln Gly Lys Thr Leu Arg Glu Gln Ala Gln Ala Arg Gly Tyr
                245                 250                 255
Gln Leu Val Ser Asp Ala Ala Ser Leu Asn Ser Val Thr Glu Ala Asn
            260                 265                 270
Gln Gln Lys Pro Leu Leu Gly Leu Phe Ala Asp Gly Asn Met Pro Val
        275                 280                 285
Arg Trp Leu Gly Pro Lys Ala Thr Tyr His Gly Asn Ile Asp Lys Pro
    290                 295                 300
Ala Val Thr Cys Thr Pro Asn Pro Gln Arg Asn Asp Ser Val Pro Thr
305                 310                 315                 320
Leu Ala Gln Met Thr Asp Lys Ala Ile Glu Leu Leu Ser Lys Asn Glu
                325                 330                 335
Lys Gly Phe Phe Leu Gln Val Glu Gly Ala Ser Ile Asp Lys Gln Asp
            340                 345                 350
His Ala Ala Asn Pro Cys Gly Gln Ile Gly Glu Thr Val Asp Leu Asp
        355                 360                 365
Glu Ala Val Gln Arg Ala Leu Glu Phe Ala Lys Lys Glu Gly Asn Thr
    370                 375                 380
Leu Val Ile Val Thr Ala Asp His Ala His Ala Ser Gln Ile Val Ala
385                 390                 395                 400
Pro Asp Thr Lys Ala Pro Gly Leu Thr Gln Ala Leu Asn Thr Lys Asp
                405                 410                 415
Gly Ala Val Met Val Met Ser Tyr Gly Asn Ser Glu Glu Asp Ser Gln
            420                 425                 430
Glu His Thr Gly Ser Gln Leu Arg Ile Ala Ala Tyr Gly Pro His Ala
        435                 440                 445
Ala Asn Val Val Gly Leu Thr Asp Gln Thr Asp Leu Phe Tyr Thr Met
    450                 455                 460
Lys Ala Ala Leu Gly Leu Lys
465                 470

<210> SEQ ID NO 14
<211> LENGTH: 1011
<212> TYPE: DNA
<213> ORGANISM: Ralstonia sp. 4506

<400> SEQUENCE: 14
atgaagccca agtcgtcct cacccactgg gtgcacccgg aaatcatcga attgttgtcc      60
gctagcgccg atgttatccc caacaccaca cgggaaacct tgccgcgttc tgaggtaatt    120
gcgcgagcca agatgcggga tgcactcatg gctttcatgc cggacagcat cgacagcgcg    180
tttctcgagg aatgtccaaa gctgcgtgtc atcggcgccg cgcttaaagg ctatgataac    240
ttcgatgtca acgcctgcac acgccacggt gtatggctta cgattgtgcc ggatttgctt    300
acgatcccga ccgctgaact gactatcggc cttcttctcg gtttgacaag gcatatgctg    360
gaaggcgata ggcaaatccg tagcggacac ttccaaggct ggcggccgac actatatggc    420
```

```
tctggtttga caggaaaaac gcttggcatc attggtatgg gggcggtcgg ccgtgcaatc      480
gcccagcgct tggctggctt tgaaatgaat ctcttgtatt gcgatccgat tccgctcaat      540
gccgaacaag aaaaggcttg cacgtacag cgcgtcacgc tcgatgaact gctcgaaaaa       600
tgtgattatg tcgtgccgat ggttccgatg gccgcagaga cactgcatct gatcgatgcc      660
accgcgttgg ccaagatgaa aaccggtagc tacctgatca atgcatgtcg cggctcggtc      720
gtggatgaga atgcggtgat agcagcactg cgtctggaa aactagctgg atatgcagcc      780
gatgtcttcg agatggaaga atggatacgc gctgatcgcc cgcaggctat ccccaaggcg      840
ctgctcgaca atacggcaca aacgtttttt acgccgcatt tgggatcggc ggtcaaggaa      900
gttcggcttg aaatcgagcg gcaggcagcg atgaacatca tccaggcact cgctggtgaa      960
aaaccgatgg gcgcgattaa tcagccgtat ccgggagtaa aggcggcgtg a              1011
```

<210> SEQ ID NO 15
<211> LENGTH: 336
<212> TYPE: PRT
<213> ORGANISM: Ralstonia sp. 4506

<400> SEQUENCE: 15

```
Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
                20                  25                  30

Thr Leu Pro Arg Ser Glu Val Ile Ala Arg Ala Lys Asp Ala Asp Ala
            35                  40                  45

Leu Met Ala Phe Met Pro Asp Ser Ile Asp Ser Ala Phe Leu Glu Glu
        50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
    210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270
```

```
Arg Pro Gln Ala Ile Pro Lys Ala Leu Leu Asp Asn Thr Ala Gln Thr
            275                 280                 285

Phe Phe Thr Pro His Leu Gly Ser Ala Val Lys Glu Val Arg Leu Glu
        290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 16
<211> LENGTH: 819
<212> TYPE: DNA
<213> ORGANISM: Ralstonia sp. 4506

<400> SEQUENCE: 16
atgatcgaac tacagaatgt ctcagtcagt tatggtgatg cgattgcact gtatcccacc      60
actctcaaac tccatcaggg acagttcacc gtattgctcg atcttccgg cgctggaaaa     120 tccacgctac ttcgctgtat taattcgctg catgcgtcgc agcgcggcac caccattgtc     180
gccggcttag gaaatttggc gaactcgcgt gcattgcgca tgcatcgccg acagactggc     240
atggtgtttc aacagcatca attgattggc cgactgacgg cttgcaaaa cgtttcgatg     300 ggccgaatgg gctaccacac ggcattacgc agtctattcc ccctcccggc gaaggatcaa     360
tccatatgcc tgcaaagtct ggaccgagtc ggcttattgc acaaagcctt aagccgtgtc     420
gacgcattga gcggcggcca gcagcaacgc atcggtattg cccgggctct ggctcagcaa     480
cctaaactgg tgttggctga tgaaccggta gccagcctcg atcctgctac tgcagagcga     540
gtgctaagtc tgctgcaccg catttgtaaa gaggacggga tttcggcggt cgtcagcctg     600
catcaggtag acctcgctca acgttatgcc gaccgtatta ttggcctgtc ccatggccga     660 gtcattttg atgccgcccc gcagactttg atcaagcca gttacgacac gctgtatgaa     720
caagtacccc gttcttcttt gagcgttcca caagacgctc gagaggaacg gcttatcgat     780
acttcatttc ccatgcaact tgctaccgta aggattga                            819

<210> SEQ ID NO 17
<211> LENGTH: 272
<212> TYPE: PRT
<213> ORGANISM: Ralstonia sp. 4506

<400> SEQUENCE: 17

Met Ile Glu Leu Gln Asn Val Ser Val Ser Tyr Gly Asp Ala Ile Ala
1               5                   10                  15

Leu Tyr Pro Thr Thr Leu Lys Leu His Gln Gly Gln Phe Thr Val Leu
            20                  25                  30

Leu Gly Ser Ser Gly Ala Gly Lys Ser Thr Leu Leu Arg Cys Ile Asn
        35                  40                  45

Ser Leu His Ala Ser Gln Arg Gly Thr Thr Ile Val Ala Gly Leu Gly
    50                  55                  60

Asn Leu Ala Asn Ser Arg Ala Leu Arg Met His Arg Arg Gln Thr Gly
65                  70                  75                  80

Met Val Phe Gln Gln His Gln Leu Ile Gly Arg Leu Thr Ala Leu Gln
                85                  90                  95

Asn Val Ser Met Gly Arg Met Gly Tyr His Thr Ala Leu Arg Ser Leu
            100                 105                 110

Phe Pro Leu Pro Ala Lys Asp Gln Ser Ile Cys Leu Gln Ser Leu Asp
        115                 120                 125
```

```
Arg Val Gly Leu Leu His Lys Ala Leu Ser Arg Val Asp Ala Leu Ser
        130                 135                 140

Gly Gly Gln Gln Gln Arg Ile Gly Ile Ala Arg Ala Leu Ala Gln Gln
145                 150                 155                 160

Pro Lys Leu Val Leu Ala Asp Glu Pro Val Ala Ser Leu Asp Pro Ala
                165                 170                 175

Thr Ala Glu Arg Val Leu Ser Leu Leu His Arg Ile Cys Lys Glu Asp
            180                 185                 190

Gly Ile Ser Ala Val Val Ser Leu His Gln Val Asp Leu Ala Gln Arg
        195                 200                 205

Tyr Ala Asp Arg Ile Ile Gly Leu Ser His Gly Arg Val Ile Phe Asp
        210                 215                 220

Ala Ala Pro Gln Thr Leu Asp Gln Ala Ser Tyr Asp Thr Leu Tyr Glu
225                 230                 235                 240

Gln Val Pro Arg Ser Ser Leu Ser Val Pro Gln Asp Ala Arg Glu Glu
                245                 250                 255

Arg Leu Ile Asp Thr Ser Phe Pro Met Gln Leu Ala Thr Val Lys Asp
            260                 265                 270

<210> SEQ ID NO 18
<211> LENGTH: 861
<212> TYPE: DNA
<213> ORGANISM: Ralstonia sp. 4506

<400> SEQUENCE: 18
atgaaaaaac tcgcatccgc attattgtct gtcttgcttg ccgccgtctg cagcattggc      60
catgcatcat ccaatcccga tccagaaacg ctcaaagttg cgctgctgcc ggacgaaaac     120
gcatcgaccg taattaaaaa caacaagccg ctcgaaatct atctggaaaa agagctggga     180
aagaaaattg agctggtggt taccactgat tactcgtcaa tgatcgaagc catgcgtcac     240
ggccgtatcg acatggcata ttttggcccc ttgtcgtatg tgctggctaa gcaaaagagc     300
gacatcgagc cattcgcagc gatgaagcaa aagggtagca ctacctacca gtccgtattg     360
atcgccaata ctggcgccgg catcgccaaa atcagtgata tcgtcaacaa gaatgtcgct     420
tacggtgata aggcatccac ctccagccat ttgattccga agtcgatatt ggcggaaaac     480
ggtttgaaag ccggcgaaaa ctatcgcgaa cactttgtcg gtgcgcatga cgcggtggcc     540
atggccgtgc aaaacggtca cgcgcaggct ggcggcttga gtaagccgat ttttgaatcc     600
ctggttcagc gcggactggt cgatcccaac aaagtaaaag ttcttgccga atcgaagcca     660
tatccgcaat acccgtggac catgcgcagc aatctgaagc cggaactgaa ggaaaagatc     720
cgtgcagcct tcttgaatct caaagatccg gaagtcctga aacctttcaa agccgatggt     780 tcggcccga tcagcgacaa agactatgac gtggtgcgca gccttggcac actgctcaag     840
ctcgatctgt cgaagttcta a                                                861

<210> SEQ ID NO 19
<211> LENGTH: 286
<212> TYPE: PRT
<213> ORGANISM: Ralstonia sp. 4506

<400> SEQUENCE: 19

Met Lys Lys Leu Ala Ser Ala Leu Leu Ser Val Leu Leu Ala Ala Val
1               5                   10                  15

Cys Ser Ile Gly His Ala Ser Ser Asn Pro Asp Pro Glu Thr Leu Lys
            20                  25                  30
```

```
Val Ala Leu Leu Pro Asp Glu Asn Ala Ser Thr Val Ile Lys Asn Asn
             35                  40                  45

Lys Pro Leu Glu Ile Tyr Leu Glu Lys Glu Leu Gly Lys Lys Ile Glu
         50                  55                  60

Leu Val Val Thr Thr Asp Tyr Ser Ser Met Ile Glu Ala Met Arg His
 65                  70                  75                  80

Gly Arg Ile Asp Met Ala Tyr Phe Gly Pro Leu Ser Tyr Val Leu Ala
                 85                  90                  95

Lys Gln Lys Ser Asp Ile Glu Pro Phe Ala Ala Met Lys Gln Lys Gly
            100                 105                 110

Ser Thr Thr Tyr Gln Ser Val Leu Ile Ala Asn Thr Gly Ala Gly Ile
            115                 120                 125

Ala Lys Ile Ser Asp Ile Val Asn Lys Asn Val Ala Tyr Gly Asp Lys
130                 135                 140

Ala Ser Thr Ser Ser His Leu Ile Pro Lys Ser Ile Leu Ala Glu Asn
145                 150                 155                 160

Gly Leu Lys Ala Gly Glu Asn Tyr Arg Glu His Phe Val Gly Ala His
                165                 170                 175

Asp Ala Val Ala Met Ala Val Gln Asn Gly His Ala Gln Ala Gly Gly
            180                 185                 190

Leu Ser Lys Pro Ile Phe Glu Ser Leu Val Gln Arg Gly Leu Val Asp
            195                 200                 205

Pro Asn Lys Val Lys Val Leu Ala Glu Ser Lys Pro Tyr Pro Gln Tyr
        210                 215                 220

Pro Trp Thr Met Arg Ser Asn Leu Lys Pro Glu Leu Lys Glu Lys Ile
225                 230                 235                 240

Arg Ala Ala Phe Leu Asn Leu Lys Asp Pro Glu Val Leu Lys Pro Phe
                245                 250                 255

Lys Ala Asp Gly Phe Gly Pro Ile Ser Asp Lys Asp Tyr Asp Val Val
            260                 265                 270

Arg Ser Leu Gly Thr Leu Leu Lys Leu Asp Leu Ser Lys Phe
        275                 280                 285

<210> SEQ ID NO 20
<211> LENGTH: 798
<212> TYPE: DNA
<213> ORGANISM: Ralstonia sp. 4506

<400> SEQUENCE: 20
atgcaagctg attttggttt gattctggcc gagcgccagc gcgtatggaa ccgcacgata      60
ctgcagtttg ccgttgtgct ggcgattgtg atcggttgct ggtattacgt cggcctattt     120
gatgccgagc gattgaagga tggcatgcca agcctggtaa aaattgccgg cgagatgttc     180
ccaccgaact tctcgcaggc tggcacctgg gtcaaaccgg tactggatac cttggccatg     240
agtatcgccg gtacggcaat cgcggtattg ctatccattc ccttaggagt gctcgccgcg     300
cggaatacta gccctcatcc actcgtgtat caagccacac gcggcctgtt aaacgctttg     360
cgatcgatac ccgaactgat catgggcatc ctgttcgtgg cagccgttgg cttcggcgca     420
ttgccgggtg ttttagccct aggcttacat tcggttggca tgatcgccaa atttttttcg     480
gaatcgatcg aacatgccga tccggcaccg gtagaagccg cgcatgcagc gggctgcacg     540
ccattgcagg tgattttca tgggatcttt ccccaagtgc ttccgcaaat ggccgatacc     600
gcgatctatc gatgggaata caacttccgt gcttcgaccg tgatgggcat ggtcggcgcc     660
```

```
ggtggaatcg ggttcgagct gatgggctct ctgcgcatca tgcaatacca ggatgtctcg      720
gctattttgc tggttatttt aggcatggtt accctcgtcg acgccttcag ctccttcctg      780
cgtcgcaagt tcaaataa                                                    798
```

<210> SEQ ID NO 21
<211> LENGTH: 265
<212> TYPE: PRT
<213> ORGANISM: Ralstonia sp. 4506

<400> SEQUENCE: 21

```
Met Gln Ala Asp Phe Gly Leu Ile Leu Ala Glu Arg Gln Arg Val Trp
1               5                   10                  15

Asn Arg Thr Ile Leu Gln Phe Ala Val Val Leu Ala Ile Val Ile Gly
            20                  25                  30

Cys Trp Tyr Tyr Val Gly Leu Phe Asp Ala Glu Arg Leu Lys Asp Gly
        35                  40                  45

Met Pro Ser Leu Val Lys Ile Ala Gly Glu Met Phe Pro Pro Asn Phe
    50                  55                  60

Ser Gln Ala Gly Thr Trp Val Lys Pro Val Leu Asp Thr Leu Ala Met
65                  70                  75                  80

Ser Ile Ala Gly Thr Ala Ile Ala Val Leu Leu Ser Ile Pro Leu Gly
                85                  90                  95

Val Leu Ala Ala Arg Asn Thr Ser Pro His Pro Leu Val Tyr Gln Ala
            100                 105                 110

Thr Arg Gly Leu Leu Asn Ala Leu Arg Ser Ile Pro Glu Leu Ile Met
        115                 120                 125

Gly Ile Leu Phe Val Ala Ala Val Gly Phe Gly Ala Leu Pro Gly Val
    130                 135                 140

Leu Ala Leu Gly Leu His Ser Val Gly Met Ile Ala Lys Phe Phe Ser
145                 150                 155                 160

Glu Ser Ile Glu His Ala Asp Pro Ala Pro Val Glu Ala Ala His Ala
                165                 170                 175

Ala Gly Cys Thr Pro Leu Gln Val Ile Phe His Gly Ile Phe Pro Gln
            180                 185                 190

Val Leu Pro Gln Met Ala Asp Thr Ala Ile Tyr Arg Trp Glu Tyr Asn
        195                 200                 205

Phe Arg Ala Ser Thr Val Met Gly Met Val Gly Ala Gly Gly Ile Gly
    210                 215                 220

Phe Glu Leu Met Gly Ser Leu Arg Ile Met Gln Tyr Gln Asp Val Ser
225                 230                 235                 240

Ala Ile Leu Leu Val Ile Leu Gly Met Val Thr Leu Val Asp Ala Phe
                245                 250                 255

Ser Ser Phe Leu Arg Arg Lys Phe Lys
            260                 265
```

<210> SEQ ID NO 22
<211> LENGTH: 3758
<212> TYPE: DNA
<213> ORGANISM: Ralstonia sp. 4506

<400> SEQUENCE: 22

```
atagcaggcg tctatatttg gcatagatag cacaacttat ttccctcaca ggcacccgcg       60
accatgtctc aaaaatgaca tcaacgagtc atcagggtgt catatcacga cattaccatc      120
gctgcaattc agattcgtaa tcaggtcatc attttgatt acgatttcaa atctgccgga      180
```

-continued

```
ggtgtcatga tcgaactaca gaatgtctca gtcagttatg gtgatgcgat tgcactgtat    240
cccaccactc tcaaactcca tcagggacag ttcaccgtat tgctcggatc ttccggcgct    300
ggaaaatcca cgctacttcg ctgtattaat tcgctgcatg cgtcgcagcg cggcaccacc    360
attgtcgccg gcttaggaaa tttggcgaac tcgcgtgcat tgcgcatgca tcgccgacag    420
actggcatgg tgtttcaaca gcatcaattg attggccgac tgacggcttt gcaaaacgtt    480
tcgatgggcc gaatgggcta ccacacggca ttacgcagtc tattccccct cccggcgaag    540
gatcaatcca tatgcctgca aagtctggac cgagtcggct tattgcacaa agccttaagc    600
cgtgtcgacg cattgagcgg cggccagcag caacgcatcg gtattgcccg ggctctggct    660
cagcaaccta aactggtgtt ggctgatgaa ccggtagcca gcctcgatcc tgctactgca    720
gagcgagtgc taagtctgct gcaccgcatt tgtaaagagg acgggatttc ggcggtcgtc    780
agcctgcatc aggtagacct cgctcaacgt tatgccgacc gtattattgg cctgtcccat    840
ggccgagtca ttttgatgc cgccccgcag actttggatc aagccagtta cgacacgctg    900
tatgaacaag taccccgttc ttctttgagc gttccacaag acgctcgaga ggaacggctt    960
atcgatactt catttcccat gcaacttgct accgtaaagg attgattatg aaaaaactcg   1020
catccgcatt attgtctgtc ttgcttgccg ccgtctgcag cattggccat gcatcatcca   1080
atcccgatcc agaaacgctc aaagttgcgc tgctgccgga cgaaaacgca tcgaccgtaa   1140
ttaaaaacaa caagccgctc gaaatctatc tggaaaaaga gctgggaaag aaaattgagc   1200
tggtggttac cactgattac tcgtcaatga tcgaagccat gcgtcacggc cgtatcgaca   1260
tggcatattt tggccccttg tcgtatgtgc tggctaagca aaagagcgac atcgagccat   1320
tcgcagcgat gaagcaaaag ggtagcacta cctaccagtc cgtattgatc gccaatactg   1380
gcgccggcat cgccaaaatc agtgatatcg tcaacaagaa tgtcgcttac ggtgataagg   1440
catccacctc cagccatttg attccgaagt cgatattggc ggaaaacggt ttgaaagccg   1500
gcgaaaacta tcgcgaacac tttgtcggtg cgcatgacgc ggtggccatg ccgtgcaaa    1560 acggtcacgc gcaggctggc ggcttgagta gccgatttt tgaatccctg gttcagcgcg   1620
gactggtcga tcccaacaaa gtaaaagttc ttgccgaatc gaagccatat ccgcaatacc   1680
cgtggaccat gcgcagcaat ctgaagccgg aactgaagga aaagatccgt gcagccttct   1740
tgaatctcaa agatccggaa gtcctgaaac ctttcaaagc cgatggtttc ggcccgatca   1800
gcgacaaaga ctatgacgtg gtgcgcagcc ttggcacact gctcaagctc gatctgtcga   1860
agttctaagt gagcgacagc atgcaagctg attttggttt gattctggcc gagcgccagc   1920
gcgtatggaa ccgcacgata ctgcagtttg ccgttgtgct ggcgattgtg atcggttgct   1980
ggtattacgt cggcctatt gatgccgagc gattgaagga tggcatgcca agcctggtaa   2040
aaattgccgg cgagatgttc ccaccgaact tctcgcaggc tggcacctgg gtcaaaccgg   2100
tactggatac cttggccatg agtatcgccg gtacggcaat cgcggtattg ctatccattc   2160
ccttaggagt gctcgccgcg cggaatacta gccctcatcc actcgtgtat caagccacac   2220
gcggcctgtt aaacgctttg cgatcgatac ccgaactgat catgggcatc ctgttcgtgg   2280
cagccgttgg cttcggcgca ttgccggtg tttagccct aggcttacat tcggttggca   2340
tgatcgccaa attttttcg gaatcgatcg aacatgccga tccggcaccg gtagaagccg   2400
cgcatgcagc gggctgcacg ccattgcagg tgattttca tgggatcttt ccccaagtgc   2460
ttccgcaaat ggccgatacc gcgatctatc gatgggaata caacttccgt gcttcgaccg   2520
tgatgggcat ggtcggcgcc ggtggaatcg ggttcgagct gatgggctct ctgcgcatca   2580
```

-continued

```
tgcaatacca ggatgtctcg gctatttttgc tggttattttt aggcatggtt accctcgtcg    2640
acgccttcag ctccttcctg cgtcgcaagt tcaaataact cccaaagctt acaaggtttt     2700
ttatgaagcc caaagtcgtc ctcacccact gggtgcaccc ggaaatcatc gaattgttgt     2760
ccgctagcgc cgatgttatc cccaacacca cacgggaaac cttgccgcgt tctgaggtaa     2820
ttgcgcgagc caaagatgcg gatgcactca tggctttcat gccggacagc atcgacagcg     2880
cgtttctcga ggaatgtcca aagctgcgtg tcatcggcgc cgcgcttaaa ggctatgata     2940
acttcgatgt caacgcctgc acacgccacg tgtatggct tacgattgtg ccggatttgc      3000
ttacgatccc gaccgctgaa ctgactatcg gccttcttct cggtttgaca aggcatatgc     3060
tggaaggcga taggcaaatc cgtagcggac acttccaagg ctggcggccg acactatatg     3120
gctctggttt gacaggaaaa acgcttggca tcattggtat gggggcggtc ggccgtgcaa     3180
tcgcccagcg cttggctggc tttgaaatga atctcttgta ttgcgatccg attccgctca     3240
atgccgaaca agaaaaggct tggcacgtac agcgcgtcac gctcgatgaa ctgctcgaaa     3300
aatgtgatta tgtcgtgccg atggttccga tggccgcaga gacactgcat ctgatcgatg     3360
ccaccgcgtt ggccaagatg aaaaccggta gctacctgat caatgcatgt cgcggctcgg     3420
tcgtggatga gaatgcggtg atagcagcac tggcgtctgg aaaactagct ggatatgcag     3480
ccgatgtctt cgagatggaa gaatggatac gcgctgatcg cccgcaggct atccccaagg     3540
cgctgctcga caatacggca caaacgtttt ttacgccgca tttgggatcg gcggtcaagg     3600
aagttcggct tgaaatcgag cggcaggcag cgatgaacat catccaggca ctcgctggtg     3660
aaaaaccgat gggcgcgatt aatcagccgt atccgggagt aaaggcggcg tgatagatct     3720
ggagcgtgtg gcgacgttca ttgccgtcgt caaatgcg                              3758
```

<210> SEQ ID NO 23
<211> LENGTH: 8234
<212> TYPE: DNA
<213> ORGANISM: E.coli

<400> SEQUENCE: 23

```
attctggccg gctaacccgg tcacatggga tgaggagata acataatctc cctcccacaa     60
gcagtaacta taaaaataac cccactctct acaaggctcg gggcgcccga aaaacgggc     120 atacaggttg accgacaacg atataaatcg gaatcaaaaa ctatgtgtgg aattgttggc    180
gcgatcgcgc aacgtgatgt agcagaaatc cttcttgaag gtttacgtcg tctggaatac    240
cgcggatatg actctgccgg tctggccgtt gttgatgcag aaggtcatat gacccgcctg    300
cgtcgcctcg gtaaagtcca gatgctggca caggcagcgg aagaacatcc tctgcatggc    360
ggcactggta ttgctcacac tcgctgggcg acccacggtg aaccttcaga agtgaatgcg    420
catccgcatg tttctgaaca cattgtggtg gtgcataacg gcatcatcga aaccatgaa     480 ccgctgcgtg aagagctaaa agcgcgtggc tataccttcg tttctgaaac cgacaccgaa    540
gtgattgccc atcggtgaa ctgggagctg aaacaaggcg ggactctgcg tgaggccgtt     600
ctgcgtgcta tcccgcagct gcgtggtgcg tacggtacag tgatcatgga ctcccgtcac    660
ccggataccc tgctggcggc acgttctggt agtccgctgg tgattggcct ggggatgggc    720
gaaaacttta tcgcttctga ccagctggcg ctgttgccgg tgacccgtcg ctttatcttc    780
cttgaagagg gcgatattgc ggaaatcact cgccgttcgg taaacatctt cgataaaact    840
ggcgcggaag taaaacgtca ggatatcgaa tccaatctgc aatatgacgc gggcgataaa    900
```

-continued

```
ggcatttacc gtcactacat gcagaaagag atctacgaac agccgaacgc gatcaaaaac    960
acccttaccg gacgcatcag ccacggtcag gttgatttaa gcgagctggg accgaacgcc   1020
gacgaactgc tgtcgaaggt tgagcatatt cagatcctcg cctgtggtac ttcttataac   1080
tccggtatgt tttcccgcta ctggtttgaa tcgctagcag gtattccgtg cgacgtcgaa   1140
atcgcctctg aattccgcta tcgcaaatct gccgtgcgtc gtaacagcct gatgatcacc   1200
ttgtcacagt ctggcgaaac cgcggatacc ctggctggcc tgcgtctgtc gaaagagctg   1260
ggttaccttg gttcactggc aatctgtaac gttccgggtt cttctctggt gcgcgaatcc   1320
gatctggcgc taatgaccaa cgcgggtaca gaaatcggcg tggcatccac taaagcattc   1380
accactcagt taactgtgct gttgatgctg gtggcgaagc tgtctcgcct gaaaggtctg   1440
gatgcctcca ttgaacatga catcgtgcat ggtctgcagg cgctgccgag ccgtattgag   1500
cagatgctgt ctcaggacaa acgcattgaa gcgctggcag aagatttctc tgacaaacat   1560
cacgcgctgt tcctgggccg tggcgatcag tacccaatcg cgctggaagg cgcattgaag   1620
ttgaaagaga tctcttacat tcacgctgaa gcctacgctg ctggcgaact gaaacacggt   1680
ccgctggcgc taattgatgc cgatatgccg gttattgttg ttgcaccgaa caacgaattg   1740
ctggaaaaac tgaaatccaa cattgaagaa gttcgcgcgc gtggcggtca gttgtatgtc   1800
ttcgccgatc aggatgcggg ttttgtaagt agcgataaca tgcacatcat cgagatgccg   1860
catgtggaag aggtgattgc accgatcttc tacaccgttc cgctgcagct gctggcttac   1920
catgtcgcgc tgatcaaagg caccgacgtt gaccagccgc gtaacctggc aaaatcggtt   1980
acggttgagt aataaatgga tgccctgcgt aagcggggca ttttcttcc tgttatgttt   2040
ttaatcaaac atcctgccaa ctccatgtga caaaccgtca tcttcggcta ctttttctct   2100
gtcacagaat gaaaattttt ctgtcatctc ttcgttatta atgtttgtaa ttgactgaat   2160
atcaacgctt atttaaatca gactgaagac tttatctctc tgtcataaaa ctgtcatatt   2220
ccttacatat aactgtcacc tgtttgtcct attttgcttc tcgtagccaa caaacaatgc   2280
tttatgaatc ctcccaggag acattatgaa agttatgcgt accaccgtcg caactgttgt   2340
cgccgcgacc ttatcgatga gtgctttctc tgtgtttgca gaagcaagcc tgacaggtgc   2400
aggtgcaacc ttccctgcgc cggtgtatgc caaatgggct gacacttacc agaaagaaac   2460
cggtaataaa gttaactacc agggtatcgg ttcttccggt ggcgtaaaac agattatcgc   2520
taataccgtt gattttggtg cctctgacgc gccgctgtct gacgaaaaac tggctcagga   2580
aggtctgttc cagttcccga ccgtgattgg cggcgtggtg ctggcggtta acattccagg   2640
gctgaagtct ggcgaactgg tgctggatgg taaaaccctc ggcgacatct acctgggcaa   2700
aatcaagaag tgggatgatg aagccatcgc caaactgaat ccgggtctga actgccttc   2760
acaaaacatt gctgtagtac gccgcgcaga tggctccggg acttccttcg tcttcaccag   2820
ctacctggcg aaagtgaacg aagagtggaa aaacaacgtt ggtactggct ctaccgtaaa   2880
atggccgatc ggtctgggcg gtaaaggtaa cgacggtatc gccgcgttcg ttcagcgtct   2940
gccgggtgca attggttatg ttgaatatgc ttacgcgaag cagaacaacc tggcgtacac   3000
caaactgatc tccgctgatg gtaaaccggt tagtccgacc gaagaaaact cgctaatgc   3060
agcaaaaggt gcagactgga gcaaaacctt cgctcaggat ctgaccaacc agaaaggcga   3120
agatgcatgg cctattacct ctaccacgtt cattctgatc cacaaagatc agaagaaacc   3180
agaacaaggc acagaagtgc tgaaattctt cgactgggcg tacaaaaccg ggctaaaaca   3240
ggcgaacgac ctggattacg ccagcctgcc ggatagtgta gttgaacagg ttcgcgctgc   3300
```

```
gtggaagacc aatattaaag acagtagcgg taagccgctg tactaataaa actccaggcc    3360
gggtacggtg ttttacgccg catccggcat tacaaaatga ctttgtaaac gcgtttaact    3420
gaagagtaac ttatggctgc aaccaagcct gcttttaacc caccgggtaa aaagggcgac    3480
ataattttca gcgtgctggt aaaactggcg gcgctgattg tgctattgat gttgggtggc    3540
attattgtct ctctgatcat ctcctcctgg ccgagcattc agaaatttgg tctggctttc    3600
ctatggacca aagagtggga tgcaccgaac gatatctacg gggcgctggt gccgatctac    3660
ggtacgttgg tgacttcgtt tatcgcgctg ctgatcgccg tcccggtgag tttcggtatc    3720
gccctgttcc tgactgagct gcgcctggc tggctgaaac gcccgctggg tatcgccatt    3780
gagctgctgg cagccattcc aagtatcgtt tacggcatgt ggggcctgtt tatctttgcg    3840
ccgctgttcg ccgtttactt tcaggagccg gtcggcaata tcatgtcgaa tatcccgatt    3900
gttggcgcgc tgttctctgg ccccgcattt ggtatcggta tcctcgcggc aggcgtgatc    3960
ctcgccatca tgattattcc gtacattgcg gcggtaatgc gtgatgtgtt cgaacaaacc    4020
ccggtgatga tgaaagagtc ggcctacggt attggctgca ccacctggga agttatctgg    4080
cgtatcgttc ttccgttcac caaaaatggt gttatcggcg gcatcatgct ggggctgggc    4140
cgcgcgctcg gtgaaaccat ggcggtgacc tttatcatcg gtaacaccta ccagctcgac    4200
agcgcctcgc tgtatatgcc gggcaacagt atcacctctg cgctggcgaa cgaatttgcg    4260
gaagcggaat ccggtctgca cgttgccgca ctgatggaac tgggcctgat cctgtttgtg    4320
attaccttca tcgtcctcgc cgcatcgaag tttatgatta tgcgcctggc taagaatgag    4380
ggggcacgct aatggctatg gttgaaatgc aaaccactgc ggcgctggct gaatctcgcc    4440
gcaaaatgca ggcgcgtcgc cgcctcaaaa accgtattgc gctgacgctc tcgatggcga    4500
cgatggcctt cggcctgttc tggctgatct ggattttaat gtccaccatc actcgcggta    4560
tcgacggtat gtcgctggcg ctgttcactg aaatgacgcc gccgcccaat acggaaggtg    4620
gtggtctggc gaacgctctg gcgggtagcg ggctgttaat tttgtgggcc acggtattcg    4680
gtacgccgct gggcattatg gcggggattt atctggcgga atatggtcgt aaatcctggc    4740
tggcagaagt gattcgcttc attaacgaca ttctgctctc tgcgccgtcg attgtggttg    4800
gtctgtttgt ttacaccatt gtggtggcgc agatggagca cttctccggc tgggcgggcg    4860
tgattgccct ggcgttgttg caggtgccga ttgttatccg caccaccgag aacatgctga    4920
aactggtgcc gtacagcctg cgtgaagcgg cttatgcgct gggtacaccg aagtggaaga    4980
tgatctctgc gattacgctg aaagcgtcgg tgtccgggat tatgaccggt atcctgctgg    5040
cgattgcccg tattgctggt gaaaccgcgc cgctgctgtt taccgcgctc tccaaccagt    5100
tctggagcac ggacatgatg cagccgatcg ccaacctgcc ggtgacgatc tttaagtttg    5160
cgatgagccc gtttgcggaa tggcagcaat tggcctgggc cggggtattg atcattaccc    5220
tgtgcgtact gctgctgaac attctggcgc gcgttgtttt tgcgaagaat aaacacggtt    5280
gatattgctg acacggtttt cccctcaccc taaccctctc cccagagggg cgagggacc    5340 gaccgagcgc ctttttgact ctgtacacgg ttaacacttt gccggatgcg gcgtgaacgc    5400
ctgatccggc ctacggtaag cctgattagc gaagtgcatc aggcacgatg aggaaaagat    5460
tgcaatgagt atggttgaaa ctgccccgag taaaattcag gttcgtaatt tgaacttcta    5520
ctacggcaaa ttccatgccc tgaaaaacat caacctggat atcgctaaaa accaggtaac    5580
ggcgtttatc gggccgtccg gctgcggtaa atcgacgctg ctgcgtacct tcaacaaaat    5640
```

```
gtttgaactg tacccggagc agcgtgcgga aggtgaaatt ctgcttgatg gcgacaacat   5700
cctgaccaac tctcaggata tcgcactgct gcgtgcgaaa gtgggcatgg tgttccagaa   5760
accgacgccg tttccgatgt ccatctacga acatcgct tttggcgttc gtctgtttga   5820
gaagctctcc cgtgccgaca tggacgagcg cgtgcagtgg gcattgacca aagccgcatt   5880
gtggaacgaa accaaagata aattgcacca gagcggttac tctctctctg gtggtcagca   5940
acagcgtctg tgtattgcgc gtggtatcgc cattcgcccg gaagtgctgc tgctcgacga   6000
accgtgttcg gcgctcgacc ctatctctac cgggcgtatt gaagagctga tcaccgaact   6060
gaagcaggat tacaccgtgg tgatcgtcac ccacaacatg cagcaggctg cgcgttgttc   6120
cgaccacacg gcgtttatgt acctgggcga attgattgag ttcagcaaca cggacgatct   6180
gttcaccaag ccagcgaaga aacaaacaga agactacatc accggtcgtt acggttgatt   6240
caggagtgcg ttatggacag tctcaatctt aataaacata tttccggcca gttcaacgcc   6300
gaactggaaa gtatccgcac gcaggtgatg accatgggcg gcatggtgga gcagcagctt   6360
tctgatgcaa tcaccgcgat gcataaccag gacagcgatc tggcgaagcg cgtcatcgaa   6420
ggcgacaaga acgtcaacat gatggaagtg gcgatcgatg aagcctgcgt gcgcattatc   6480
gccaaacgtc agccgacggc gagcgacctg cgactggtta tggtgatcag taaaaccatt   6540
gccgagctgg agcgtattgg cgacgtggcg gacaaaatct gccgtactgc gctggagaaa   6600
ttctcccagc agcatcagcc gttgctggta agtctggagt cgctgggccg tcataccatc   6660
cagatgctgc acgacgtgct ggacgcgttc gcgcggatgg acattgacga agcggtacgt   6720
atttatcgtg aagataaaaa agtcgatcag gaatacgaag gtattgttcg tcaactgatg   6780
acctacatga tggaagattc gcgtaccatt ccgagcgtac ttactgcgct gttctgcgcg   6840
cgttctatcg aacgtattgg cgaccgctgc cagaatattt gtgagtttat cttctactac   6900
gtgaaggggc aggatttccg tcacgtcggt ggcgatgagc tggataaact gctggcgggg   6960
aaagatagcg acaaataatt caccagacaa atcccaataa cttaattatt gggatttgtt   7020
atatataact ttataaattc ctaaaattac acaagttaa taactgcgag catggtcata   7080
tttttatcaa tagcgcattg ctattttctc tgcacgcaat taaattaatt tccgaacctg   7140
gatgttcgtt ataaaaacca ttaataaatg actggattgt tactgcattc gcaggcaaaa   7200
cctgacataa ccagagaata ctggtgaagt cgggtttttt tgtttataaa aaaggtcctt   7260
gctatgaaca tgcaaatcac caaaattctc aacaataatg ttgtggtggt tattgatgat   7320
caacagcggg aaaagtcgt catggggcgc ggaattggct ttcaaaaacg cgctggcgaa   7380
agaattaact caagtggaat agaaaaagag tatgccttga gcagtcatga actgaacggg   7440
cgattaagcg aactcttaag tcatattcct cttgaggtga tggcaacctg tgatcgtatt   7500
atctctttag cgcaggagcg cttgggaaaa ttacaggaca gtatttatat ctcgctaact   7560
gaccattgcc agtttgcgat taaacgcttt cagcaaaacg tgttgctgcc caacccgttg   7620
ctgtgggata tccagcggct ttacccgaaa gagttccagc taggggaaga agcgttaacc   7680
attattgata acggttggg cgtgcagtta ccgaaagatg aagtgggctt tattgccatg   7740
catctggtca gtgcccaaat gagcggaaat atggaggatg ttgcaggtgt cacgcagtta   7800
atgcgcgaaa tgctgcaatt aataaaattt cagttcagcc ttaattacca ggaagaaagc   7860
ttgagttatc agcgactggt tacacatctg aagttttat cctggcgtat tcttgaacat   7920
gcttcaatta acgatagtga tgaatcatta caacaagcag taaaacaaaa ttacccgcaa   7980
gcatggcaat gtgcggaacg gatcgccatt tttattggtt tgcagtatca acgtaaaatt   8040
```

-continued

| | | |
|---|---|---|
| tcacccgcag agattatgtt tttagccata aatatagagc gcgtgcgcaa agaacactga | 8100 |
| aatattatta ctgagtaaag gattgttacc gcactaagcg ggcaaaacct gaaaaaaatt | 8160 |
| gcttgattca cgtcaggccg ttttttttcag gtttttttttt ggagttttgc cgcaaagcgg | 8220 |
| tagagggcaa gtta | 8234 |

<210> SEQ ID NO 24
<211> LENGTH: 14979
<212> TYPE: DNA
<213> ORGANISM: Pseudomonas stutzeri WM88

<400> SEQUENCE: 24

| | | |
|---|---|---|
| gctagcaagc cggttttcaa gctcggggtg ggcgaccttg gccgccgcgc gcagaccgtc | 60 |
| cgtgggctcc acgccgtagg cttcgtagcc gctcttgagg aggtgcgcca agtcacgacc | 120 |
| agatcctgcc ccgatatcaa gcaaccgggc ccctggcaca aatgccagcg ggaagtactt | 180 |
| ggccacaggg ctgcccaccg attcgtaccg ggtggctatg tcctgggcgt tgtcttcgta | 240 |
| gaagcgagcc gtcgatgcgt ccatggagcg gtcactcaga agggttatgt ataccctaagt | 300 |
| ttgtaaactt ctaaatttcc ccagcaacaa tggggctttt ctcaataggg agagcactga | 360 |
| gaaaaagttt atgtaaacaa atgccgaccg accaacgagg ttgtttacag tcctccacga | 420 |
| acccgtgaag cgtataggct tgaatggaca ggcaggaact atacaactgg cagatcaagc | 480 |
| ttgacaccga agtgccccgc atccgcaggt gaacggtgcc acccgccgac tatcattgca | 540 |
| tcacacttac agacgatctg cgcatggccc aattgtttta attgctttcg ataaaggcgc | 600 |
| gcattctgtc gcgacagata ccctactctc tgtccttcaa tagtcactcg aacggctcga | 660 |
| ttgtcatgcg gattggaatc ctccaagtaa aggatggcct ctgtcacata ctcggcgccg | 720 |
| tcctctgagc gaccgccact gatggcaccg catgcactcc tccacaatgg ccctggtggt | 780 |
| gtgccagtca tctgaggccg cattccagcg aattatctcg tcgggtgtgg tgtacgcctc | 840 |
| ccacacccgt tcaatcgggg ctcgtacgtt cgtctcgacg gtgagttgca tagcggctct | 900 |
| ctccagtttg gtggcagcgg gttgttcact gccatttgcg ggggtgaaca gcagatatta | 960 |
| tcgtgcaaag gcctattgtg acgtaggcag aaagcgacac gggcggcgct tgccaggcgc | 1020 |
| tgcgaccatc cttctgtgtt gcattccgcg tcccgctgtc atgcctatgt cataccgacg | 1080 |
| atctaccatc ctttcatgat cgatctgtag atcaaagtta attattgatt acatgatcga | 1140 |
| atcagcatgc cggaaggagc cgcagtttgc cctcccgatt attcgttgga agaccttgga | 1200 |
| gcatcaccat gtttgcagag cagcaacgcg aatatctcga caaggatat acgaagattg | 1260 |
| aaagcttttt ctccgcggag gaagtagcga agattcttga agacgtcaag caaattgaat | 1320 |
| tgggagctat tggcgtagct tcggacaatg agacttacca gttcgaaaag aagaatggcg | 1380 |
| agacgacgaa gctactgcgt cgcgtcgaga atcctcacct ttatttcgat gcaatagatt | 1440 |
| ctttggtcag gtcggaaaaa atcgtcgatt tgcttcggca tttcctgggc gaaaacatcc | 1500 |
| gtttgcacaa tagcaaaatc aacttcaagc cgccatcagg cgcgccagtc cagtggcatc | 1560 |
| aggactgggc attctatccc cacacaaacg atgattttct tactctcgga atttcctcg | 1620 |
| acgagacaag tgagaaaaat ggcgcgatgg catgcttgcc aggctccac aaaggaaaag | 1680 |
| tgtacgacca ccggaacgtc gagacgggcg agttttgcca cgcgatctct cgctccaact | 1740 |
| gggacgaagc gctcgacccg acagaagggg agttactgac gggacccgta ggaactgtca | 1800 |
| cgttgcatca cgtccggacc cttcatggtt caggcccaaa ccactcaacg atcaggcggc | 1860 |

```
gttttctgct catcggctat gccgcggctg atgcctggcc acttctgggc tgtggcaact    1920
atggggatta tgaaagcctc atggtctctg gccgatccac cgtattcccg cgcatggtgg    1980
aactcccttt gactgtcccg tatccgttgt cgatgtacgg tgatcgcatc tttgaaagtc    2040
aacgagcttt gactcaaaag tactactgaa gtctttaact cactgaggtc ataatgcaag    2100
tttttactct gttttcgaaa ttcaagaagg cgttaacgcg cgccattctt gcctttatcg    2160
ccacaatcat agtgtgcaca cccgcgcagg cagctgaggt tgtcaatggt aaacttcacc    2220
tgcgttttgc aattgcgccg atgcgtccaa cgcctagcca gaccatcaaa gagtttgagc    2280
cgatattcaa gtatctcgcc gaccagctcg gcgcgaccta tgaaatcgtc tccccggaaa    2340
gctgggcggc aatatctgtg gcaatgacaa atggccatgt cgatgtgggc tggctcggac    2400
cctgggcta tgtcttgtcg aataaaaagg ccggcaccga agtgcttgca acggtcaagt    2460
accgcgggga gccgttctac aaagccctca ttgtcggtcg cgccgatctg ccgatcaaaa    2520
aatggcccga ggacgcgaag ggtttgaagc tgtcactcag tgatcagggc aacacttctg    2580
gctggctcat cccgatggcg tacttcaaga gcatcggcat cgaccctgcg agctattttg    2640
aatatcgtga aggtgccacg tttggccaga acgaatcaca gattcagcac ggactgatcg    2700
acctcggatc cgatatggat cggggccgga acgggatgat cgaagcgggt caaatcgatc    2760
cttcgaagtc caagatcgtg tgggaatcca gcaagctgcc gaacgacgcg atatccgtgc    2820
cgaaggattt tgatcctgct ctgaaagcgc gcatcacgga atactgacg tccttgtccg    2880
aagagaaagc acagtcgctg atgggctcgg gctataacgg cttcgtgaag gcaaagcaca    2940
gcgattacaa ggtaatcgaa gacgccggcc gcatcctggg aaaactgtaa agcacgaggg    3000
gtccgttctt ggatgagggc agcggacgac aaggtggact gacgcacgcc agctccttgt    3060
ctccgctgca cgaacatacg ggcgcgcatc gcaataccac agaggatgaa ccaatgaatc    3120
agcgaatcga agaagtcatg ctggctaatg tcaagaggga cgtagccagg agaaagcggc    3180
attttgcaac gtcggtcgta gtactcagtt tgctggcagt ggcctggtac gtgtgtcaga    3240
tagaattcca gaagctaggc gccggtttac cgagactatg gtcattcgtc gtgcagatgt    3300
ttccacccga cctgagcgac ctggacgtca ttctaaaagg ggctggcgag acgctcgcca    3360
tggcgacgat tggcacgata ttcgccacaa tcattgcatt tccgctggca ctcatggctg    3420
cgcgtaatac ctgtccgaac aagtggacct atcgggtatc ccgcgccatc ctgaacgcca    3480
gccgcggcac ggagacattt gtctatgcac ttgtatttgt agcagcagtg ggcttcggtc    3540
cgttctccgg cgtactggcc attactttcc acatggtagg ggcaatcggc aaaatgtttg    3600
ctgaagccat cgagcccgtt gaccaagggc cgttggatgc gctcgccttg accggtgcca    3660
gcagggcaaa gattatccgc tacgtctga tcccggatgt tatgccgcac ctgatcgcga    3720
gcgttctata catttgggaa ttcagtgtca gaacgtccac agtactgggc atcgtaggcg    3780
caggtggaat tgggcagacc ctgaaagata ctgtggactt gttggaattc aacaagatga    3840
ttacggtact ggcggttgta ttgctgatgg tgtcggcaat cgatttcatc agtgaccggc    3900
tcaggtactt gatattggac acaaaacgcg agggattcga aactctccct gcgaataact    3960
gattgcttca cgtattactg gaagggaggt tcgcaatgaa agatgtagcg ttgcagttaa    4020
agaatgtcgg taagtcatac ggcaataaag ttgtcctgga atcgattgac ttcgaagtac    4080
gtcacggctc aatggttgcc ttgctcggca caagcggggc agggaagtcg acgcttttcc    4140
gatgtctcac tggccttgag ccgattgact ccggttctat cgtggcgctc ggagaatcca    4200
tacatgaact gtctccggcg cgtctgcggg cagtacgtgg ccagatcggg ttcgtgttcc    4260
```

```
aacaactgca cctggtgaaa aggttctcag cactcgagaa tgtattgggt gcgcgtctgg    4320
cagagatgcc catttggcgc gtcacattga aaagcttcag ccgggctgac aaagtgctcg    4380
cgttcgaatg tctggaccgg gtcggcatgc tcgattatgc aaacacgcct acgcaactgc    4440
tgtcaggcgg tcagcaacag cgtattgcga tagcgcgagc cttggcgcag aagcccaaga    4500
ttattattgc ggacgaaccc gtctccagcc tcgatccgct gacggcgcgc tcggttctgc    4560
aaacgctgaa agccgcggct acagatctta atgtcgcggt cctgtgcagc ctgcaccagg    4620
tagacctggc ccgtgagttt ggcgaccgca tcgtgggcat gcgcgacgga cgtgtcgttt    4680
tcgacggcac gccagcggaa ttcaccgacg agcgcgtgca tgcgctttac caggtgcccg    4740
ctgggaagat gcaccagcgg ccgagagcga cgcgcagcac tcggtggccg gtctggctgt    4800
ggcatgaggg gcgaagcgat gaccacatcc acacgcccca tacccgtgcc gccccagggc    4860
accgcactgc actggcacct gagcgcgccc tacaacgcca acatctgct ggtgctgatc     4920
gccgtcatgg tgctgttgtt cgtgaccgga caacgcaccg aaatggaccg catggtggcc    4980
atgacggcac aggccgtggc caagaccgtg ggcctggctg acgattcaca agtcgcgcgc    5040
ggcttgtcgc gcgtcggtca agccatgtgg ccacccgcca tcgcagaaac cgaagaggtg    5100
ggccggattc aggacctgga tcgccagaag ctgcccctgt tctcgcacat cgagacccag    5160
gagcgcgtcg agcagaagat gaatctggac acgctgaaga tggaagccac gacggaaacc    5220
gtcgaagtgc tggtcaagcc ggtcggctat gtctggacgg ttttcatcaa gatgatcgag    5280
acctggagat tgcgctgtgg ggcacgatcc tgtcggtgct ggtgtcgatt ccctggcgt     5340
atttcgcggc ccgcaactac tagccccaac cgttttacct acaccgctgc ccgcggcacc    5400
atcagtctgc tgcgttcagc gccggaactc atcgtcgctt tgttcctggt gctggcctac    5460
ggctttggcc ccatcgctgg cgtgctggcg ctgggcctgc atgcggccgg cttcctgggc    5520
aagttctacg ccgaggacat cgagaacgcc gacaagaagc cgcaagaggc gctggaggcc    5580
atcggcgcgg gcaagctcaa gacgctgtgg tacggcgtca tcccccaggt cttgccgcaa    5640
tacatcgcct acaccgccta catcctggac cgcaacctgc gcatggccac cgtcatcggt    5700
ctggtgggcg cgggcggcat cggccaggaa ctcaaggggc gttttgacat gttccagtac    5760
ggccatgtca tgaccatcct gatcgcgatc ttcgtctttg tgttcgtgct ggaccagttg    5820
caggcgcgca tccgcgccaa gctgatctga ggcgaccgct gacaacaagg aacaacatga    5880
caaacacttc tgaagcaccg gatcgtgcgc agtggctgcg gctgtggtcg gccttgccgg    5940
ccgcagcggt caaggccctg gcggccgatc tggcgggcca gcaccgggtc gaagacctgg    6000
cgttgccgca atccggtctg ggcctgctgc cgctgaccga cagcgccctg gcgataccgc    6060
atttcatcgg tgagattccc ttggcacaag cgcatgtgcg ggtcacgacc acccaagggc    6120
agtcgatcga aggcgcggcc attctggtgg acgaccgtgc cggtgtggcc cgttccatgg    6180
ccatcctgga cgcggtgctg gcggcccgca tgccaggttg tgaagcggcc ctgcggttgc    6240
tcacccaggg tgcgaccgcc gtggcggaac aaggccgcca gcgccgcgcc ttactcgcgg    6300
ccacgcgggt ggactttgcc ctgctgggaa cgaacgagga ggacgatgat gaatgagact    6360
gggatggcgc cggcaccggc agaagccgcg tggcgcatct ggcaagcgcc gcgccagcaa    6420
acggcgtttc gccagttgat gaccgcgttt tcctatccgg gccgcgtggt gccactggcc    6480
gatggcgctg aatcgcgcgct cctgctggtg ttgaccaccc tggtggacag cgcctgtgcg    6540
ctggccgatc cgctgcacgc gctatcaagc gacgatctgc gccgactggg cgtgcgctcg    6600
```

```
gccagtgtgg aggcggccga gttcgtgctg gccgatggca accgtttgct ggaggccacg    6660
ccgcgcctgg gatcgctgga aaaccccgaa caaggcgcga ccgtggtgat gcgcgtctcc    6720
cgtttcggtg agggtcccca tctgcggctc accgggccgg gtattcaaca cgagcaggtg    6780
ctgcaggtca gcggcatcga tccgggctgg tggaagcaac ggtccgaatg gaatgcccac    6840
ttcccgctgg gcgtggacct gattctggtg agcgggcacg aggtcgcggt attgccccga    6900
accacccaca tcaacctcaa aggagcccac tgatgggata cgttgccatc aagggcggtg    6960
gccgggccat cgccggtgcc gaagccgccg tcgaagccct gcgctgcgcc gaagggccag    7020
cgggtacgcc gctcacgctg tcggccatcg aacagcagtt gcggttgctg acatcgcgcg    7080
tcgtgtcgga agggggcctc taccacccac gcctggccgc tctggccatc aaacagatgc    7140
agggcgacac actggaagcg gcgttcgctc tgcgcgccta ccgctccacc aagccacgcc    7200
tgatggatgt gccggtgcag gacacgagcc gcatgcgcct aatccgccgg atttcgagcg    7260
ctttcaagga catccccggc ggacagatgc tgggcccgac caccgactac gcgctgcgcc    7320
tgatgcgtct ggatttggcc aacgagtcgc ccgaggactt tcgcgcggtc tcgcggcggt    7380
ttctggacag cgtggccgac accgacctgc ccgacagctt ccccaaggtg gtcgatgcct    7440
tgcgtgacga aggcttgctg ccgccgctga cccggcgcgc ccatgcggcg ttcgacatca    7500
cccgcgaccc gctggttttc ccagtgccgc gttcggcggc cctggccacc atggcacgcg    7560
ccgaaaccgg ctcgctcttg gcgattgcgt attccaacat gcgtggctat ggcgacgtgc    7620
accccaccat cgccgagctg cgcgtgggct atgtgccggt gatgctgccg cacccggtga    7680
caggcgagcc catcgaagcc ggtgaggtac tgatgaccga atgcgaagtg gtggccatgt    7740
ttgagggtga tgctaccgac ggcccaccca ctttcaccct aggctatggc gcctgtttcg    7800
gtcacaacga agtcaaggcc atcgccatgg ccatcctcga ccgcgccctg caaaagggta    7860
tgcgcgacgg tcccagcaac ccgtcggaag accggaatt cgtgctgctg cacgtcgatg    7920
gcgtggattc gatgggcttt gccagtcact acaagatgcc gcactacgtg accttccagt    7980
ccgacatgga ccggctgcgc accacgcagg acaaggcaac cgcacaaccg acccaagaag    8040
gagcgccatc atgaacccgg gctacgaact gccctggac gaggcgggct acagcttcgg    8100
cttcctggac gaatacgcca agcgcgaggt gcgccgcacc atcctcaagg cgatcagcat    8160 cccggttac cagacgccct atgcctcacg cgaaatgcct atgggcgcg ctttggcac    8220 cggcggtctg caggttacgc tgtcgctgat tggcgagggc gacaccctga aggtgatcga    8280
ccagggcgcg gacgactccg tcaacgcggt gaacctgcgt cactttgtgg aactgacctg    8340 ccccgggcgtg gacaccacag aacacacgct tgatgccact ctgatccagt cgcgccaccg    8400
cattccggaa acgccgctga ccgaagcgca ggtgttgatc ctgcaagtgc cgtatccgga    8460
cccactggtg gtggtggaac cctccgaggc tcgacgcaag gtcatgcacg gcgaaggcga    8520
ctattcgcgg ctgctgacca agctgtacga ggacatcgtg cagtttgacg agatcaccat    8580
ctcgcaccgc taccccacgc gcatcaacgg ccactatgtg atcgaccca gcccgatccc    8640 gcgctacgac gtgccgcagt tgcaccagag cccggcgctg atcctgctgg gtgcggggcg    8700
cgagaaaaaa atctatgcgg tgccgccgta cacccgcgcc gacccgctgg cgttcgacga    8760
cgtgccattc cgcaccgaag acttcaccaa cgaacacggc cagcgccgcg cctgcgaacg    8820
gtgcggcgcc accgacagct tcctcgacga gctcattgcc gacgatggcg gcaagcactg    8880
gcattgctcg gactcggatt tttgcaatag ccgtatggcc cgccaggctg aacaagctca    8940
ggagaccacg gtatgaaaaa aattctggaa gtacgcggac tgaccaagat ccacggccgg    9000
```

```
ggttgcgaac tctgcctgga gagcactggc cccgacatgg acaccaacat ctgcccacac   9060
tgtggctcgg tggtggcctg ccacaacatc agcctggacc tgcacgaggg cgagatcctc   9120
ggcatcatgg gcgagtccgg cagcggcaag tccaccgtgg tcaagacgct gttcttcgac   9180
gatgagccca ccgctggtga agccctgttt tttgacggcg agcgccagtg ggacatgttc   9240
gcgctcaacg ccgcgcagca gcgctggctt gcgcaaccac cgctttggca tggtgtacca   9300
gaacccgcat ctgggactca atttcaacgt ctcggccggc ggaaacattt gccgagcgcc   9360
ttgctgatga gcgacctggc ccactacggc gaaatccgcg aacgggcgcg cagcttgttg   9420
gcgcgcactg aggtgttggc agaacgcatg acgagtcgc ccaagaagtt ctcgggcggc   9480
atgcagcagc gcgtgcagat cgccaaggca ctggccaccc agccgccgct gctctacctc   9540
gacgaggtca ccaccggcct ggacctttcg gtgcaggcgc gcatcctgga cctgattctg   9600
gaaatccagc aggagctggg caccgccatg atcgtggtca cccacgatct gggtgtcatc   9660
cgcctgctga ccgacgcac gatcgtcatg aaatacggcc gcggtcatcg aagtccgggc   9720
tgaccgacca gatcctcgaa gaccccagc acgcctacac ccagcgcctg gtcgcgtcgg   9780
cttctctgag gaaacctgaa tcatgcaaga agccatcctc aaaatcgaag gtctctccaa   9840
acagttccag ctgcacgacc agaacaaact gatcccgtcg tgtgcacagg ttcaactgga   9900
ggtgtttgcc ggcgagctga ccgcgctgat cggcccgacc ggcgccggca atcgtcggt   9960 gctcaaggcc atttaccgca cctacctgcc cagcagtggg cgcatccttt accgggacgc  10020
caacggtgcc atcaccgatc tggcccaggc cagcgaacac cgcatgctgg agctgcgcaa  10080
gcaggacctg ggtttcgtca cccaatttct gcactgtcta ccgcgcaagt cggcggtcga  10140
ggtagtggcc gagccgctgg tgcagcgggg cagcccgcgc gaagctgctg ccgagcgcgc  10200
gcgcgaactg ctggccctgc tcaacgtgcc ggaacgcttg tgggcggtac cacccgccac  10260
cttctcgggc ggcgagaaac agcgcgtcaa cctggcacgc gggctgatcg cccggcctcg  10320
gctgctgttg cttgacgaac ccacggccag cctagacccg tccaccaccg accgcgtggt  10380
ggagctgttg aagtccatca aggccgaagg cgtggccatg ctggccatct tccacgaccc  10440
cgaacttgtc cgacgcctgg ccgatcgcgt cgtaaccctc acgcccccgg tgtctgcggc  10500
ggcattgctg gagacctgtg cctcatgaat cccattttgc tgaccatgc ccgcgtggtg  10560 ttccccaccg aagtccgtga caacgtggcc atcctgatcg aaggcgacac catcacagca  10620
tcgacccggc cagcagcgca ggtgccaccg agatcgacct gcgcggctcg caccctgatg  10680
ccaggtctga tcgacctgca ctgcgacgca atggagaaag aggtggagcc gcggcccggc  10740
gtgcacttcc cgctggagtt cgcctgtgcc caggccgaca agcgcaatgc ggcggccggc  10800
atcacgacgg tgtttcatgc cctgtccttt gccaaccacg agctgggcgt gcgcaacaac  10860
gccttcgccg ccgagatcgc ccgttcgatt ggcgactggc aggcccatgc cctgatcgac  10920
aaccgggtgc atgtgcgtta cgaggtgacg acgaaacgg cgccgccggt gctgtcggcg  10980
ctgctgcagg acggtcatgc gcacctcatg tctttcatgg atcacagccc cggtcagggt  11040
cagttccgcg atgtcgaggc gtaccgcgcc tacctggcca agacctacaa gaccgatgag  11100
gcgcagatcg acgacatcct ggcgcgcaaa gccggggccg cacagggcgc catgcggcgc  11160
atggagcagc ttgcggaact ggccgtgcg tgcggcgtgt ccattgccag ccacgacgac  11220
gacagcccga gaaagtggc gaccgtcaag gccctgggcg ctgtggtgtc ggagtttccg  11280
gtgaacctgg agacggcaca ggccgcccgt gcacaaggcc tggccacctt gtttggcgct  11340
```

```
cccaacatcc tgcgcggcaa gtcccagtcg ggcaacatgc gtgccctcga tgccgtgctg   11400
gccggtgtcg ccgactgcct gtgcggtgac tactcgccag cggcgctgtt gccgtcggtc   11460
atgcgcttgc ccgatctggc cggcatcccc ctggccgagg ctgtggccct cgtcacgtgc   11520
aacccagctc gtgctgcagg tttgcacgac cggggcgaga tcgccgtggg caagcgcgca   11580
gacctgattg cggtcaaaac catgggcgga ctgccacagg ccgagcgggt ctggtcgggc   11640
ggtaaagctt cgctggtcgc gcattttgac cacgcctgag agggactggc acatgcgaac   11700
tcgcctcatc tacgtggtcg cgcctcgggc agcggcaag gacacgctca tgggccatgc    11760
ccgccagaag ctggcgggtg atcccagggt gtgttttgcc catcgctaca tcacccgacc   11820
cgcaacggca ggcggcgaaa accatgtggc cttgaccacg gaggaattca ccgctcgcca   11880
gaacggcaag ctcttttgcca tgcactggtc cagccacggc ctgcattacg gaatcggcat   11940
cgagatcaac cagtggctgg gcaaaggcat cacggtggtg atcaacggct cgcgggaata   12000
cctggacgag gcccgccaac gttacccgga gctgctgccg gtgacgattg acgtggccac   12060
caccgtgctg cgtgatcggc tgctggcccg tggccgcgag gatgccgaat ccattgagca   12120
gcgcctgcac cgccatgaaa cgttgcgcct gcagcccgtg cccggtgtgc tcatccagaa   12180
caacggaccc gtcgaggtgg ccggcgaagc gctgatccgg ttgatcgcag aacacaccca   12240
aggagcgcca gtatgcgtgt gagttttctg ggcacgggcg ctgcgggcgg ggttccgctc   12300 tacgttgca cctgccgggc ctgtgaacgc gcaaggaccg agccacactt cgtccgccgc    12360
ccttgcagcg ccctgattga atccggaggt acccgggtgc tactggatgc cgggctgatg   12420
gaccttcacg aacggtttgc gccgggtagc ctggacgcga ttgttctcac gcactaccac   12480
cccgaccacg tgcagggact cttcatctg cgctggggta aggggacgcc catcacagtc     12540
tatgccccac cagacagcga aggctgcgcc gatttgttca agcaccctgg tgtactggcc   12600
ttcgagacgg tgcacaagtt cgaggccttc accgtcgggg cgctgcgcct gacgcccctg   12660
ccgctgcttc actccaaacc cacgctgggc tatgccatcg agggcaccca gggccaacgc   12720
ttcgcctacc tcacagacac cctgggtttg ccgccgaagt cggccaagtt cctgcgcgcc   12780
tggggcgact tgacatggc catcgactgt tcctatccgc cgcacccgac cccgaaaaac    12840
cacaacgatt gggacgaagc acatcggtgt gccatcgaat ctggtgcccg catcacctgg   12900
ctcacccatg ccggtcatgc gctggacgac tggatgatgg aagagacgcc gagcgtcgca   12960
agtcatatcc ggctggcccg ggacggcagc acggccgaca taccgtccca aacgcaatga   13020
acgcgccgct ggcactggcc ctgtcggtgg ccatgcacgt cacctggaac ctgatggcac   13080
ggcatttgcc cagggaatcg aacccgctgt ggtgggtgtt gctcgcccat ctggtgctgt   13140
ttgcgccctg ggggttctgg gagctggcga caaccgtcgt ttggtcactg gagatgacgc   13200
tgctactgat cgtatcggcc actgcgaatg tggtttattt ctccggtctg gccagggcct   13260
acgagcacgc accggtcgca ctggtctatc ctctggtgcg cagttcacct cttttcattg   13320
cgatctgggg cacgctgttc ttcggtcaaa atctcccgcc cattgcctgg ctgggcattg   13380
gcatcagcgt gctgggcttg ctcgtcatgg catcgagtgc tcaacagggg tcggatcgac   13440
gagcattccg atgggccatg ctggccatgt tggcgacaag cgtttattcc ctgagtgaca   13500
aggcggccac cgaacacatc ccaagcttca tggggctcgt gggttttctg tccgtcggct   13560
acctggcatc ctggatcagc atgacctggc gcatgcatcg gcacaccgc agttgggtgc    13620 cggcacagcg cattgatctc gcgtcgctgg ctcttggcgg aacctgtatc ggtctcgcct   13680
acgccttggt tatccacgcc atgcgccagt tgcctgcggc ggaggtcgtg tcgtacacca   13740
```

```
acgccggtat cgtgctcgct gcagttctct ccattttttt gttcaatgac aaagtcggat    13800
ggcaaaagag aatcatgggg gtcgtgatca tcacgagtgg tttggggggtg cttgccatga   13860 ggtgagcgac acaataccaa ccatcgcaca ccagcattcc aacccggctc gcgacctgcc    13920
ggtgaagtaa aagcgacttc cgatatgtcc caaatttccc gatacgtcga ggccgccgag    13980
cgtgacaaca cgcgtcgaag ctatgccgca gccattcgcc atttcgaggt ggagtggaaa    14040
ggcttgctgc caacgaccgc tgatgcaacc tcccgttacc tggctgacca cgcggccacg    14100
ctggcgatca gcaccctccg tcagcggctc gccgcgctct cgcgctggca catcgaccat    14160
ggttttgcag acccgaccaa ggcacccttg gtgcgccagg ttctcaaagg cattcgctcc    14220
attcactcgg ttgcagaaaa gcgggcacgc ccccttgaaa tcgatgtcgt ccagcagatc    14280
gatcaatggc tgggggtggc catcggcaac gcagaacgca gcgatgaccg attggcgctg    14340
cttcgccaca cccgcaaccg cagtttgctg ctgctgggtt tctggcgggg atttcgatcg    14400
gacgagttgg tcaacctgcg ggtggagaac gtggaagtct cgcctggcga agggctgtcg    14460
tgctacctga gccgcagcaa gggcgatcgg cagatgctgg gccgcgtata caaatgtccg    14520
gcgctgtccc gcctgtgtcc tgtgacggct ttcacggcat gggtcagtct ggtcggcctg    14580
acccaaggcc cggtgtttcg caagatcgac cgctgggggc gaatcggtca agaagggctg    14640
catgccaaca gcctgatccc attgttgcgc agccttttgg ctgaggccgg ggtcccgct    14700 tccgaggcat acagcagcca ctccctgcgt cgcggatttg ccggttgggc tcgcgccagc    14760
ggttgggaca tcaaggaact catggagtac gtgggctgga aggatgtcaa atcggccatg    14820
cgttatctgg atgcctccgg cagcgcactt caggcccggt ttgaggcggg tctcgcaaca    14880
ctggccccag cagatcgagc ggatcggtca ccaccgcctt cgatgcacgc gccggccgag    14940
caaaccaagg gaacaggccc agaggccccg tctgcctga                          14979
```

<210> SEQ ID NO 25
<211> LENGTH: 29
<212> TYPE: DNA
<213> ORGANISM: Artificial Sequence
<220> FEATURE:
<223> OTHER INFORMATION: Artificially Synthesized Sequence

<400> SEQUENCE: 25
aagaattcat gctacatttg tttgctggc                                     29

<210> SEQ ID NO 26
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 26
aaatctagat tacaggaact gcaaggagag                                    30

<210> SEQ ID NO 27
<211> LENGTH: 29
<212> TYPE: DNA
<213> ORGANISM: Artificial Sequence
<220> FEATURE:
<223> OTHER INFORMATION: Artificially Synthesized Sequence

<400> SEQUENCE: 27
aagaattcat gctaaattta tttgttggc                                     29

<210> SEQ ID NO 28
<211> LENGTH: 31
<212> TYPE: DNA
<213> ORGANISM: Artificial Sequence
<220> FEATURE:
<223> OTHER INFORMATION: Artificially Synthesized Sequence

<400> SEQUENCE: 28
aaatctagat taaatcaact gcaatgctat c          31

<210> SEQ ID NO 29
<211> LENGTH: 32
<212> TYPE: DNA
<213> ORGANISM: Artificial Sequence
<220> FEATURE:
<223> OTHER INFORMATION: Artificially Synthesized Sequence

<400> SEQUENCE: 29
aagaattcat gcaaacgatt atccgtgtcg ag         32

<210> SEQ ID NO 30
<211> LENGTH: 32
<212> TYPE: DNA
<213> ORGANISM: Artificial Sequence
<220> FEATURE:
<223> OTHER INFORMATION: Artificially Synthesized Sequence

<400> SEQUENCE: 30
aaatctagat cagataaagt gcttacgcaa cc         32

<210> SEQ ID NO 31
<211> LENGTH: 33
<212> TYPE: DNA
<213> ORGANISM: Artificial Sequence
<220> FEATURE:
<223> OTHER INFORMATION: Artificially Synthesized Sequence

<400> SEQUENCE: 31
aagaattcta gcaggcgtct atatttggca tag        33

<210> SEQ ID NO 32
<211> LENGTH: 33
<212> TYPE: DNA
<213> ORGANISM: Artificial Sequence
<220> FEATURE:
<223> OTHER INFORMATION: Artificially Synthesized Sequence

<400> SEQUENCE: 32
gctctagagc tttgggagtt atttgaactt gcg        33

<210> SEQ ID NO 33
<211> LENGTH: 32
<212> TYPE: DNA
<213> ORGANISM: Artificial Sequence
<220> FEATURE:
<223> OTHER INFORMATION: Artificially Synthesized Sequence

<400> SEQUENCE: 33
aagaattcaa tcgggttcga gctgatgggc tc         32

<210> SEQ ID NO 34
<211> LENGTH: 34
<212> TYPE: DNA
<213> ORGANISM: Artificial Sequence
<220> FEATURE:
<223> OTHER INFORMATION: Artificially Synthesized Sequence

<400> SEQUENCE: 34
aaatctagat cgccacacgc tccagatcta tcac        34

<210> SEQ ID NO 35
<211> LENGTH: 42
<212> TYPE: DNA
<213> ORGANISM: Artificial Sequence
<220> FEATURE:
<223> OTHER INFORMATION: Artificially Synthesized Sequence

<400> SEQUENCE: 35
cggtacccgg ggatcctagg agcatcacca tgtttgcaga gc        42

<210> SEQ ID NO 36
<211> LENGTH: 45
<212> TYPE: DNA
<213> ORGANISM: Artificial Sequence
<220> FEATURE:
<223> OTHER INFORMATION: Artificially Synthesized Sequence

<400> SEQUENCE: 36
cggtacccgg ggatctcaga tcagcttggc gcggatgcgc gcctg        45

<210> SEQ ID NO 37
<211> LENGTH: 1392
<212> TYPE: DNA
<213> ORGANISM: E.coli

<400> SEQUENCE: 37
atgctggctt tcttaaacca ggttcgcaag ccgaccctgg accttccgct cgaagtgcgg        60
cgcaaaatgt ggttcaaacc gttcatgcaa tcctacctgg tggtctttat cggctacctg       120
acgatgtacc tgattcgcaa gaactttaac atcgcgcaga acgatatgat ttcgacctac       180
gggttgagca tgacgcagct ggggatgatc ggcctgggtt ctccatcac ttatggcgtg       240
ggtaaaacgc tggtttccta ctacgccgac ggcaaaaaca ccaaacaatt cctgccgttc       300
atgctgatcc tctctgctat ttgtatgctg ggcttcagtg ccagtatggg cagcggctcg       360
gttagcctgt tcctgatgat tgccttctac gcctaagcg gctttttcca gagtaccggc       420
ggttcgtgca gttactccac catcaccaaa tggacgccgc gtcgtaaacg cgggacattc       480
ctcggtttct ggaatatttc tcacaacctt ggcggtgcag gcgcagcagg tgtggcgctg       540
ttcggggcaa attacctgtt cgatggccat gtcatcggca tgtttatctt cccgtcgatt       600
atcgcgctga ttgtcggttt tatcggcctg cgttacggca cgactcccc ggaatcttat       660
ggcctcggca agctgaaga actgttcggc gaggagatca gcgaagagga caaagagaca       720
gaatctaccg atatgaccaa gtggcagatc tttgttgagt atgtgctgaa aaacaaagtg       780
atctggctgc tgtgcttcgc caacattttc ctctatgtgg tacgtattgg tatcgaccag       840
tggtcaaccg tatacgcgtt ccaggaactg aaactctcta aagcggtggc gattcagggc       900
tttacgctgt ttgaagctgg tgcgctggtc ggtacgctgc tgtggggctg gctctctgac       960
ctggcgaacg tcgccgtgg cctggtggcc tgcatcgcgc tggcgctgat tatcgccacg      1020
ctcggtgtgt atcaacatgc cagtaacgaa tatatctatc tggcttctct ctttgcgttg      1080
ggtttcctgg tctttggccc gcaattgttg attggtgtgg ctgctgttgg ctttgtacct      1140
aaaaaagcga ttggcgctgc cgatggtatt aaaggcacct tgcttacct gattggtgac      1200
agctttgcca gttaggtct ggaatgatt gccgatggga cgccggtatt cggccttacc      1260

```
ggctgggcag gcaccttcgc cgcgctggat atcgccgcga ttggttgtat ctgcctgatg    1320
gcgatagtgg cggtaatgga agaacgcaaa atccgccgcg agaaaaaaat tcagcagttg    1380
acagtggcat aa                                                        1392
```

<210> SEQ ID NO 38
<211> LENGTH: 463
<212> TYPE: PRT
<213> ORGANISM: E.coli

<400> SEQUENCE: 38

```
Met Leu Ala Phe Leu Asn Gln Val Arg Lys Pro Thr Leu Asp Leu Pro
1               5                   10                  15

Leu Glu Val Arg Arg Lys Met Trp Phe Lys Pro Phe Met Gln Ser Tyr
            20                  25                  30

Leu Val Val Phe Ile Gly Tyr Leu Thr Met Tyr Leu Ile Arg Lys Asn
        35                  40                  45

Phe Asn Ile Ala Gln Asn Asp Met Ile Ser Thr Tyr Gly Leu Ser Met
    50                  55                  60

Thr Gln Leu Gly Met Ile Gly Leu Gly Phe Ser Ile Thr Tyr Gly Val
65                  70                  75                  80

Gly Lys Thr Leu Val Ser Tyr Tyr Ala Asp Gly Lys Asn Thr Lys Gln
                85                  90                  95

Phe Leu Pro Phe Met Leu Ile Leu Ser Ala Ile Cys Met Leu Gly Phe
            100                 105                 110

Ser Ala Ser Met Gly Ser Gly Ser Val Ser Leu Phe Leu Met Ile Ala
        115                 120                 125

Phe Tyr Ala Leu Ser Gly Phe Phe Gln Ser Thr Gly Gly Ser Cys Ser
    130                 135                 140

Tyr Ser Thr Ile Thr Lys Trp Thr Pro Arg Arg Lys Arg Gly Thr Phe
145                 150                 155                 160

Leu Gly Phe Trp Asn Ile Ser His Asn Leu Gly Gly Ala Gly Ala Ala
                165                 170                 175

Gly Val Ala Leu Phe Gly Ala Asn Tyr Leu Phe Asp Gly His Val Ile
            180                 185                 190

Gly Met Phe Ile Phe Pro Ser Ile Ile Ala Leu Ile Val Gly Phe Ile
        195                 200                 205

Gly Leu Arg Tyr Gly Ser Asp Ser Pro Glu Ser Tyr Gly Leu Gly Lys
    210                 215                 220

Ala Glu Glu Leu Phe Gly Glu Glu Ile Ser Glu Glu Asp Lys Glu Thr
225                 230                 235                 240

Glu Ser Thr Asp Met Thr Lys Trp Gln Ile Phe Val Glu Tyr Val Leu
                245                 250                 255

Lys Asn Lys Val Ile Trp Leu Leu Cys Phe Ala Asn Ile Phe Leu Tyr
            260                 265                 270

Val Val Arg Ile Gly Ile Asp Gln Trp Ser Thr Val Tyr Ala Phe Gln
        275                 280                 285

Glu Leu Lys Leu Ser Lys Ala Val Ala Ile Gln Gly Phe Thr Leu Phe
    290                 295                 300

Glu Ala Gly Ala Leu Val Gly Thr Leu Leu Trp Gly Trp Leu Ser Asp
305                 310                 315                 320

Leu Ala Asn Gly Arg Arg Gly Leu Val Ala Cys Ile Ala Leu Ala Leu
                325                 330                 335

Ile Ile Ala Thr Leu Gly Val Tyr Gln His Ala Ser Asn Glu Tyr Ile
            340                 345                 350
```

Tyr Leu Ala Ser Leu Phe Ala Leu Gly Phe Leu Val Phe Gly Pro Gln
            355                 360                 365

Leu Leu Ile Gly Val Ala Ala Val Gly Phe Val Pro Lys Lys Ala Ile
    370                 375                 380

Gly Ala Ala Asp Gly Ile Lys Gly Thr Phe Ala Tyr Leu Ile Gly Asp
385                 390                 395                 400

Ser Phe Ala Lys Leu Gly Leu Gly Met Ile Ala Asp Gly Thr Pro Val
                405                 410                 415

Phe Gly Leu Thr Gly Trp Ala Gly Thr Phe Ala Ala Leu Asp Ile Ala
            420                 425                 430

Ala Ile Gly Cys Ile Cys Leu Met Ala Ile Val Ala Val Met Glu Glu
            435                 440                 445

Arg Lys Ile Arg Arg Glu Lys Lys Ile Gln Gln Leu Thr Val Ala
    450                 455                 460

<210> SEQ ID NO 39
<211> LENGTH: 1317
<212> TYPE: DNA
<213> ORGANISM: E.coli

<400> SEQUENCE: 39
atgaaaccgt tacattatac agcttcagca ctggcgctcg gactggcgtt aatggggaat      60
gcacaggcag tgacgaccat tccgttctgg cattctatgg aagggaact gggtaaagag     120
gtggattctc tggcccaacg ttttaacgcc gaaaacccgg attacaaaat tgtaccgacc     180
tataaaggca actacgaaca gaatttaagc gcggggattg ccgcatttcg taccggcaac     240
gcgccggcta ttttgcaggt ttatgaagtt ggcaccgcca ccatgatggc gtcgaaagcc     300
attaaaccgg tgtatgacgt gtttaaagag cagggattc agttcgatga gtcgcagttt     360
gtgccgacgg tttcaggtta ctactccgac agcaaaacgg ccacttact ctcccagcca     420
ttcaacagct cgaccccccgt tctctattac aacaaagacg ccttcaagaa agcaggatta     480
gacccggaac agccgccgaa aacctggcag atctggcgg actatgccgc gaaactgaaa     540
gcctccggca tgaagtgcgg ctacgccagc ggctggcagg gctggatcca actggaaaac     600
tttagcgcct ggaacggtct gccgtttgcc agcaaaaaca acggctttga cggcacggac     660
gcggtgctgg agttcaataa gccggagcag gtgaaacaca tcgccatgct cgaggagatg     720
aacaagaagg gcgacttcag ctacgtcggt cgtaaggatg aatccaccga agttctat     780
aacggtgatt gcgcgatgac caccgcctct tccggttctc ttgccaacat tcgcgagtac     840
gccaaattta actacggcgt aggcatgatg ccttacgacg ccgatgcgaa agatgcgcca     900
caaaacgcca ttatcggcgg agccagcctg tgggtgatgc agggtaaaga taaagaaacg     960
tataccggtg tggcgaagtt cctcgatttc ctcgcgaagc cagaaaacgc tgccgagtgg    1020
catcagaaaa ccggttatct gccaatcacc aaagcagcgt atgacctgac ccgtgagcag    1080
ggcttttatg agaaaaaccc aggggcggat accgcgacgc gtcagatgct gaataagccg    1140
ccgttgccgt tcaccaaagg gctgcgtctg ggcaacatgc gcagatccg cgtgattgtg    1200
gatgaagagc tggagagcgt gtggaccggt aagaagacac cacagcaggc actggatacc    1260
gccgttgagc gtggaaatca gttgctgcgc cgctttgaga aatcgacgaa gtcttaa      1317

<210> SEQ ID NO 40
<211> LENGTH: 438
<212> TYPE: PRT
<213> ORGANISM: E.coli

<400> SEQUENCE: 40

```
Met Lys Pro Leu His Tyr Thr Ala Ser Ala Leu Ala Leu Gly Leu Ala
1               5                   10                  15

Leu Met Gly Asn Ala Gln Ala Val Thr Thr Ile Pro Phe Trp His Ser
                20                  25                  30

Met Glu Gly Glu Leu Gly Lys Glu Val Asp Ser Leu Ala Gln Arg Phe
            35                  40                  45

Asn Ala Glu Asn Pro Asp Tyr Lys Ile Val Pro Thr Tyr Lys Gly Asn
        50                  55                  60

Tyr Glu Gln Asn Leu Ser Ala Gly Ile Ala Ala Phe Arg Thr Gly Asn
65                  70                  75                  80

Ala Pro Ala Ile Leu Gln Val Tyr Glu Val Gly Thr Ala Thr Met Met
                85                  90                  95

Ala Ser Lys Ala Ile Lys Pro Val Tyr Asp Val Phe Lys Glu Ala Gly
            100                 105                 110

Ile Gln Phe Asp Glu Ser Gln Phe Val Pro Thr Val Ser Gly Tyr Tyr
        115                 120                 125

Ser Asp Ser Lys Thr Gly His Leu Leu Ser Gln Pro Phe Asn Ser Ser
130                 135                 140

Thr Pro Val Leu Tyr Tyr Asn Lys Asp Ala Phe Lys Lys Ala Gly Leu
145                 150                 155                 160

Asp Pro Glu Gln Pro Pro Lys Thr Trp Gln Asp Leu Ala Asp Tyr Ala
                165                 170                 175

Ala Lys Leu Lys Ala Ser Gly Met Lys Cys Gly Tyr Ala Ser Gly Trp
            180                 185                 190

Gln Gly Trp Ile Gln Leu Glu Asn Phe Ser Ala Trp Asn Gly Leu Pro
        195                 200                 205

Phe Ala Ser Lys Asn Asn Gly Phe Asp Gly Thr Asp Ala Val Leu Glu
210                 215                 220

Phe Asn Lys Pro Glu Gln Val Lys His Ile Ala Met Leu Glu Glu Met
225                 230                 235                 240

Asn Lys Lys Gly Asp Phe Ser Tyr Val Gly Arg Lys Asp Glu Ser Thr
                245                 250                 255

Glu Lys Phe Tyr Asn Gly Asp Cys Ala Met Thr Thr Ala Ser Ser Gly
            260                 265                 270

Ser Leu Ala Asn Ile Arg Glu Tyr Ala Lys Phe Asn Tyr Gly Val Gly
        275                 280                 285

Met Met Pro Tyr Asp Ala Asp Ala Lys Asp Ala Pro Gln Asn Ala Ile
290                 295                 300

Ile Gly Gly Ala Ser Leu Trp Val Met Gln Gly Lys Asp Lys Glu Thr
305                 310                 315                 320

Tyr Thr Gly Val Ala Lys Phe Leu Asp Phe Leu Ala Lys Pro Glu Asn
                325                 330                 335

Ala Ala Glu Trp His Gln Lys Thr Gly Tyr Leu Pro Ile Thr Lys Ala
            340                 345                 350

Ala Tyr Asp Leu Thr Arg Glu Gln Gly Phe Tyr Glu Lys Asn Pro Gly
        355                 360                 365

Ala Asp Thr Ala Thr Arg Gln Met Leu Asn Lys Pro Pro Leu Pro Phe
370                 375                 380

Thr Lys Gly Leu Arg Leu Gly Asn Met Pro Gln Ile Arg Val Ile Val
385                 390                 395                 400

Asp Glu Glu Leu Glu Ser Val Trp Thr Gly Lys Lys Thr Pro Gln Gln
```

Ala Leu Asp Thr Ala Val Glu Arg Gly Asn Gln Leu Leu Arg Arg Phe
       405                 410                 415

Glu Lys Ser Thr Lys Ser
        420                 425                 430

435

<210> SEQ ID NO 41
<211> LENGTH: 1359
<212> TYPE: DNA
<213> ORGANISM: E.coli

<400> SEQUENCE: 41

| | | |
|---|---|---|
| atgttgagta ttttaaaacc agcgccacac aaagcgcgct tacctgccgc ggagatcgat | 60 |
| ccgacttatc gtcgattgcg ctggcaaatt ttcctgggga tattctttgg ctatgcggct | 120 |
| tactatttgg ttcgtaagaa cttgcgctt gctatgcctt atctggttga gcagggattc | 180 |
| tcacgcggtg atttaggttt tgccctttcg gggatctcga ttgcttatgg attttcgaaa | 240 |
| ttcatcatgg gttcggtatc ggatcgctcg aatccgcgcg tttcctgcc cgcaggtttg | 300 |
| attctggcgg cggcagtgat gttgtttatg ggctttgtgc catgggcgac gtcgagcatt | 360 |
| gcggtgatgt ttgtactgtt gttcctctgc ggttggttcc aggggatggg gtggccgccg | 420 |
| tgtggtcgta ctatggtgca ctggtggtcg cagaaagaac gtggcggcat tgtgtcagtg | 480 |
| tggaactgtg cgcacaacgt cggtggtggt attccgccgc tgctgttcct gctggggatg | 540 |
| gcctggttca tgactggca tgcggcgctc tatatgcctg ctttctgcgc cattctggtg | 600 |
| gcattattcg cctttgcgat gatgcgcgat accccgcaat cctgtggctt gccgccgatc | 660 |
| gaagagtaca aaatgatta tccggacgac tataacgaaa agcggaaca ggagctgacg | 720 |
| gcgaagcaaa tcttcatgca gtacgtactg ccgaacaaac tgctgtggta tatcgccatc | 780 |
| gccaacgtgt tcgtttatct gctgcgttac ggcatcctcg actggtcacc gacttatctg | 840 |
| aaagaggtta agcatttcgc gctagataaa tcctcctggg cctacttcct ttatgaatat | 900 |
| gcaggtattc cgggcactct gctgtgcggc tggatgtcgg ataaagtctt ccgtggcaac | 960 |
| cgtggggcaa ccggcgtttt ctttatgaca ctggtgacca tcgcgactat cgtttactgg | 1020 |
| atgaacccgg caggtaaccc aaccgtcgat atgatttgta tgattgttat cggcttcctg | 1080 |
| atctacggtc ctgtgatgct gatcggtctg catgcgctgg aactggcacc gaaaaaagcg | 1140 |
| gcaggtacgg cagcgggctt taccgggctg tttggttacc tgggcggttc ggtggcggcg | 1200 |
| agcgcgattg ttggctacac cgtggacttc ttcggctggg atggcggctt tatggtaatg | 1260 |
| attggcggca gcattctggc ggttatcttg ttgattgttg tgatgattgg cgaaaaacgt | 1320 |
| cgccatgaac aattactgca agaacgcaac ggaggctaa | 1359 |

<210> SEQ ID NO 42
<211> LENGTH: 452
<212> TYPE: PRT
<213> ORGANISM: E.coli

<400> SEQUENCE: 42

Met Leu Ser Ile Phe Lys Pro Ala Pro His Lys Ala Arg Leu Pro Ala
1               5                   10                  15

Ala Glu Ile Asp Pro Thr Tyr Arg Arg Leu Arg Trp Gln Ile Phe Leu
            20                  25                  30

Gly Ile Phe Phe Gly Tyr Ala Ala Tyr Tyr Leu Val Arg Lys Asn Phe
        35                  40                  45

```
Ala Leu Ala Met Pro Tyr Leu Val Glu Gln Gly Phe Ser Arg Gly Asp
 50                  55                  60
Leu Gly Phe Ala Leu Ser Gly Ile Ser Ile Ala Tyr Gly Phe Ser Lys
 65                  70                  75                  80
Phe Ile Met Gly Ser Val Ser Asp Arg Ser Asn Pro Arg Val Phe Leu
                 85                  90                  95
Pro Ala Gly Leu Ile Leu Ala Ala Val Met Leu Phe Met Gly Phe
            100                 105                 110
Val Pro Trp Ala Thr Ser Ser Ile Ala Val Met Phe Val Leu Leu Phe
            115                 120                 125
Leu Cys Gly Trp Phe Gln Gly Met Gly Trp Pro Pro Cys Gly Arg Thr
    130                 135                 140
Met Val His Trp Trp Ser Gln Lys Glu Arg Gly Gly Ile Val Ser Val
145                 150                 155                 160
Trp Asn Cys Ala His Asn Val Gly Gly Gly Ile Pro Pro Leu Leu Phe
                165                 170                 175
Leu Leu Gly Met Ala Trp Phe Asn Asp Trp His Ala Ala Leu Tyr Met
            180                 185                 190
Pro Ala Phe Cys Ala Ile Leu Val Ala Leu Phe Ala Phe Ala Met Met
        195                 200                 205
Arg Asp Thr Pro Gln Ser Cys Gly Leu Pro Pro Ile Glu Glu Tyr Lys
    210                 215                 220
Asn Asp Tyr Pro Asp Asp Tyr Asn Glu Lys Ala Glu Gln Glu Leu Thr
225                 230                 235                 240
Ala Lys Gln Ile Phe Met Gln Tyr Val Leu Pro Asn Lys Leu Leu Trp
                245                 250                 255
Tyr Ile Ala Ile Ala Asn Val Phe Val Tyr Leu Leu Arg Tyr Gly Ile
            260                 265                 270
Leu Asp Trp Ser Pro Thr Tyr Leu Lys Glu Val Lys His Phe Ala Leu
        275                 280                 285
Asp Lys Ser Ser Trp Ala Tyr Phe Leu Tyr Glu Tyr Ala Gly Ile Pro
    290                 295                 300
Gly Thr Leu Leu Cys Gly Trp Met Ser Asp Lys Val Phe Arg Gly Asn
305                 310                 315                 320
Arg Gly Ala Thr Gly Val Phe Phe Met Thr Leu Val Thr Ile Ala Thr
                325                 330                 335
Ile Val Tyr Trp Met Asn Pro Ala Gly Asn Pro Thr Val Asp Met Ile
            340                 345                 350
Cys Met Ile Val Ile Gly Phe Leu Ile Tyr Gly Pro Val Met Leu Ile
        355                 360                 365
Gly Leu His Ala Leu Glu Leu Ala Pro Lys Lys Ala Ala Gly Thr Ala
    370                 375                 380
Ala Gly Phe Thr Gly Leu Phe Gly Tyr Leu Gly Gly Ser Val Ala Ala
385                 390                 395                 400
Ser Ala Ile Val Gly Tyr Thr Val Asp Phe Phe Gly Trp Asp Gly Gly
                405                 410                 415
Phe Met Val Met Ile Gly Gly Ser Ile Leu Ala Val Ile Leu Leu Ile
            420                 425                 430
Val Val Met Ile Gly Glu Lys Arg Arg His Glu Gln Leu Leu Gln Glu
        435                 440                 445
Arg Asn Gly Gly
450
```

```
<210> SEQ ID NO 43
<211> LENGTH: 36
<212> TYPE: DNA
<213> ORGANISM: Artificial Sequence
<220> FEATURE:
<223> OTHER INFORMATION: Artificially Synthesized Sequence

<400> SEQUENCE: 43
cacaaggaga ctgccatgaa gcccaaagtc gtcctc                                  36

<210> SEQ ID NO 44
<211> LENGTH: 36
<212> TYPE: DNA
<213> ORGANISM: Artificial Sequence
<220> FEATURE:
<223> OTHER INFORMATION: Artificially Synthesized Sequence

<400> SEQUENCE: 44
cagtttatgg cgggctcacg ccgcctttac tcccgg                                  36
```